US012366558B2

(12) United States Patent
Kim et al.

(10) Patent No.: US 12,366,558 B2
(45) Date of Patent: Jul. 22, 2025

(54) ULTRASONIC TRANSMISSION DEVICE AND WAVE CONTROL METHOD

(71) Applicants: SEOUL NATIONAL UNIVERSITY R&DB FOUNDATION, Seoul (KR); CENTER FOR ADVANCED META-MATERIALS, Daejeon (KR)

(72) Inventors: Yoon Young Kim, Seoul (KR); Chung Il Park, Chungcheongnam-do (KR)

(73) Assignees: SEOUL NATIONAL UNIVERSITY R&DB FOUNDATION, Seoul (KR); CENTER FOR ADVANCED META-MATERIALS, Daejeon (KR)

( * ) Notice: Subject to any disclaimer, the term of this patent is extended or adjusted under 35 U.S.C. 154(b) by 677 days.

(21) Appl. No.: 17/637,754

(22) PCT Filed: May 31, 2021

(86) PCT No.: PCT/KR2021/006722
§ 371 (c)(1),
(2) Date: Feb. 23, 2022

(87) PCT Pub. No.: WO2021/242063
PCT Pub. Date: Dec. 2, 2021

(65) Prior Publication Data
US 2022/0291176 A1 Sep. 15, 2022

(30) Foreign Application Priority Data
May 29, 2020 (KR) .................. 10-2020-0065393

(51) Int. Cl.
G01N 29/34 (2006.01)
A61B 8/00 (2006.01)
G01N 29/04 (2006.01)

(52) U.S. Cl.
CPC ............. *G01N 29/34* (2013.01); *G01N 29/04* (2013.01); *A61B 8/00* (2013.01); *G01N 2291/023* (2013.01)

(58) Field of Classification Search
None
See application file for complete search history.

(56) References Cited

FOREIGN PATENT DOCUMENTS

| KR | 10-0588532 B1 | 6/2006 |
| KR | 10-2007-0065934 A | 6/2007 |
| KR | 10-0777239 B1 | 11/2007 |
| KR | 10-0844173 B1 | 7/2008 |
| WO | 2020-027409 A1 | 2/2020 |

OTHER PUBLICATIONS

International Search Report for PCT/KR2021/006722 mailed Sep. 7, 2021, all pages.

*Primary Examiner* — Walter L Lindsay, Jr.
*Assistant Examiner* — Geoffrey T Evans
(74) *Attorney, Agent, or Firm* — Kilpatrick Townsend & Stockton LLP

(57) ABSTRACT

The present disclosure relates to an ultrasonic transmission apparatus and a wave control method, and more particularly, to an ultrasonic transmission apparatus and a wave control method which enable an ultrasonic wave to transmit through an obstacle.

15 Claims, 54 Drawing Sheets

A frequency universal point that satisfies MMC at any frequency

A frequency universal point that satisfies MMC at any frequency

ULTRASONIC TRANSMISSION DEVICE AND WAVE CONTROL METHOD

TECHNICAL FIELD

The present disclosure relates to an ultrasonic transmission apparatus and a wave control method, and more particularly, to an ultrasonic transmission apparatus and a wave control method which enable an ultrasonic wave to transmit through an obstacle.

BACKGROUND ART

When an ultrasonic wave traveling in one medium encounters an obstacle composed of a dissimilar medium, much energy is reflected due to an impedance difference between the medium and the obstacle, and only part of ultrasonic energy may transmit therethrough.

In general, when encountering an obstacle, a reflectance of an ultrasonic wave increases in proportion to a difference in impedance between an obstacle and a travel medium. For example, because impedance of water is approximately 30 times impedance of iron, wave energy passing through an obstacle such as an iron plate in water is very small. Accordingly, when there is an obstacle, it is very difficult to perform an ultrasonic inspection of an inspection body across an obstacle.

In order to solve this problem, several technologies have been developed and proposed to allow an ultrasonic wave to transmit through an obstacle. A widely known technology for transmission of ultrasonic wave is a technology using Fabry-Perot Resonance. The Fabry-Perot resonance refers to a phenomenon in which transmission energy of an ultrasonic wave is maximum when a thickness of an obstacle is an integer multiple ($0.5\,n\lambda$, n: natural number, $\lambda$: wavelength) of a half-wavelength of an ultrasonic wave transmitting through the obstacle.

However, the present technology has a disadvantage in that a frequency for determining a maximum transmittance of an ultrasonic wave is determined according to a thickness of the obstacle, and the ultrasonic transmittance energy is very low for a fairly wide frequency band.

Accordingly, there is a need for an ultrasonic transmission apparatus capable of solving the problem.

DESCRIPTION OF EMBODIMENTS

Technical Problem

The present disclosure provides an ultrasonic transmission apparatus and a wave control method which enable an ultrasonic wave to transmit through an obstacle.

Solution to Problem

An ultrasonic transmission apparatus according an embodiment of the present disclosure
is an ultrasonic transmission apparatus for performing an ultrasonic inspection by injecting an ultrasonic wave into an object including a medium and a body to be inspected inside and including an obstacle outside, and includes
an ultrasonic generation device configured to generate an incident wave; and
an ultrasonic transmission module located between the obstacle and the ultrasonic generation device and located on a travel path of an incident wave generated by the ultrasonic generation device, wherein
the ultrasonic transmission module includes
an ultrasonic transmission member, and
a position variable device configured to vary a position of the ultrasonic transmission member.

In the ultrasonic transmission apparatus according to an embodiment of the present disclosure,
the position variable device
varies a distance between the obstacle and the ultrasonic transmission member
to cause a phase and a magnitude of a transmitted wave passing through the ultrasonic transmission member and the obstacle to be the same as a phase and a magnitude of the incident wave generated by the ultrasonic generation device.

In the ultrasonic transmission apparatus according to an embodiment of the present disclosure,
the ultrasonic transmission member
selectively varies impedance and
a phase, a ratio $\alpha$ between a phase of the obstacle and a phase of the ultrasonic transmission member and a ratio $\beta$ between impedance of the obstacle and impedance of the ultrasonic transmission member are defined according to following Equation (1), $$\alpha \equiv \frac{\varphi_L}{\varphi_B} = \frac{k_L d_L}{k_B d_B},\ \beta \equiv \frac{z_L}{z_B} \qquad \text{Equation (1)}$$

where $z=\rho c$ ($\rho$: density c: wave velocity)
$\Phi=kd$ (k: wavenumber, d: thickness of dissimilar material)
$k=\omega/c=(\omega$: frequency [Rad/s])
$\omega=2\pi f$ (f: frequency [Hz]))
(subscript) 0: progress medium, B: obstacle, L: ultrasonic transmitter.

In the ultrasonic transmission apparatus according to an embodiment of the present disclosure,
the ratio $\beta$ between the impedance of the obstacle and the impedance of the ultrasonic transmission member and the ratio $\alpha$ between the phase of the obstacle and the phase of the ultrasonic transmission member each satisfy following Equation (2), $$1 = |\chi(\alpha, \beta)| \qquad \text{Equation (2)}$$

$$\left(\text{here, } \chi(\alpha, \beta) \equiv R_B\left(R_L - \frac{T_L^2}{R_L}\right),\right.$$

$$R_B = \frac{-\frac{i}{2}\left(\frac{z_0}{z_B} - \frac{z_B}{z_0}\right)\sin(\varphi_B)}{\cos(\varphi_B) + \frac{i}{2}\left(\frac{z_0}{z_B} + \frac{z_B}{z_0}\right)\sin(\varphi_B)},$$

$$R_L = \frac{-\frac{i}{2}\left(\frac{z_0}{z_L} - \frac{z_L}{z_0}\right)\sin(\varphi_L)}{\cos(\varphi_L) + \frac{i}{2}\left(\frac{z_0}{z_L} + \frac{z_L}{z_0}\right)\sin(\varphi_L)},$$

$$\left.T_L = \frac{1}{\cos(\varphi_L) + \frac{i}{2}\left(\frac{z_0}{z_L} + \frac{z_L}{z_0}\right)\sin(\varphi_L)}\right)$$

where (subscript) 0: progress medium, B: obstacle, L: ultrasonic transmitter.

In the ultrasonic transmission apparatus according to an embodiment of the present disclosure, a distance $d_0$ between the obstacle and the ultrasonic transmission member
satisfies following Equation (3), $$d_0 = \frac{\varphi_0}{k_0} = \frac{c_{p0}}{2\omega} L\chi(\alpha, \beta) \quad \text{Equation (3)}$$

$$\left(\text{here}, \chi(\alpha, \beta) \equiv R_B\left(R_L - \frac{T_L^2}{R_L}\right),\right.$$

$$R_B = \frac{-\frac{i}{2}\left(\frac{z_0}{z_B} - \frac{z_B}{z_0}\right)\sin(\varphi_B)}{\cos(\varphi_B) + \frac{i}{2}\left(\frac{z_0}{z_B} + \frac{z_B}{z_0}\right)\sin(\varphi_B)},$$

$$R_L = \frac{-\frac{i}{2}\left(\frac{z_0}{z_L} - \frac{z_L}{z_0}\right)\sin(\varphi_L)}{\cos(\varphi_L) + \frac{i}{2}\left(\frac{z_0}{z_L} + \frac{z_L}{z_0}\right)\sin(\varphi_L)},$$

$$\left. T_L = \frac{1}{\cos(\varphi_L) + \frac{i}{2}\left(\frac{z_0}{z_L} + \frac{z_L}{z_0}\right)\sin(\varphi_L)}\right)$$

where (subscript) 0: progress medium, B: obstacle, L: ultrasonic transmitter.

In the ultrasonic transmission apparatus according to an embodiment of the present disclosure,
the ultrasonic transmission member satisfies following Equation (4), $$\alpha=1 \text{ and } \beta=1 \quad \text{Equation (4)}$$

where (subscript) 0: progress medium, B: obstacle, L: ultrasonic transmitter.

In the ultrasonic transmission apparatus according to an embodiment of the present disclosure,
the ultrasonic transmission member
selectively varies impedance and a phase, and
a distance $d_0$ between the obstacle and the ultrasonic transmission member satisfies following Equation (5) and Equation (6), $$\frac{c_{p0}}{2\omega} L\chi(\alpha, \beta) - \eta_{EPMC} \leq d_0 \leq \frac{c_{p0}}{2\omega} L\chi(\alpha, \beta) + \eta_{EPMC}, \quad \text{Equation (5)}$$

$$\eta_{EPMC} = 0.655 \times (1 - |R_B|) \quad \text{Equation (6)}$$

$$\left(\text{here}, \chi(\alpha, \beta) \equiv R_B\left(R_L - \frac{T_L^2}{R_L}\right),\right.$$

$$R_B = \frac{-\frac{i}{2}\left(\frac{z_0}{z_B} - \frac{z_B}{z_0}\right)\sin(\varphi_B)}{\cos(\varphi_B) + \frac{i}{2}\left(\frac{z_0}{z_B} + \frac{z_B}{z_0}\right)\sin(\varphi_B)},$$

$$R_L = \frac{-\frac{i}{2}\left(\frac{z_0}{z_L} - \frac{z_L}{z_0}\right)\sin(\varphi_L)}{\cos(\varphi_L) + \frac{i}{2}\left(\frac{z_0}{z_L} + \frac{z_L}{z_0}\right)\sin(\varphi_L)},$$

$$\left. T_L = \frac{1}{\cos(\varphi_L) + \frac{i}{2}\left(\frac{z_0}{z_L} + \frac{z_L}{z_0}\right)\sin(\varphi_L)}\right)$$

where (subscript) 0: progress medium, B: obstacle, L: ultrasonic transmitter.

In the ultrasonic transmission apparatus according to an embodiment of the present disclosure,
in the ultrasonic transmission member,
when a distance $d_0$ between the obstacle and the ultrasonic transmission member satisfies following Equation (3), the ration $\alpha$ and the ratio $\beta$ have values that satisfy following Equation (7) to Equation (9), $$d_0 = \frac{\varphi_0}{k_0} = \frac{c_{p0}}{2\omega} L\chi(\alpha, \beta), \quad \text{Equation (3)}$$

$$\eta_{EMMC1} \leq |\chi(\alpha, \beta)| \leq \eta_{EMMC2}, \quad \text{Equation (7)}$$

$$\eta_{EMMC1} = 1 - 7.0 \times (1 - |R_B|), \quad \text{Equation (8)}$$

$$\eta_{EMMC2} = 1 + 0.85 \times (1 - |R_B|) \quad \text{Equation (9)}$$

$$\left(\text{here}, \chi(\alpha, \beta) \equiv R_B\left(R_L - \frac{T_L^2}{R_L}\right),\right.$$

$$R_B = \frac{-\frac{i}{2}\left(\frac{z_0}{z_B} - \frac{z_B}{z_0}\right)\sin(\varphi_B)}{\cos(\varphi_B) + \frac{i}{2}\left(\frac{z_0}{z_B} + \frac{z_B}{z_0}\right)\sin(\varphi_B)},$$

$$R_L = \frac{-\frac{i}{2}\left(\frac{z_0}{z_L} - \frac{z_L}{z_0}\right)\sin(\varphi_L)}{\cos(\varphi_L) + \frac{i}{2}\left(\frac{z_0}{z_L} + \frac{z_L}{z_0}\right)\sin(\varphi_L)},$$

$$\left. T_L = \frac{1}{\cos(\varphi_L) + \frac{i}{2}\left(\frac{z_0}{z_L} + \frac{z_L}{z_0}\right)\sin(\varphi_L)}\right)$$

where (subscript) 0: progress medium, B: obstacle, L: ultrasonic transmitter.

In the ultrasonic transmission apparatus according to an embodiment of the present disclosure,
in the ultrasonic transmission member,
a distance $d_0$ between the obstacle and the ultrasonic transmission member satisfies following Equation (5) and Equation (6), and
the ratio $\alpha$ and the ratio $\beta$ have values that satisfy following Equation (7) to Equation (9) when the distance $d_0$ between the obstacle and the ultrasonic transmission member satisfies following Equation (3), $$\frac{c_{p0}}{2\omega} L\chi(\alpha, \beta) - \eta_{EPMC} \leq d_0 \leq \frac{c_{p0}}{2\omega} L\chi(\alpha, \beta) + \eta_{EPMC}, \quad \text{Equation (5)}$$

$$\eta_{EPMC} = 0.655 \times (1 - |R_B|), \quad \text{Equation (6)}$$

$$d_0 = \frac{\varphi_0}{k_0} = \frac{c_{p0}}{2\omega} L\chi(\alpha, \beta), \quad \text{Equation (3)}$$

$$\eta_{EMMC1} \leq |\chi(\alpha, \beta)| \leq \eta_{EMMC2}, \quad \text{Equation (7)}$$

$$\eta_{EMMC1} = 1 - 7.0 \times (1 - |R_B|), \quad \text{Equation (8)}$$

$$\eta_{EMMC2} = 1 + 0.85 \times (1 - |R_B|) \quad \text{Equation (9)}$$

$$\left(\text{here}, \chi(\alpha, \beta) \equiv R_B\left(R_L - \frac{T_L^2}{R_L}\right),\right.$$

$$R_B = \frac{-\frac{i}{2}\left(\frac{z_0}{z_B} - \frac{z_B}{z_0}\right)\sin(\varphi_B)}{\cos(\varphi_B) + \frac{i}{2}\left(\frac{z_0}{z_B} + \frac{z_B}{z_0}\right)\sin(\varphi_B)},$$

$$R_L = \frac{-\frac{i}{2}\left(\frac{z_0}{z_L} - \frac{z_L}{z_0}\right)\sin(\varphi_L)}{\cos(\varphi_L) + \frac{i}{2}\left(\frac{z_0}{z_L} + \frac{z_L}{z_0}\right)\sin(\varphi_L)},$$

$$\left. T_L = \frac{1}{\cos(\varphi_L) + \frac{i}{2}\left(\frac{z_0}{z_L} + \frac{z_L}{z_0}\right)\sin(\varphi_L)}\right)$$

where (subscript) 0: progress medium, B: obstacle, L: ultrasonic transmitter.

A wave control method according to an embodiment of the present disclosure includes varying a distance between an ultrasonic transmission member and an obstacle and a material of the ultrasonic transmission member in a state in which the ultrasonic transmission member is between an ultrasonic generation member and an obstacle; and transferring an ultrasonic wave generated by the ultrasonic generation member across the obstacle.

In the wave control method according to an embodiment of the present disclosure, a ratio $\alpha$ between a phase of the obstacle and a phase of the ultrasonic transmission member and a ratio $\beta$ between impedance of the obstacle and impedance of the ultrasonic transmission member are defined according to following Equation (1), $$\alpha \equiv \frac{\varphi_L}{\varphi_B} = \frac{k_L d_L}{k_B d_B}, \beta \equiv \frac{z_L}{z_B} \qquad \text{Equation (1)}$$

where $z = \rho c$ ($\rho$: density c: wave velocity)
$\Phi = kd$ (k: wavenumber, d: thickness of dissimilar material)
$k = \omega/c = $ ($\omega$: frequency [Rad/s])
$\omega = 2\pi f$ (f: frequency [Hz]))
(subscript) 0: progress medium, B: obstacle, L: ultrasonic transmitter.

In the wave control method according to an embodiment of the present disclosure, the ratio $\beta$ between the impedance of the obstacle and the impedance of the ultrasonic transmission member and the ratio $\alpha$ between the phase of the obstacle and the phase of the ultrasonic transmission member each satisfy following Equation (2), $$1 = |\chi(\alpha, \beta)| \qquad \text{Equation (2)}$$

$$\left(\text{here}, \chi(\alpha, \beta) \equiv R_B\left(R_L - \frac{T_L^2}{R_L}\right),\right.$$

$$R_B = \frac{-\frac{i}{2}\left(\frac{z_0}{z_B} - \frac{z_B}{z_0}\right)\sin(\varphi_B)}{\cos(\varphi_B) + \frac{i}{2}\left(\frac{z_0}{z_B} + \frac{z_B}{z_0}\right)\sin(\varphi_B)},$$

$$R_L = \frac{-\frac{i}{2}\left(\frac{z_0}{z_L} - \frac{z_L}{z_0}\right)\sin(\varphi_L)}{\cos(\varphi_L) + \frac{i}{2}\left(\frac{z_0}{z_L} + \frac{z_L}{z_0}\right)\sin(\varphi_L)},$$

$$\left.T_L = \frac{1}{\cos(\varphi_L) + \frac{i}{2}\left(\frac{z_0}{z_L} + \frac{z_L}{z_0}\right)\sin(\varphi_L)}\right)$$

where (subscript) 0: progress medium, B: obstacle, L: ultrasonic transmitter.

In the wave control method according to an embodiment of the present disclosure, a distance $d_0$ between the obstacle and the ultrasonic transmission member satisfies following Equation (3), $$d_0 = \frac{\varphi_0}{k_0} = \frac{c_{p0}}{2\omega} L\chi(\alpha, \beta) \qquad \text{Equation (3)}$$

$$\left(\text{here}, \chi(\alpha, \beta) \equiv R_B\left(R_L - \frac{T_L^2}{R_L}\right),\right.$$

$$R_B = \frac{-\frac{i}{2}\left(\frac{z_0}{z_B} - \frac{z_B}{z_0}\right)\sin(\varphi_B)}{\cos(\varphi_B) + \frac{i}{2}\left(\frac{z_0}{z_B} + \frac{z_B}{z_0}\right)\sin(\varphi_B)},$$

$$R_L = \frac{-\frac{i}{2}\left(\frac{z_0}{z_L} - \frac{z_L}{z_0}\right)\sin(\varphi_L)}{\cos(\varphi_L) + \frac{i}{2}\left(\frac{z_0}{z_L} + \frac{z_L}{z_0}\right)\sin(\varphi_L)},$$

$$\left.T_L = \frac{1}{\cos(\varphi_L) + \frac{i}{2}\left(\frac{z_0}{z_L} + \frac{z_L}{z_0}\right)\sin(\varphi_L)}\right)$$

In the wave control method according to an embodiment of the present disclosure, the ultrasonic transmission member satisfies following Equation (4), $$\alpha = 1 \text{ and } \beta = 1 \qquad \text{Equation (4)}$$

where (subscript) 0: progress medium, B: obstacle, L: ultrasonic transmitter.

In the wave control method according to an embodiment of the present disclosure, a distance $d_0$ between the obstacle and the ultrasonic transmission member satisfies following Equation (5) and Equation (6), $$\frac{c_{p0}}{2\omega} LX(\alpha, \beta) - \eta_{EPMC} \le d_0 \le \frac{c_{p0}}{2\omega} LX(\alpha, \beta) + \eta_{EPMC}, \qquad \text{Equation (5)}$$

$$\eta_{EPMC} = 0.655 \times (1 - |R_B|) \qquad \text{Equation (6)}$$

$$\left(\text{here}, X(\alpha, \beta) \equiv R_B\left(R_L - \frac{T_L^2}{R_L}\right),\right.$$

$$R_B = \frac{-\frac{i}{2}\left(\frac{z_0}{z_B} - \frac{z_B}{z_0}\right)\sin(\varphi_B)}{\cos(\varphi_B) + \frac{i}{2}\left(\frac{z_0}{z_B} + \frac{z_B}{z_0}\right)\sin(\varphi_B)},$$

$$R_L = \frac{-\frac{i}{2}\left(\frac{z_0}{z_L} - \frac{z_L}{z_0}\right)\sin(\varphi_L)}{\cos(\varphi_L) + \frac{i}{2}\left(\frac{z_0}{z_L} + \frac{z_L}{z_0}\right)\sin(\varphi_L)},$$

$$\left.T_L = \frac{1}{\cos(\varphi_L) + \frac{i}{2}\left(\frac{z_0}{z_L} + \frac{z_L}{z_0}\right)\sin(\varphi_L)}\right)$$

where (subscript) 0: progress medium, B: obstacle, L: ultrasonic transmitter.

In the wave control method according to an embodiment of the present disclosure, when a distance $d_0$ between the obstacle and the ultrasonic transmission member satisfies following Equation (3), the ration $\alpha$ and the ratio $\beta$ have values that satisfy following Equation (7) to Equation (9), $$d_0 = \frac{\varphi_0}{k_0} = \frac{c_{p0}}{2\omega} LX(\alpha, \beta), \qquad \text{Equation (3)}$$

$$\eta_{EMMC1} \le |X(\alpha, \beta)| \le \eta_{EMMC2}, \qquad \text{Equation (7)}$$

$$\eta_{EMMC1} = 1 - 7.0 \times (1 - |R_B|), \qquad \text{Equation (8)}$$

$$\eta_{EMMC2} = 1 + 0.85 \times (1 - |R_B|) \qquad \text{Equation (9)}$$

$$\left(\text{here, } \chi(\alpha, \beta) \equiv R_B\left(R_L - \frac{T_L^2}{R_L}\right),\right.$$

$$R_B = \frac{-\frac{i}{2}\left(\frac{z_0}{z_B} - \frac{z_B}{z_0}\right)\sin(\varphi_B)}{\cos(\varphi_B) + \frac{i}{2}\left(\frac{z_0}{z_B} + \frac{z_B}{z_0}\right)\sin(\varphi_B)},$$

$$R_L = \frac{-\frac{i}{2}\left(\frac{z_0}{z_L} - \frac{z_L}{z_0}\right)\sin(\varphi_L)}{\cos(\varphi_L) + \frac{i}{2}\left(\frac{z_0}{z_L} + \frac{z_L}{z_0}\right)\sin(\varphi_L)},$$

$$T_L = \frac{1}{\cos(\varphi_L) + \frac{i}{2}\left(\frac{z_0}{z_L} + \frac{z_L}{z_0}\right)\sin(\varphi_L)}\Bigg)$$

where (subscript) 0: progress medium, B: obstacle, L: ultrasonic transmitter.

In the wave control method according to an embodiment of the present disclosure, a distance $d_0$ between the obstacle and the ultrasonic transmission member satisfies following Equation (5) and Equation (6), and the ratio α and the ratio β have values that satisfy following Equation (7) to Equation (9) when the distance $d_0$ between the obstacle and the ultrasonic transmission member satisfies following Equation (3), $$\frac{c_{p0}}{2\omega}LX(\alpha, \beta) - \eta_{EPMC} \le d_0 \le \frac{c_{p0}}{2\omega}LX(\alpha, \beta) + \eta_{EPMC}, \quad \text{Equation (5)}$$

$$\eta_{EPMC} = 0.655 \times (1 - |R_B|), \quad \text{Equation (6)}$$

$$d_0 = \frac{\varphi_0}{k_0} = \frac{c_{p0}}{2\omega}LX(\alpha, \beta), \quad \text{Equation (3)}$$

$$\eta_{EMMC1} \le |X(\alpha, \beta)| \le \eta_{EMMC2}, \quad \text{Equation (7)}$$

$$\eta_{EMMC1} = 1 - 7.0 \times (1 - |R_B|), \quad \text{Equation (8)}$$

$$\eta_{EMMC2} = 1 + 0.85 \times (1 - |R_B|) \quad \text{Equation (9)}$$

$$\left(\text{here, } \chi(\alpha, \beta) \equiv R_B\left(R_L - \frac{T_L^2}{R_L}\right),\right.$$

$$R_B = \frac{-\frac{i}{2}\left(\frac{z_0}{z_B} - \frac{z_B}{z_0}\right)\sin(\varphi_B)}{\cos(\varphi_B) + \frac{i}{2}\left(\frac{z_0}{z_B} + \frac{z_B}{z_0}\right)\sin(\varphi_B)},$$

$$R_L = \frac{-\frac{i}{2}\left(\frac{z_0}{z_L} - \frac{z_L}{z_0}\right)\sin(\varphi_L)}{\cos(\varphi_L) + \frac{i}{2}\left(\frac{z_0}{z_L} + \frac{z_L}{z_0}\right)\sin(\varphi_L)},$$

$$T_L = \frac{1}{\cos(\varphi_L) + \frac{i}{2}\left(\frac{z_0}{z_L} + \frac{z_L}{z_0}\right)\sin(\varphi_L)}\Bigg)$$

where (subscript) 0: progress medium, B: obstacle, L: ultrasonic transmitter.

Advantageous Effects of Disclosure

According to an ultrasonic transmission apparatus and a wave control method according to the present disclosure, an ultrasonic transmission member is located at a predetermined distance in front of an obstacle. In addition, high ultrasonic energy may be transferred across an obstacle due to a resonance phenomenon between the obstacle and an ultrasonic transmission member.

According to an ultrasonic transmission apparatus and a wave control method according to the present disclosure, it is possible to transmit very high ultrasonic energy (maximum 100%) at a desirable frequency regardless of a type and a thickness of an obstacle.

An ultrasonic transmission apparatus and a wave control method according to the present disclosure may be widely used in underwater ultrasonic waves, acoustics, medical ultrasonic waves, and a non-destructive inspection.

BEST MODE

An ultrasonic transmission apparatus according an embodiment of the present disclosure is an ultrasonic transmission apparatus for performing an ultrasonic inspection by injecting an ultrasonic wave into an object including a medium and a body to be inspected inside and including an obstacle outside, and includes an ultrasonic generation device configured to generate an incident wave; and an ultrasonic transmission module located between the obstacle and the ultrasonic generation device and located on a travel path of an incident wave generated by the ultrasonic generation device, wherein the ultrasonic transmission module includes an ultrasonic transmission member, and a position variable device configured to vary a position of the ultrasonic transmission member.

MODE OF DISCLOSURE

Hereinafter, the present disclosure will be described in more detail with reference to the accompanying drawings according to embodiments of the present disclosure. First, a wave control method according to an embodiment of the present disclosure will be described, and then a specific embodiment of the present disclosure will be described based on the wave control method.

1. Wave Control Method According to Embodiment of Present Disclosure

<Ultrasonic Wave Transmission Equation when there is Obstacle or Ultrasonic Transmission Member on Travel Path of Ultrasonic Wave>

Figure 1:
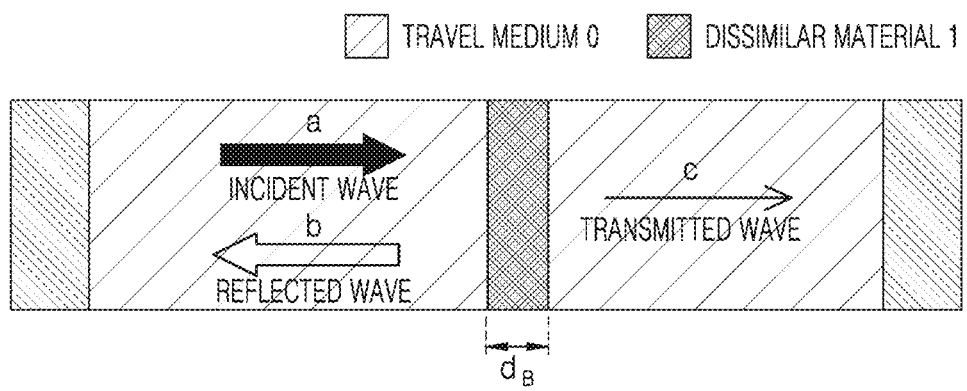
FIG. 1 illustrates an incident wave a, a reflected wave b, and a transmitted wave c when an ultrasonic wave incident on a medium encounters an obstacle which is formed of a dissimilar material B and has a thickness of dB.
Figure 2:
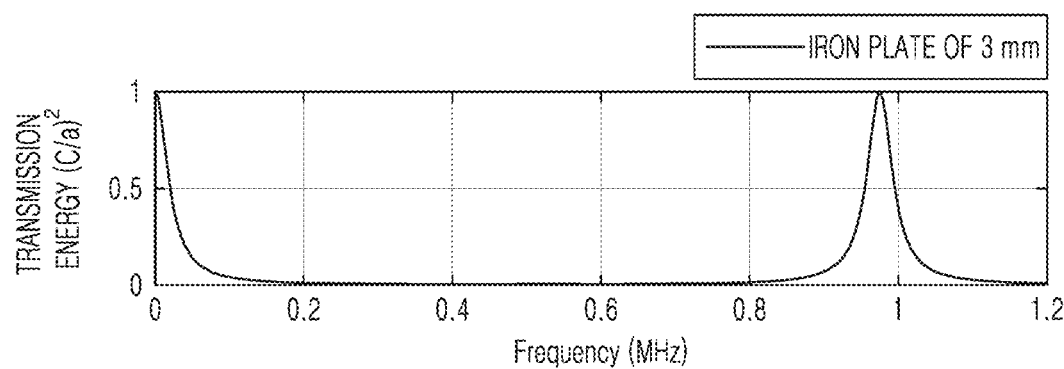
FIG. 2 illustrates a relationship between transmission energy and a frequency.

FIG. 1 illustrates an incident wave a, a reflected wave b, and a transmitted wave c when an ultrasonic wave incident on a medium encounters an obstacle which is formed of a dissimilar material B and has a thickness of $d_B$, and FIG. 2 illustrates a relationship between transmission energy and a frequency.

When an ultrasonic wave traveling through a medium encounters an obstacle, a transmission coefficient R and a reflection coefficient T of the ultrasonic wave are represented by following Equation (1).

$$R = \frac{b}{a} = \frac{-\frac{i}{2}\left(\frac{z_0}{z_B} - \frac{z_B}{z_0}\right)\sin\varphi_B}{\cos\varphi_B + \frac{i}{2}\left(\frac{z_0}{z_B} + \frac{z_B}{z_0}\right)\sin\varphi_B},$$

$$T = \frac{c}{a} = \frac{1}{\cos\varphi_B + \frac{i}{2}\left(\frac{z_0}{z_B} + \frac{z_B}{z_0}\right)\sin\varphi_B}$$

Equation (1)

Here, z is impedance and φ is a phase change of an ultrasonic wave travelling through a dissimilar material. A subscript O means a medium, and a subscript B means an obstacle. In addition, a detailed description on each variable is as follows.

z=ρc (ρ: density c: wave velocity)

Φ=kd (k: wavenumber, d: thickness of dissimilar material)

k=ω/c=(ω: frequency [Rad/s])

ω=2πf (f: frequency [Hz])

When an ultrasonic transmission member is placed instead of an obstacle, the obstacle is removed, and an ultrasonic wave passes through only the ultrasonic transmission member. Accordingly, the transmission coefficient R and the reflection coefficient T of the ultrasonic wave is represented by following Equation (2). The subscript B representing the obstacle of Equation (1) described above is changed to L representing an ultrasonic transmission member of Equation (2).

$$R_B = \frac{-\frac{i}{2}\left(\frac{z_0}{z_B} - \frac{z_B}{z_0}\right)\sin(\varphi_B)}{\cos(\varphi_B) + \frac{i}{2}\left(\frac{z_0}{z_B} + \frac{z_B}{z_0}\right)\sin(\varphi_B)},$$

$$R_L = \frac{-\frac{i}{2}\left(\frac{z_0}{z_L} - \frac{z_L}{z_0}\right)\sin(\varphi_L)}{\cos(\varphi_L) + \frac{i}{2}\left(\frac{z_0}{z_L} + \frac{z_L}{z_0}\right)\sin(\varphi_L)}$$

$$T_L = \frac{1}{\cos(\varphi_L) + \frac{i}{2}\left(\frac{z_0}{z_L} + \frac{z_L}{z_0}\right)\sin(\varphi_L)}$$

Equation (2)

That is, when there is only an obstacle or only an ultrasonic transmission member, the ultrasonic wave transmits through a single layer. Accordingly, an ultrasonic wave is only affected by a property of a single layer. In addition, when the ultrasonic wave passes through only the obstacle or the ultrasonic transmission member, equations for deriving the transmission coefficient and the reflection coefficient of the ultrasonic wave essentially have the same form as each other.

As illustrated in FIG. 2, transmission energy $(C/A)^2$ of an incident wave passing through an obstacle has a different value depending on a frequency of the incident wave. In the example of FIG. 2, an iron plate having a thickness of 3 mm is used.

<Ultrasonic Wave Transmission Equation when there are Ultrasonic Transmission Member and Obstacle>

Figure 3A:
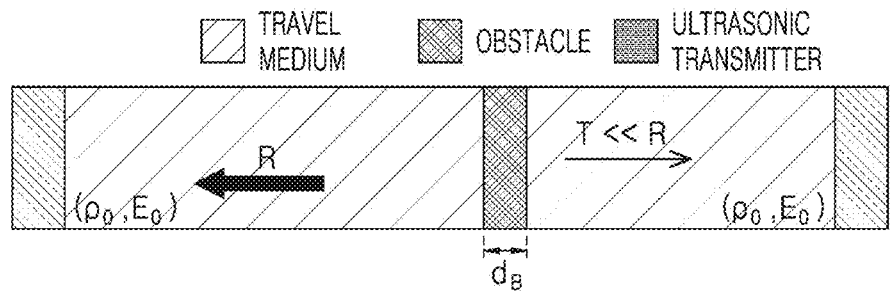
FIGS. 3A and 3B illustrate transmission and reflection of an incident ultrasonic wave when there are an ultrasonic transmission member and an obstacle.
Figure 3B:
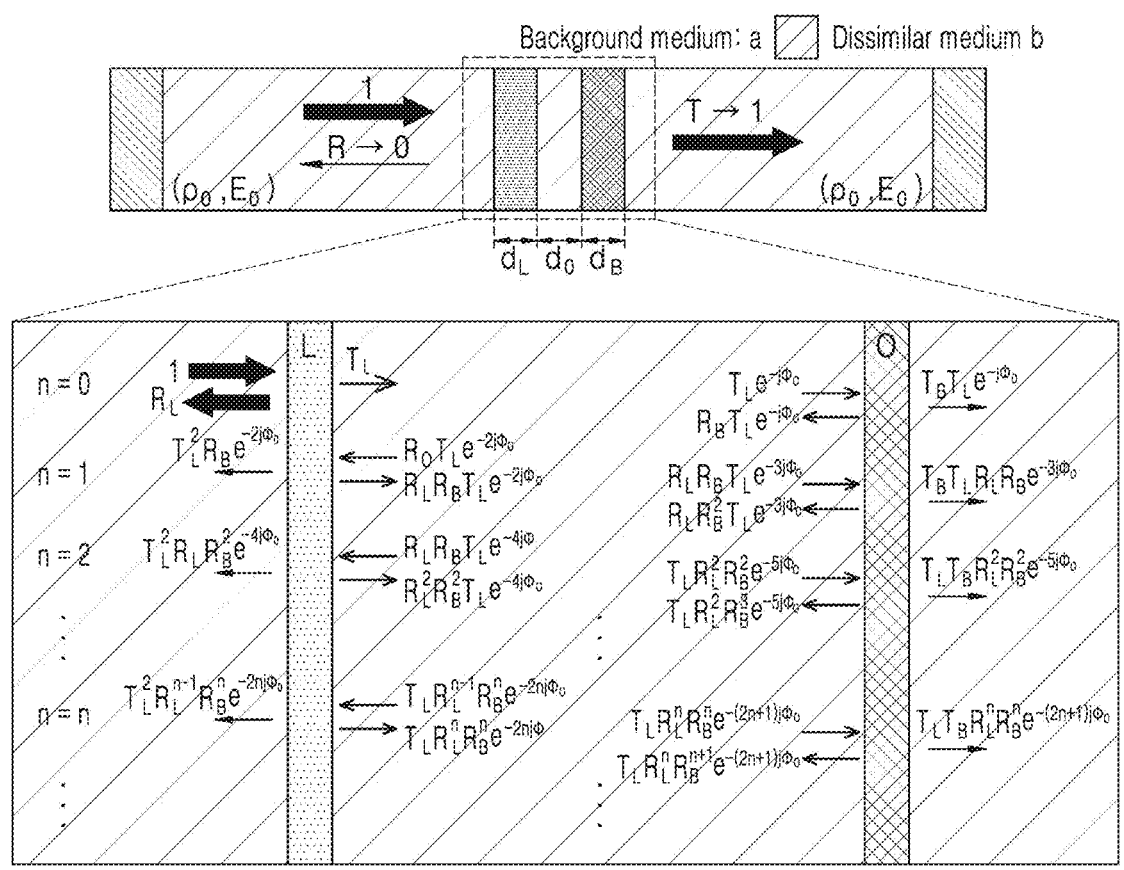

When there are an ultrasonic transmission member and an obstacle, a case in which an ultrasonic wave transmits through multiple layers may be simulated. This case may be illustrated in FIGS. 3A and 3B.

In this case, an ultrasonic wave is highly reflected from multiple layers including an obstacle and an ultrasonic transmission member.

A final transmittance T, and a reflectance R are the same as an infinite sum of ultrasonic waves reflected in the n-th order. When this may be represented by following Equation (3a) and Equation (3b).

$$R = R_L + \sum_{n=1}^{\infty} T_R^2 R_L^{n-1} R_B^n e^{-2nj\varphi_0} = \quad \text{Equation (3a)}$$

$$R_L + T_L^2 R_B e^{-2j\varphi_0} \sum_{n=1}^{\infty} R_L^{n-1} R_B^{n-1} e^{-2(n-1)j\varphi_0}$$

$$T = T_B T_L e^{-j\varphi_0} \lim_{n \to \infty} \frac{1 - R_L^n R_B^n e^{-2nj\varphi_0}}{1 - R_L^n R_B^n e^{-2j\varphi_0}} = \frac{T_B T_L e^{-j\varphi_0}}{1 - R_L R_B e^{-2j\varphi_0}} \quad \text{Equation (3b)}$$

$R_L$, $T_L$, $R_B$, and $T_B$ of Equation (3a) and Equation (3b) are the same as defined in Equation (1) and Equation (2).

Assuming complete transmission of an ultrasonic wave, R=0 and T=1. The two equations are the same as each other because the two equations have necessary and sufficient condition.

When the above equation is developed under the condition of R=0, the equation may be represented again as the following equation.

$$R_L(1-R_L R_B e^{-2j\varphi_0}) + T_L^2 R_B e^{-2j\varphi_0} = 0 \quad \text{Equation (4)}$$

Here, a term $e^{2j\varphi_0}$ indicating a phase $\varphi_0 = k_0 d_0$ in which a wave travels between an obstacle and an ultrasonic transmission member may be defined by the following equation. This process is as follows.

$$R_L(1 - R_L R_B e^{-2j\varphi_0}) + T_L^2 R_B e^{-2j\varphi_0} = 0$$

$$R_L - R_L R_L R_B e^{-2j\varphi_0} + T_L^2 R_B e^{-2j\varphi_0} = 0$$

$$R_L = R_L R_L R_B e^{-2j\varphi_0} - T_L^2 R_B e^{-2j\varphi_0}$$

$$R_L = R_B (R_L^2 - T_L^2) e^{-2j\varphi_0}$$

$$e^{2j\varphi_0} = \frac{R_B}{R_L}(R_L^2 - T_L^2)$$

$$e^{2j\varphi_0} = R_B \left( R_L - \frac{T_L^2}{R_L} \right)$$

Through the above process, following Equation (5) is derived.

$$e^{2j\varphi_0} = \chi(\alpha, \beta), \chi(\alpha, \beta) \equiv R_B \left( R_L - \frac{T_L^2}{R_L} \right) \quad \text{Equation (5)}$$

Equation (5) may be further described as follows.

Characteristics of a system that determines propagation characteristics of an ultrasonic wave include impedance z and phase (I).

At this time, the characteristics z of an ultrasonic transmission member may be represented as relative values with respect to characteristics of a given obstacle. For example, impedance of the ultrasonic transmission member is twice impedance of the obstacle, and a phase of the ultrasonic transmission member is 0.8 times a phase of the obstacle. This may be mathematically represented as following Equation (6).

$$\alpha \equiv \frac{\varphi_L}{\varphi_B} = \frac{k_L d_L}{k_B d_B}, \beta \equiv \frac{z_L}{z_B} \quad \text{Equation (6)}$$

Here, $k_B$, $k_L$, and $k_0$ are wavenumbers of an obstacle, an ultrasonic transmission member, and a travel medium, respectively. In addition, $z_B$, $z_L$, and $z_0$ indicate impedances of an obstacle, an ultrasonic transmission member, and a traveling medium, respectively.

As represented by the above equation, a ratio between a phase of the ultrasonic transmission member and a phase of the obstacle is denoted by a. In addition, a ratio between the impedance of the ultrasonic transmission member to the impedance of the obstacle is denoted by β.

As described above, a function described in Equation (5) may be represented in the form of functions of α and β. That is, the function may be represented as $\chi(\alpha, \beta)$.

<Phase Matching and Magnitude Matching>

Both the left and the right of Equation (5) are $e^{2j\varphi_0}$ and $\chi(\alpha,\beta)$, respectively, which are complex numbers.

Because Equation (5) is derived from R=0, Equation (5) and R=0 are necessary and sufficient conditions. That is, in order for Equation (5) to be valid, the two complex numbers of $e^{2j\varphi_0}$ and $\chi(\alpha, \beta)$ have to be the same as each other. Accordingly, when R=0, the two complex numbers of $e^{2j\varphi_0}$ and $\chi(\alpha, \beta)$ are the same as each other.

That is, when the two complex numbers of $e^{2j\varphi_0}$ and $\chi(\alpha, \beta)$ match each other, R=0, and a reflected wave of an ultrasonic wave becomes zero. Accordingly, the ultrasonic wave performs complete transmission.

Here, the matching of the complex numbers means that phases and magnitudes of the two complex numbers match each other. That is, A=B, which is a matching condition of the two complex numbers of A and B, is described as a condition in which the phases and the magnitudes match each other as follows.

∠A=∠B (Phase matching condition (PMC))

|A|=|B| (Magnitude matching condition (MMC))

The same is applied to a case of Equation (5).

First, a phase matching condition indicating that phases match each other is represented by following Equation (A3.1).

$$\angle e^{2j\varphi_0} = 2\varphi_0 \text{ and } 2\varphi_0 = \angle\chi(\alpha,\beta) \quad \text{Equation (A3.1)}$$

Equation (A3.1) is changed into an equation for a distance $d_0$. This process is as follows.

First, $\varphi_0$ is represented as follows.

$$\varphi_0 = k_0 d_0 \text{ } (k\text{: wavenumber, } d\text{: distance}) \quad \text{Equation (A3.2)}$$

Here, $k_0$ has a following relationship with an angular frequency and a travel speed $c_{p0}$ of a wave.

$$\omega = c_{p0} k_0 \text{ or } k_0 = \omega/c_{p0} \quad \text{Equation (A3.3)}$$

Finally, Equation (A3.1), Equation (A3.2), and Equation (A3.3) are summarized as follows.

$$2\varphi_0 = \angle\chi(\alpha, \beta)$$

$$\varphi_0 = \frac{1}{2}\angle\chi(\alpha, \beta)$$

$$k_0 d_0 = \frac{1}{2}\angle\chi(\alpha, \beta)$$

$$\frac{\omega}{c_{p0}} d_0 = \frac{1}{2}\angle\chi(\alpha, \beta)$$

As a result, above equations become following Equation (7).

$$d_0 = \frac{\varphi_0}{k_0} = \frac{c_{p0}}{2\omega} \angle X(\alpha, \beta) \quad \text{Equation (7)}$$

Subsequently, a magnitude matching condition indicating that magnitudes match each other is as follows. The magnitude matching condition indicates that magnitudes of two complex numbers are the same as each other.

When the above condition is applied to Equation (5) described above, following Equation (A4.1) is established.

$$|e^{2j\varphi_0}| = |\chi(\alpha, \beta)| \quad \text{Equation (A4.1)}$$

According to De Moivre's theorem ($e^{j\theta} = \cos \theta + i \sin \theta$), the magnitude becomes 1 as follows.

$$|e^{j\theta}| = |\cos \theta + i \sin \theta| = \sqrt{\cos^2\theta + \sin^2\theta} = 1 \quad \text{Equation (A4.2)}$$

According to De Moivre's theorem, the left becomes $|e^{2j\varphi_0}| = 1$.

Accordingly, following Equation (8) is finally derived.

$$1 = |\chi(\alpha, \beta)| \quad \text{Equation (8)}$$

<Consideration on Phase Matching Condition>

A phase matching condition may be constantly obtained by adjusting the distance do between an ultrasonic transmission member and an obstacle, irrespective of characteristics (phase and impedance) of the ultrasonic transmission member and the obstacle.

When phases and impedances of the ultrasonic transmission member and the obstacle are given, a distance at which a maximum transmittance is achieved may be selected by Equation (7). That is, a maximum transmittance may be obtained by varying a position of the ultrasonic transmission member (that is, by varying a distance between the ultrasonic transmission member and the obstacle).

FIGS. 4A to 4F illustrate examples in which various ultrasonic transmission members are applied to a given obstacle. In FIGS. 4A to 4F, a travel medium is water, and the obstacle is an iron plate having a thickness of 3 mm.

Figure 4A:
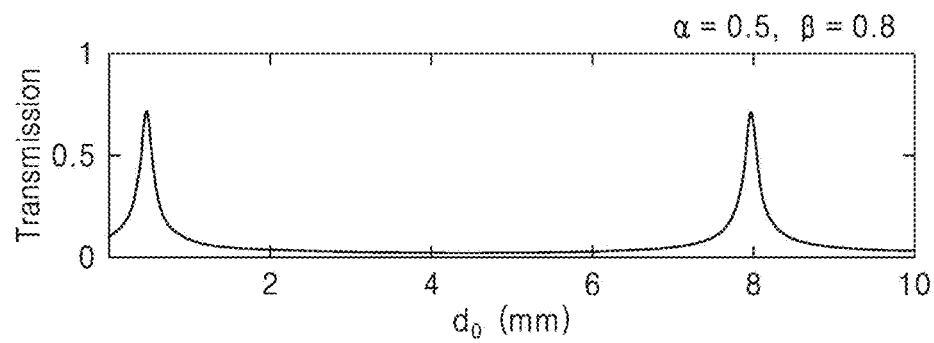
FIGS. 4A to 4F illustrate examples in which various ultrasonic transmission members are applied to a given obstacle.
Figure 4B:
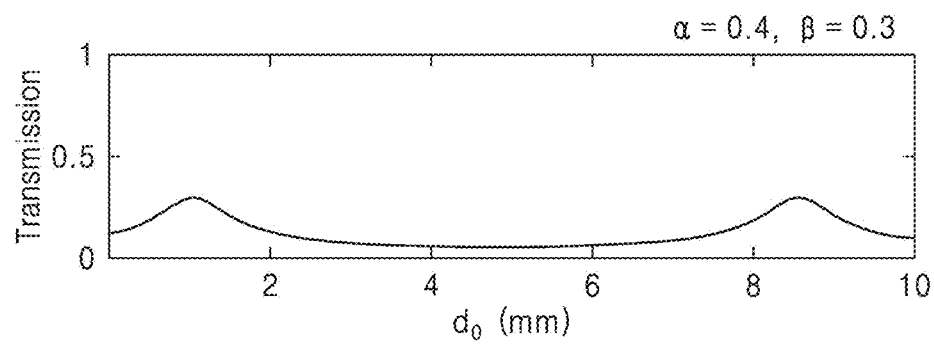
Figure 4C:
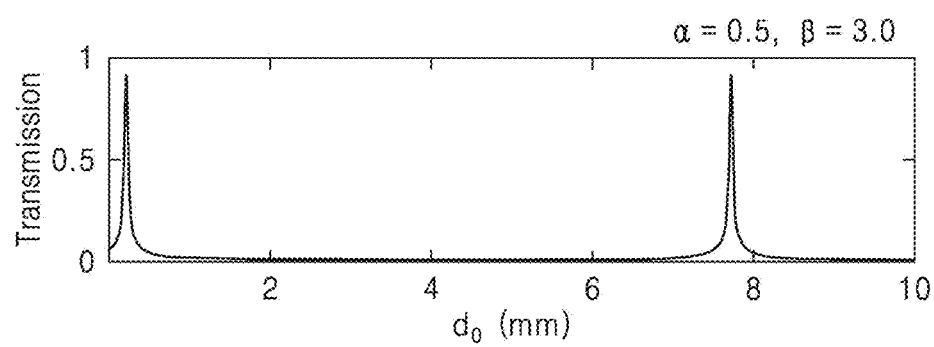
Figure 4D:
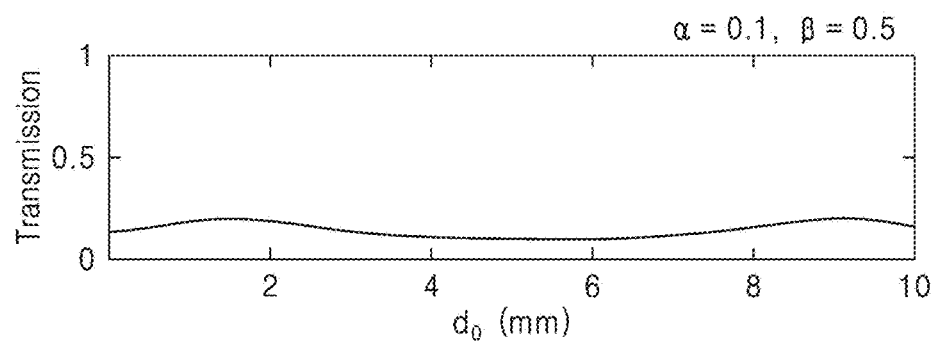
Figure 4E:
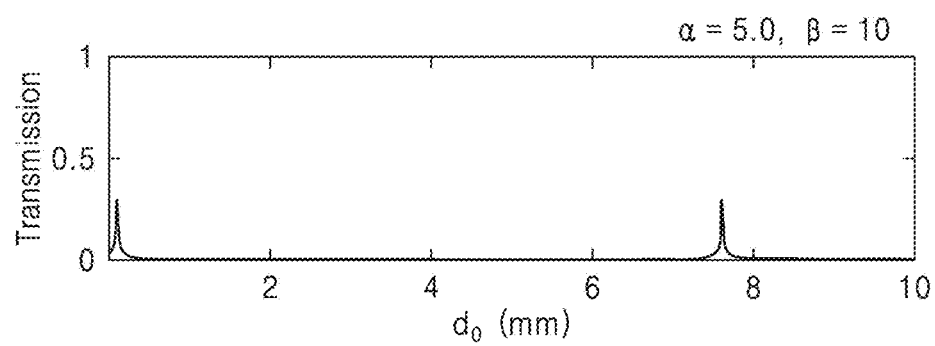
Figure 4F:
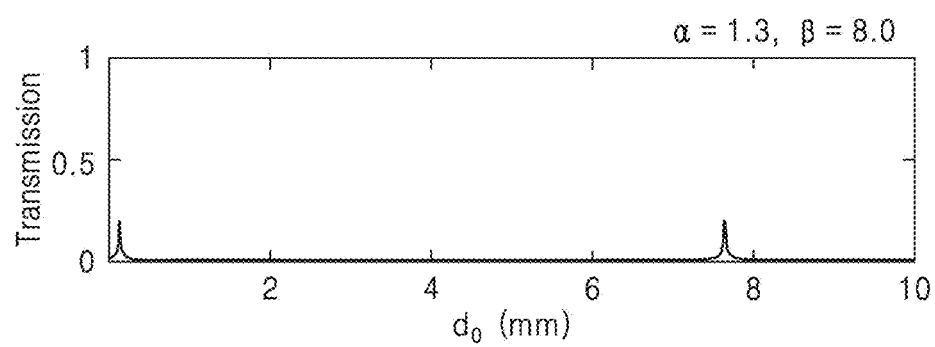

For example, in a case in which $\alpha=0.5$ and $\beta=0.8$ in FIG. 4A, when a distance between the ultrasonic transmission member and the obstacle is approximately 8 mm, a maximum transmittance is obtained. As another example, in a case in which $\alpha=0.5$ and $\beta=3.0$, when the distance between the ultrasonic transmission member and the obstacle is approximately 7.8 mm, the maximum transmittance is obtained.

As illustrated in FIGS. 4A to 4F, it can be seen that the maximum transmittance may be obtained by adjusting the distance between the ultrasonic transmission member and the obstacle.

<Consideration on Magnitude Matching Condition>

Referring to the above description and drawings, it can be seen that, when various ultrasonic transmission members are applied to a given obstacle, high transmittance is obtained by an ultrasonic transmission member having specific characteristics. In the given conditions, a transmittance of an obstacle is 12.7%. The distance $d_0$ at this time follows the phase matching condition of Equation (7).

However, it can be seen that, even when a maximum value (called a partial maximum value) of the transmittance is adjusted by adjusting a distance between an ultrasonic transmission member and an obstacle, there are many cases in which the maximum value is not 1 (100%). For example, considering FIGS. 4A to 4F, it can be seen that the partial maximum value is achieved in the specific distance $d_0$ in each case and magnitudes are different from each other. Accordingly, it can be seen that the maximum transmittance may be obtained only when a condition for maximizing the partial maximum value is satisfied.

As described above, the condition for maximizing the partial maximum value is the magnitude matching condition.

The left of Equation (5), which is $$X(\alpha, \beta) \equiv R_B\left(R_L - \frac{T_L^2}{R_L}\right),$$

is determined only by characteristics (impedance and phase) of a frequency, an obstacle, and an ultrasonic transmission member.

That is, the magnitude matching condition of Equation (8) may not be satisfied according to the characteristics $\alpha$ and $\beta$ of the given obstacle and the selected ultrasonic transmission member. Accordingly, it is necessary to select characteristics of the ultrasonic transmission member that satisfy Equation (8).

A maximum value of a transmittance in which a phase matching condition is satisfied (a partial maximum value attainment condition is satisfied) is determined by a physical property of an ultrasonic transmission member. When the physical property of the ultrasonic transmission member is a specific value, the maximum value of the transmittance satisfying a phase matching condition may be 100%. In this way, when the maximum value of the transmittance is 100%, it can be said that the ultrasonic transmission member satisfies a magnitude matching condition.

That is, it can be said that the magnitude matching condition deals with a problem of how to determine a physical property of the ultrasonic transmission member such that a maximum transmittance value matching the phase matching condition may become 100%.

Figure 5A:
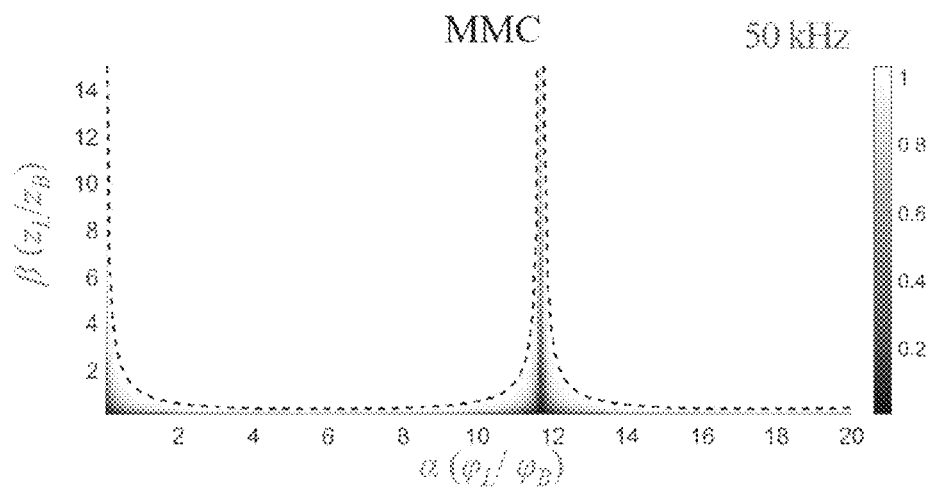
FIGS. 5A to 5C illustrate magnitude matching conditions according to characteristics α and β of various ultrasonic transmission members.
Figure 5B:
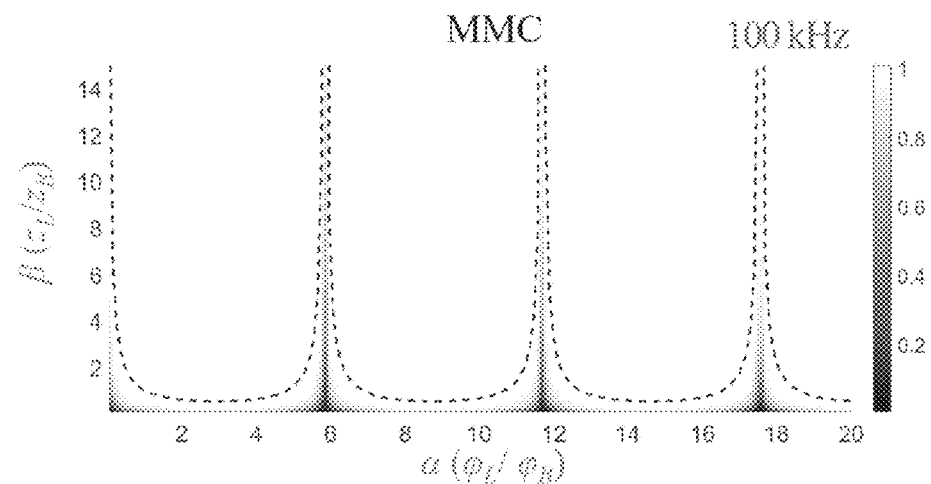
Figure 5C:
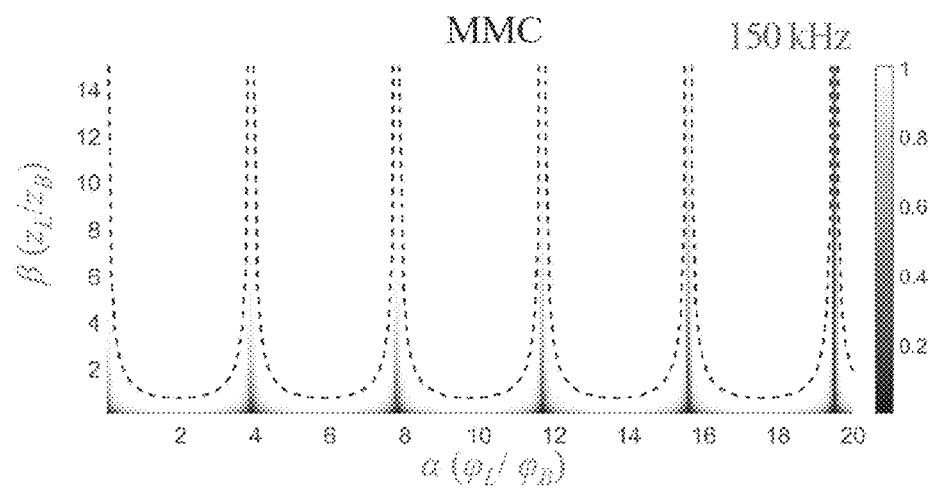

Magnitude matching conditions for the characteristics $\alpha$ and $\beta$ of various ultrasonic transmitters are illustrated in FIGS. 5A to 5C.

In FIGS. 5A to 5C, a line that satisfies a condition of $1 = |\chi(\alpha, \beta)|$, that is, the magnitude matching condition (MMC), is indicated by a dotted line. Accordingly, it is sufficient to select a property of an ultrasonic transmission member along the marked line. Because a satisfaction point changes depending on a frequency, the satisfaction point has to be selected according to a desirable frequency.

Figure 6A:
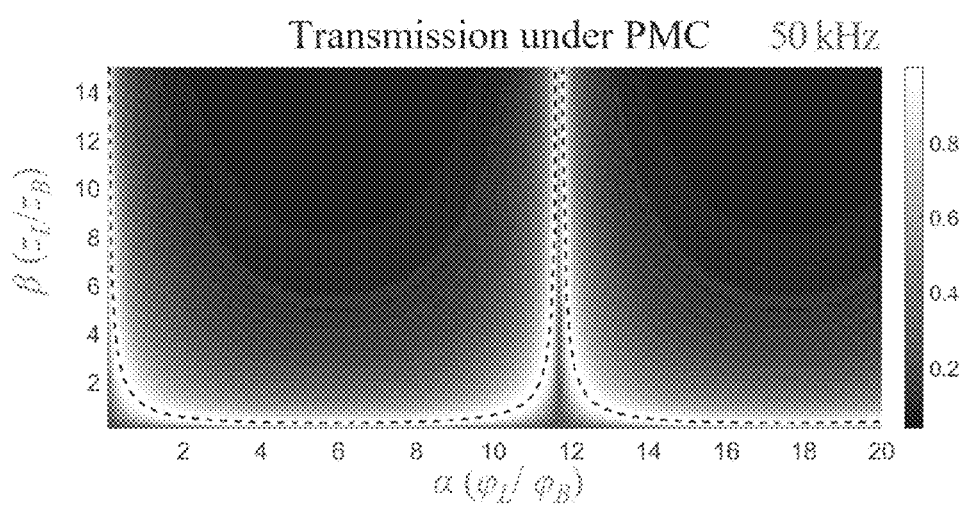
FIGS. 6A to 6C illustrate phase matching conditions according to the characteristics α and β of the various ultrasonic transmission members.
Figure 6B:
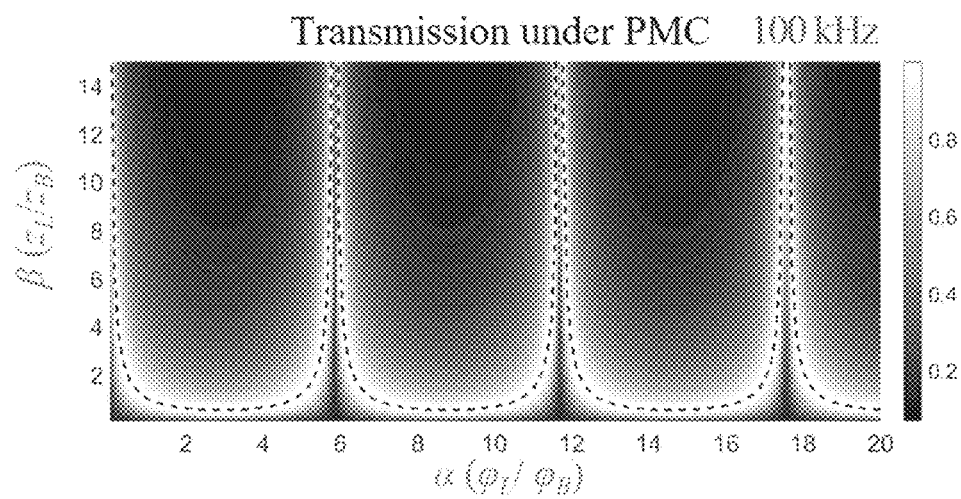
Figure 6C:
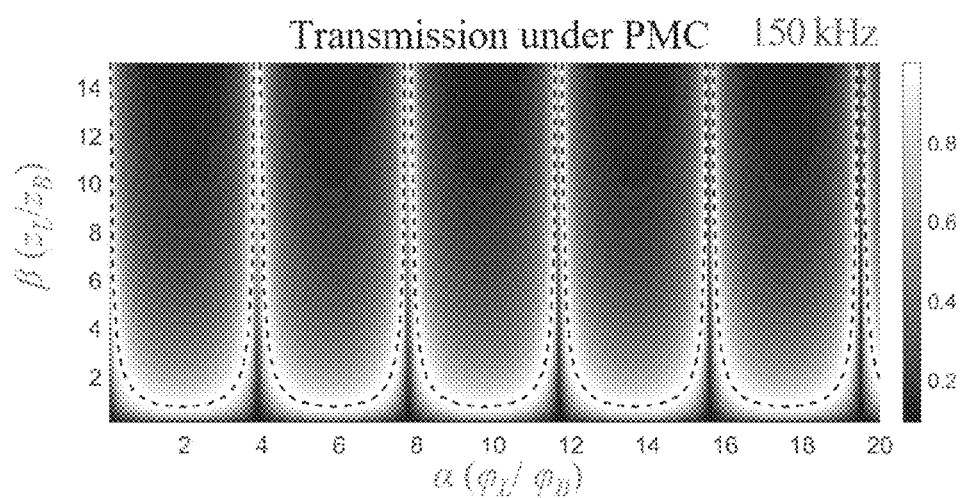

FIGS. 6A to 6C are views illustrating a transmittance in terms of the characteristics $\alpha$ and $\beta$ of the ultrasonic transmission member under the phase matching condition. In FIGS. 6A to 6C, conditions illustrating a transmittance of 100% are indicated by a dotted line. Comparing FIGS. 6A to 6C with FIGS. 5A to 5C, it can be seen that the portion satisfying the magnitude matching condition (MMC) of FIGS. 5A to 5C (dotted line) and the portion illustrating a transmittance of 100% of FIGS. 6A to 6C match each other. That is, as illustrated in FIGS. 6A to 6C, it can be seen that the transmittance of 100% is illustrated on a line in which the magnitude matching condition of FIGS. 5A to 5C is satisfied.

<Consideration on Additional Condition>

When an ultrasonic transmission member that satisfies the magnitude matching condition is selected to be installed at the distance $d_0$ that satisfies the phase matching condition, an ultrasonic transmittance of 100% may be obtained.

However, when reviewing FIGS. 5A to 5C again, it can be seen that lines satisfying the magnitude matching condition change according to the frequency as illustrated in FIGS. 5A to 5C. That is, there is a disadvantage in that it is necessary to find an ultrasonic transmission member satisfying the magnitude matching condition for each desirable frequency.

If it is possible to find an ultrasonic transmission member capable of satisfying the magnitude matching condition even by adjusting only the distance $d_0$ irrespective of a frequency, the above-described problem will be solved.

That is, the above-described problem may be solved by finding characteristics of a special ultrasonic transmission member capable of satisfying the magnitude matching condition at all frequencies.

Figure 7:
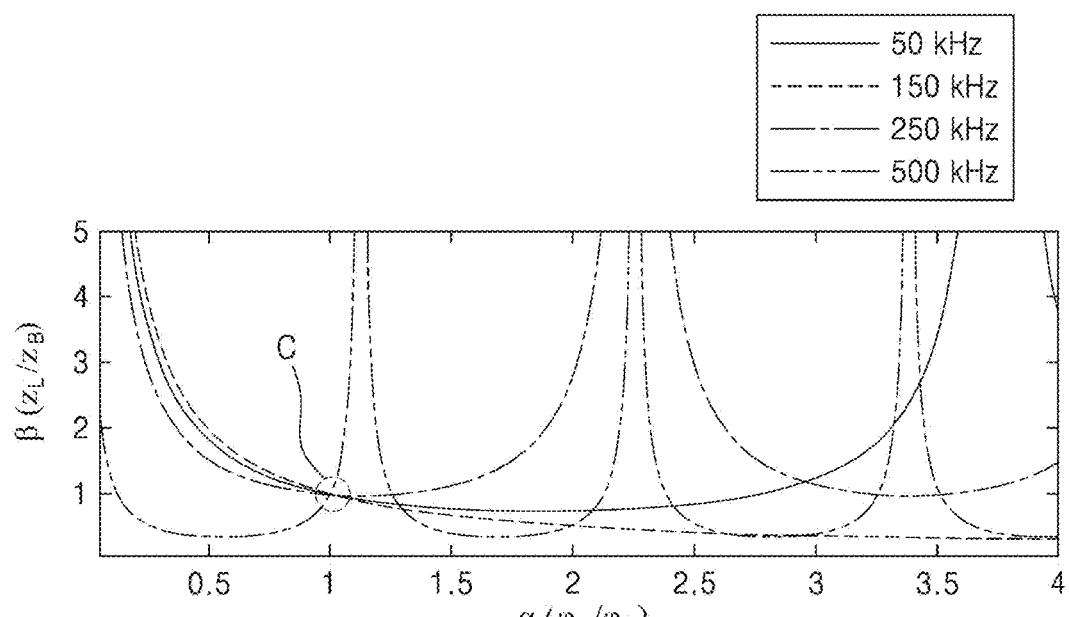
FIG. 7 illustrates a line diagram that satisfies a magnitude matching condition or a 100% transmission condition for various frequencies.

FIG. 7 illustrates a line diagram that satisfies the magnitude matching condition or a 100% transmission condition for various frequencies.

As illustrated in FIG. 7, it can be seen that all lines pass a point (C) in which $\alpha=1$ and $\beta=1$ for various frequencies. Here, $\alpha$ and $\beta$ are as previously defined.

That is, under the conditions that satisfy $\alpha=1$ and $\beta=1$, when only the phase matching condition is satisfied (that is, only distance $d_0$ is adjusted), a transmittance may constantly achieve 100% irrespective of the frequency.

<Transmittance of Ultrasonic Wave by Wave Control Method>

According to a wave control method described above, when an ultrasonic transmission member formed of a predetermined material is placed at a position away from an obstacle by a specific distance, a resonance phenomenon of a wave occurs between the ultrasonic transmission member and the obstacle, and thereby, it can be seen that a high-energy wave may transmit therethrough.

That is, when a material of the ultrasonic transmission member is appropriately selected and a distance between the ultrasonic transmission member and the obstacle is properly set, the ultrasonic transmission member may have a transmittance of 100% and make wave energy transmit through the ultrasonic transmission member and the obstacle without reflection.

2. Ultrasonic Transmission Apparatus According to Embodiment of the Present Disclosure Hereinafter, an ultrasonic transmission apparatus 1 according to an embodiment of the present disclosure will be described based on the above theoretical basis.

Figure 8:
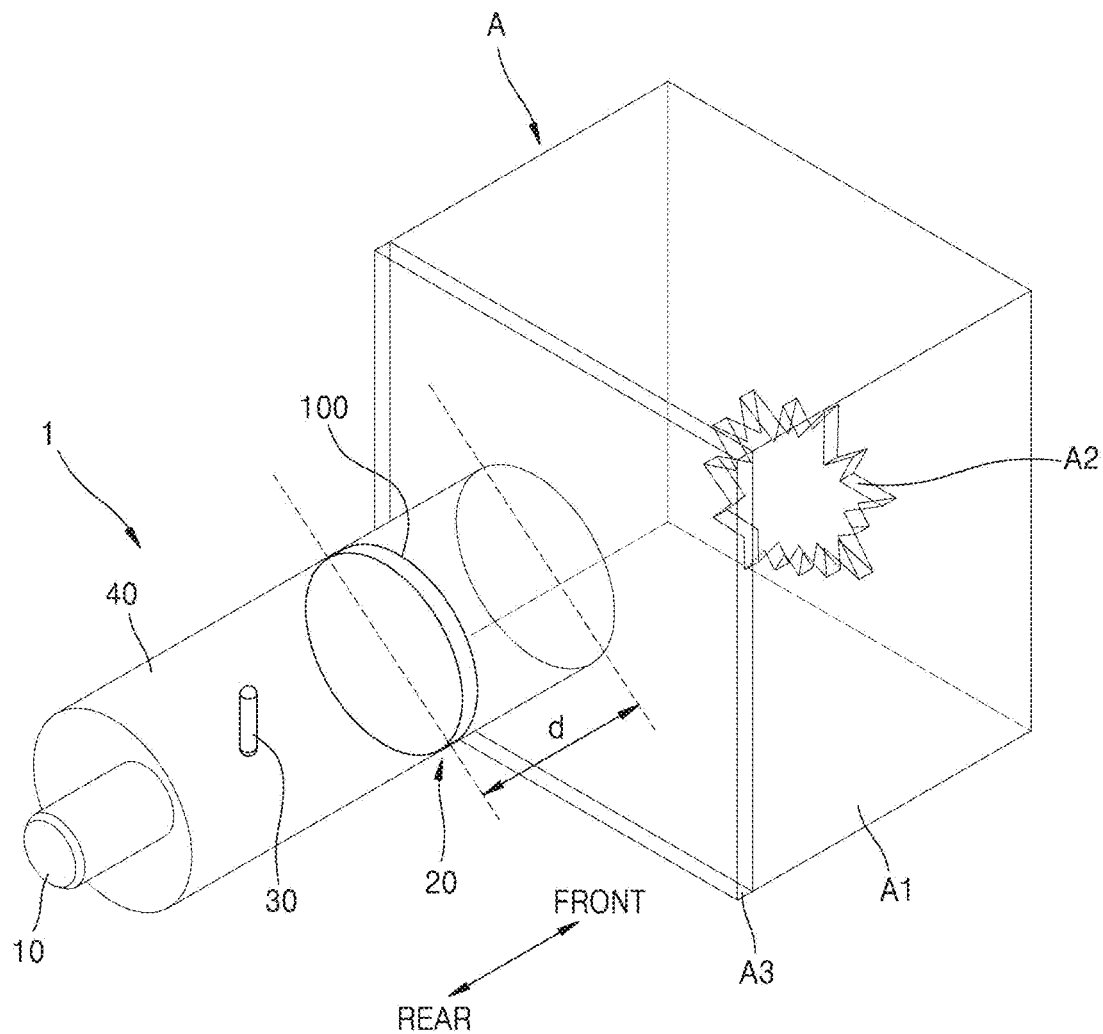
FIGS. 8 and 9 are conceptual diagrams illustrating a structure of an ultrasonic transmission apparatus according to an embodiment of the present disclosure.
Figure 9:
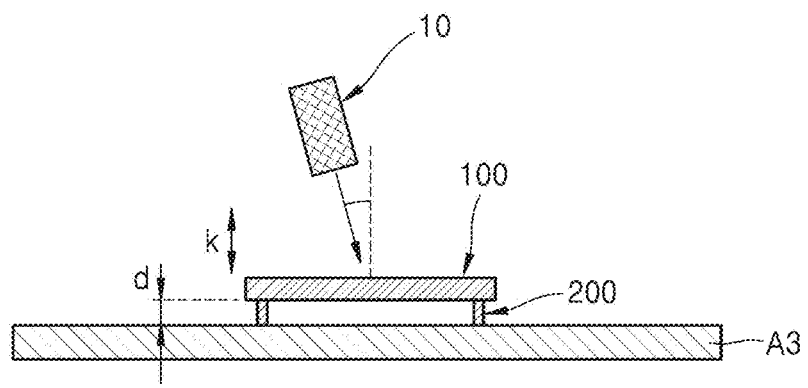

FIGS. 8 and 9 are conceptual diagrams illustrating a structure of the ultrasonic transmitting device 1 according to the embodiment of the present disclosure.

For the sake of convenience, a front-rear direction indicating a direction hereinafter will be described based on a "front-rear direction" illustrated in FIG. 8.

The ultrasonic transmission apparatus 1 according to the embodiment of the present disclosure performs an ultrasonic inspection by injecting an ultrasonic wave into an object A that includes a medium A1 and an inspection body A2 inside and includes an obstacle A3 outside.

The ultrasonic transmission apparatus 1 according to the embodiment of the present disclosure includes an ultrasonic generation device 10, an ultrasonic transmission module 20, an ultrasonic measurement device 30, and a guide 40.

The ultrasonic generation device 10 may generate a predetermined ultrasonic wave. A specification and a type of the ultrasonic generation device 10 are not limited.

A frequency of an ultrasonic wave generated by the ultrasonic generation device 10 is not limited in particular.

The ultrasonic wave generated by the ultrasonic generation device 10 becomes an incident wave incident on the object A.

The ultrasonic transmission module 20 is between the obstacle A3 and the ultrasonic generation device 10. Accordingly, the ultrasonic transmission module 20 is located on a travel path of the incident wave generated by the ultrasonic generation device 10 and incident on the object A. Accordingly, the incident wave passes through the ultrasonic transmission module 20 and then is incident on the object A.

At this time, the ultrasonic transmission module 20 causes the incident wave generated by the ultrasonic generating device 10 to pass through the obstacle A3 of the object A and to reach the inspection body A2 existing inside the object A. In addition, the ultrasonic transmission module 20 may cause a phase and a magnitude of the transmitted wave passing through the ultrasonic transmission member 100 and the obstacle A3 to be the same as a phase and a magnitude of the incident wave generated by the ultrasonic generation device 10. That is, the transmittance may be set to 100%.

The ultrasonic measurement device 30 is a member that performs an ultrasonic inspection by measuring a reflected wave reflected from the inspection body A2. A specification, a type, and arrangement of the ultrasonic measurement device 30 are not limited.

The guide 40 may serve as a passage through which an ultrasonic wave generated by the ultrasonic generation device 10 transmits. In addition, the guide 40 may serve as a housing for appropriately installing the ultrasonic generating device 10 and the ultrasonic transmission module 20.

Hereinafter, the ultrasonic transmission module 20 will be described in more detail.

The ultrasonic transmission module 20 may include an ultrasonic transmission member 100 and a position variable member 200.

The ultrasonic transmission member 100 may have a predetermined panel shape located on a transmission path of an ultrasonic wave generated by the ultrasonic generation device 10.

The ultrasonic transmission member 100 may have a predetermined physical property and a thickness. Accordingly, the ultrasonic transmission member 100 may have predetermined impedance and phase with respect to an incident wave.

According to an embodiment, the ultrasonic transmission member 100 may be selectively replaced. That is, the physical property and thickness of the ultrasonic transmission member 100 may be selectively changed. Accordingly, the impedance and phase of the ultrasonic transmission member 100 for the incident wave may also be selectively replaced.

Specific physical property, shape, thickness, and size of the ultrasonic transmission member 100 are not limited. For example, the ultrasonic transmission member 100 may have various shapes such as a square, a circle, and a polygon, and may also have a shape having a straight line and a curvature.

In addition, the ultrasonic transmission member 100 may have a structure in which a single medium or multiple media are stacked but is not limited thereto. In addition, when the ultrasonic transmission member 100 is composed of multiple media, the ultrasonic transmission member 100 may be partially stacked in addition to the simple stacked form or may have a configuration having different physical property of a certain part. In addition, a distribution between media may also have a regular or irregular distribution.

Figure 10:
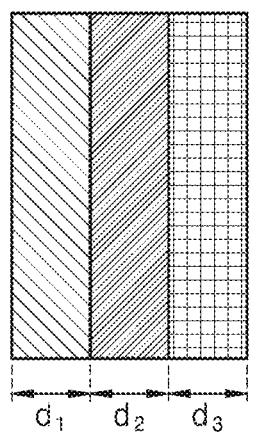
FIGS. 10 and 11 are conceptual diagrams illustrating structures of an ultrasonic transmission member used in an ultrasonic transmission apparatus according to an embodiment of the present disclosure.
Figure 10:
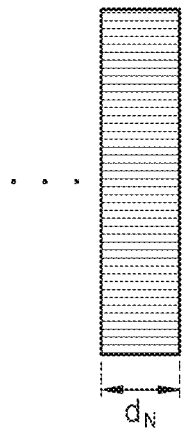
Figure 10:
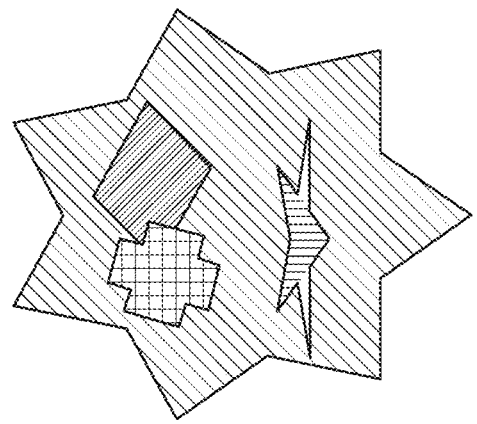
Figure 10:
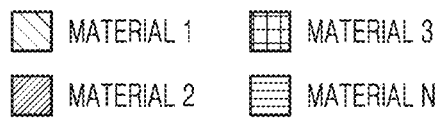
Figure 10:
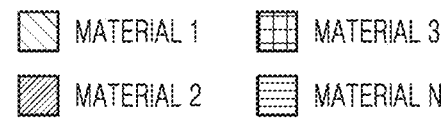

This will be described with reference to a drawing, that is, FIG. 10. That is, physical property, distribution, and so on of the ultrasonic transmission member 100 may be selected according to an obstacle or may be freely selected.

A processing form of the ultrasonic transmission member 100 is also not limited. For example, the ultrasonic transmission member 100 may be made by applying regular or irregular processing to a single material or multiple materials, and various shapes of processing are possible, such as, an angular shape, a curvature shape, or a mixture thereof.

Figure 11:
Figure 11:
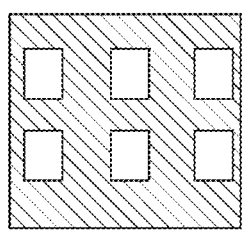
Figure 11:
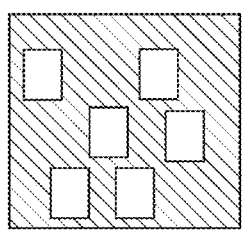
Figure 11:
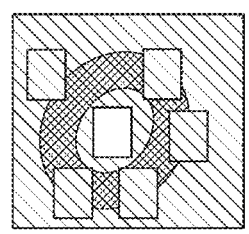
Figure 11:
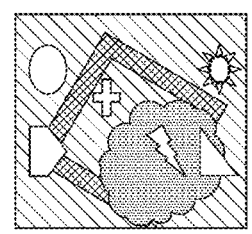

This will be described with reference to a drawing, that is FIG. 11. That is, a size, a shape, a width, and so on of the ultrasonic transmission member 100 may be selected according to an obstacle or may be freely selected.

The position variable member 200 varies a position of the ultrasonic transmission member 100.

Specific shape and configuration of the position variable member 200 are not limited, and may include an integral position variable member that may be easily applied by a person skilled in the art.

For example, the position variable member 200 may include a rack gear and a pinion gear that have an operation direction in a front-rear direction.

As another example, the position variable member 200 may include a guide 40 line extending in the front-rear direction and a guide 40 block of which position is movable in the front-rear direction along the guide 40 line.

However, this is only an example, and the position variable member 200 may include all members for changing a position of the ultrasonic transmission member 100.

By having the above configuration, the position variable member 200 may vary a distance between the obstacle A3 and the ultrasonic transmission member 100.

Because the ultrasonic transmission module 20 described above is provided, an incident wave generated by the ultrasonic generation device 10 may reach the inspection body A2 after passing through the ultrasonic transmission module 20 and the obstacle A3. In this case, the ultrasonic transmission member 100 of the ultrasonic transmission module 20 may satisfy a phase matching condition and a magnitude matching condition. Accordingly, the incident wave may pass through the obstacle A3 without being reflected from the obstacle A3. That is, the ultrasonic transmission member 100 may be considered to correspond to the ultrasonic transmission member in the wave control method according to the present disclosure described above.

Hereinafter, specific description will be made on the ultrasonic transmission member 100 according to an embodiment capable of satisfying the phase matching condition, the magnitude matching condition, and additional condition described above.

First, the magnitude matching condition is considered.

The obstacle A3 may have predetermined impedance and phase. In addition, the ultrasonic transmission member 100 may also have predetermined impedance and phase. The impedance of the obstacle A3 and the impedance of the ultrasonic transmission member 100 have a predetermined ratio. In addition, there is also a predetermined ratio between the phase of the obstacle A3 and the phase of the ultrasonic transmission member 100.

According to an embodiment, a ratio between the impedance of the obstacle A3 and the impedance of the ultrasonic transmission member 100, and a ratio between the phase of the obstacle A3 and the phase of the ultrasonic transmission member 100 may satisfy the magnitude matching conditions described above.

First, the impedance ratio $\beta$ between the obstacle A3 and the ultrasonic transmission member 100, and the phase ratio $\alpha$ between the obstacle A3 and the ultrasonic transmission member 100 are represented by following Equation (6). The Equation (6) is the same as described in Equation (6) and related description thereon.

$$\alpha \equiv \frac{\varphi_L}{\varphi_B} = \frac{k_L d_L}{k_B d_B}, \beta \equiv \frac{z_L}{z_B} \qquad \text{Equation (6)}$$

In addition, the impedance ratio $\beta$ between the obstacle A3 and the ultrasonic transmission member 100, and the phase ratio $\alpha$ between the obstacle A3 and the ultrasonic transmission member 100 may satisfy following Equation (8). Equation (8) is the same as described in Equation (8) and related description thereon.

$$1 = |\chi(\alpha, \beta)| \qquad \text{Equation (8)}$$

According to an embodiment, a magnitude matching condition may be satisfied first by selecting the ultrasonic transmission member 100 that satisfies Equation (8) described above. Of course, even when the magnitude matching condition is not completely satisfied, it is possible to achieve a greater increase in transmittance than when there is no ultrasonic transmission member 100. Accordingly, it is also possible to select the ultrasonic transmission member 100 that does not completely satisfy the magnitude matching condition.

Next, a phase matching condition is considered.

When the impedance and phase of the obstacle A3 are set as described above and the impedance and phase of the ultrasonic transmission member 100 are set, a position of the ultrasonic transmission member 100 that satisfies the phase matching condition may be derived. That is, the distance $d_0$ that satisfies the phase matching condition may be derived by adjusting a distance d between the obstacle A3 and the ultrasonic transmission member 100. The distance $d_0$ satisfies following Equation (7), and Equation (7) is the same as described in Equation (7) and related description thereon.

$$d_0 = \frac{\varphi_0}{k_0} = \frac{c_{p0}}{2\omega} L X(\alpha, \beta) \qquad \text{Equation (7)}$$

Meanwhile, as described above, it can be seen that the impedance ratio $\beta$ between the obstacle A3 and the ultrasonic transmission member 100 which satisfy the magnitude matching condition, and the phase ratio $\alpha$ between the obstacle A3 and the ultrasonic transmission member 100 change according to a frequency. To solve this, when only the phase matching condition is satisfied regardless of a frequency, that is, when only the phase matching condition is satisfied by adjusting the distance $d_0$ between the obstacle A3 and the ultrasonic transmission member 100 as described above, it is desirable for a 100% transmission condition to be satisfied. To this end, the ultrasonic transmission member 100 that satisfies following Equation (9) may be selected. Equation (9) corresponds to the additional condition described above.

$$\alpha = 1, \beta = 1 \qquad \text{Equation (9)}$$

Meanwhile, in order to derive a physical property of the ultrasonic transmission member 100 that satisfies Equation (6) to Equation (9) and a distance between the ultrasonic transmission member 100 and the obstacle A3, a predetermined processing device may be provided.

The processing device may include a predetermined CPU or so on. The processing device may select the ultrasonic transmission member 100 that satisfies the equations through a predetermined operation and data processing and may derive a distance between the ultrasonic transmission member 100 and the obstacle A3.

3. Experimental Results of Present Disclosure

Figure 12A:
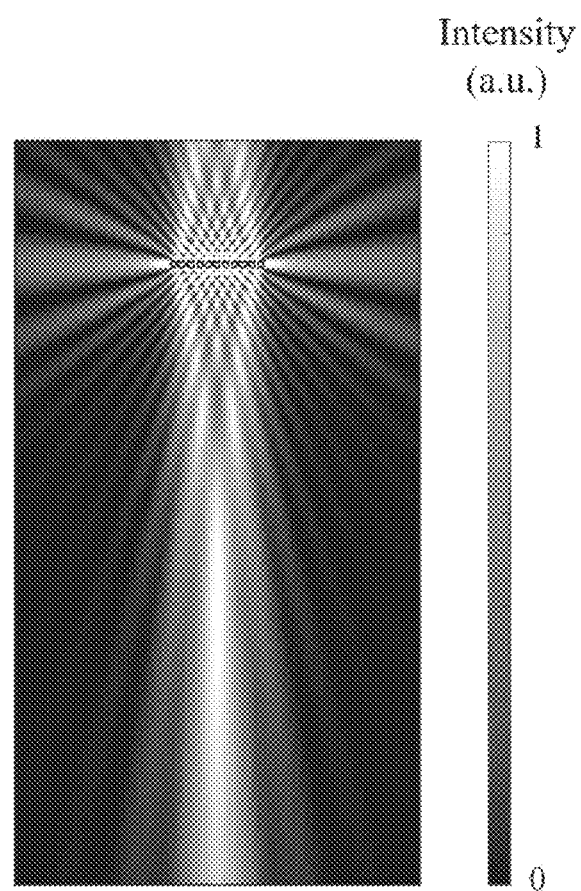
FIGS. 12A to 12C and FIGS. 13A to 13C are simulation results illustrating performance of an ultrasonic transmission apparatus and a wave control method for various wave sources, according to embodiments of the present disclosure.
Figure 13A:
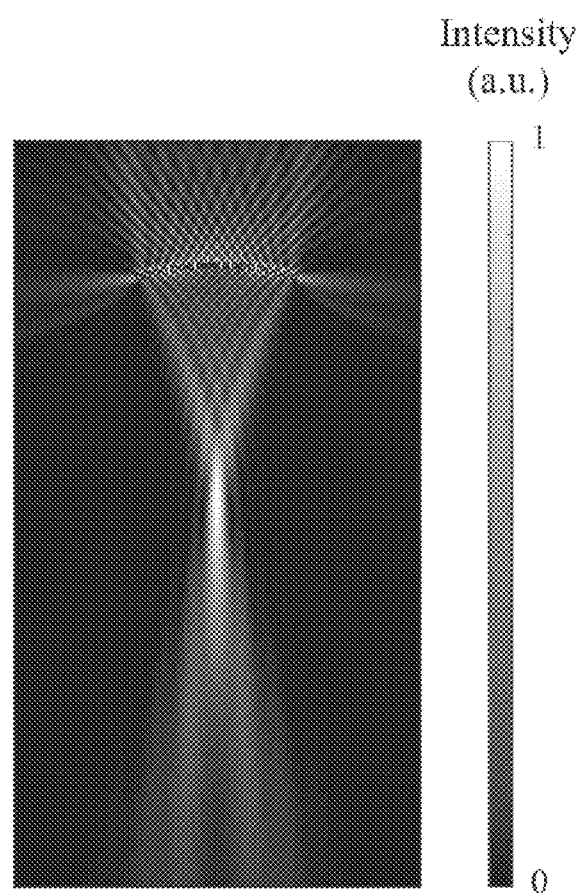
Figure 13B:
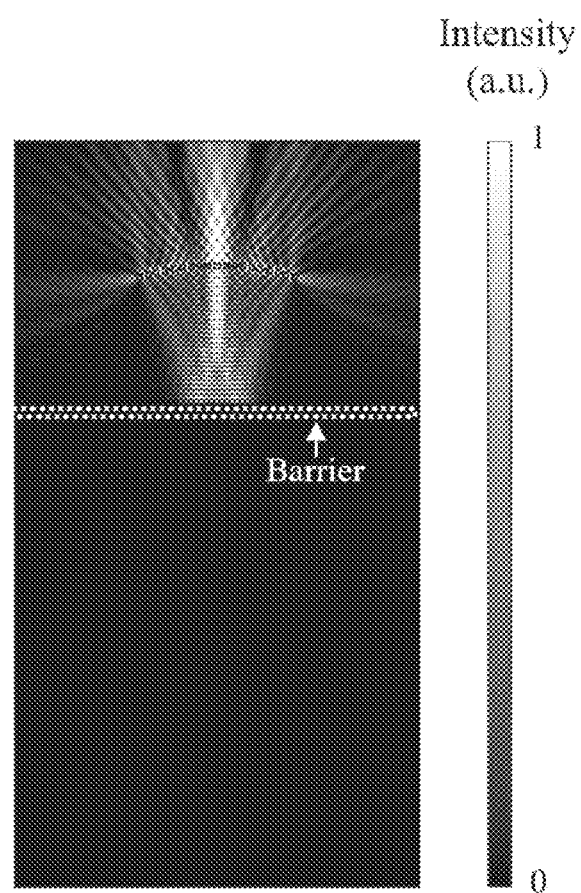
Figure 13C:
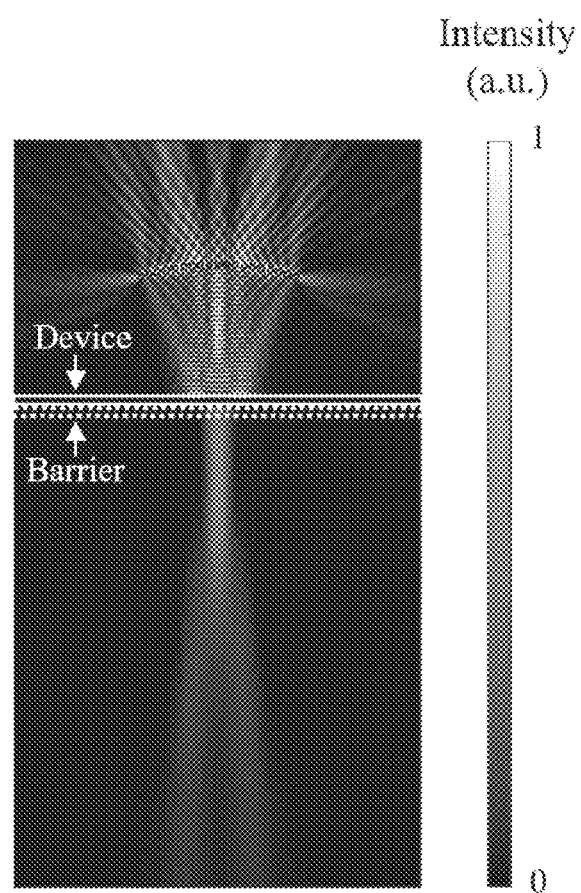

FIGS. 12A and 13C are simulation results illustrating performance of the ultrasonic transmission apparatus 1 and the wave control method according to embodiments of the present disclosure for various wave sources.

FIGS. 12A and 13C are examples of simulation in which the ultrasonic transmission apparatus 1 and the wave control method according to the embodiments of the present disclosure are applied to a single ultrasonic wave generation device and a multiple-ultrasonic-wave generation device (phase array) system which are representative technologies widely used in ultrasonic technology, respectively.

Figure 12B:
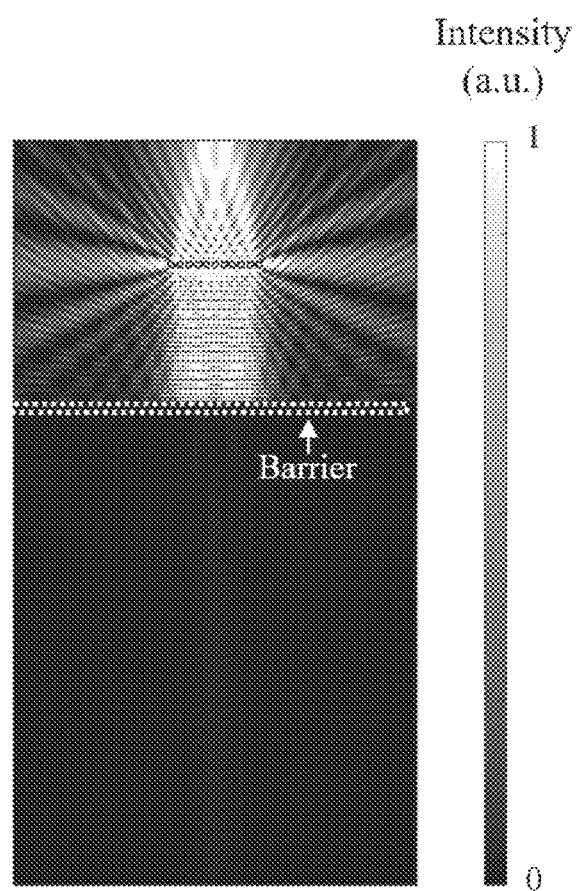
Figure 12C:
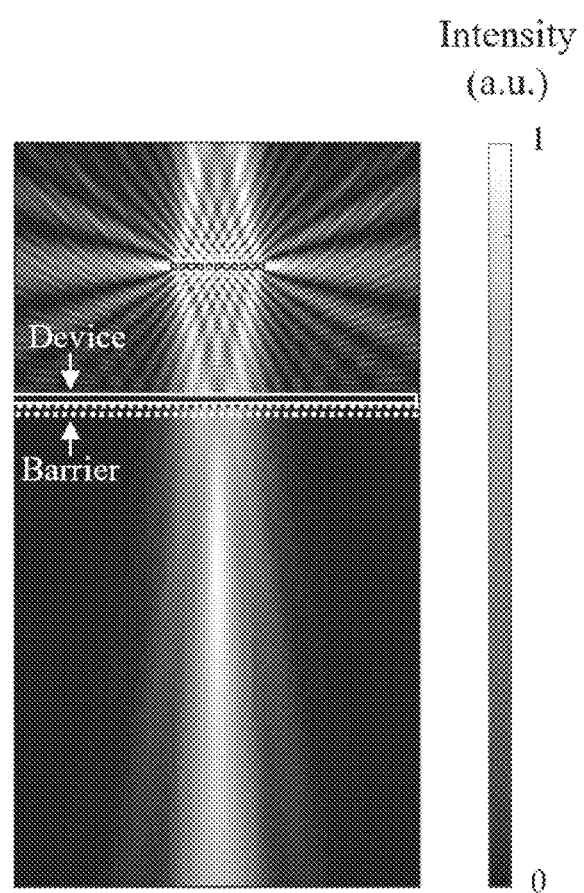

FIG. 12A and FIG. 13A illustrate a case in which an existing ultrasonic technology is used without an obstacle, FIG. 12B and FIG. 13B illustrate a case in which the existing ultrasonic technology is used and a bone obstacle having a thickness of 5 mm is encountered, and FIG. 12C and FIG. 13C illustrates results in a case in which the ultrasonic transmission apparatus 1 and the wave control method according to embodiments of the present disclosure are used.

As can be seen from the simulation results illustrated in the drawings, the ultrasonic transmission apparatus 1 and the wave control method may be applied to various ultrasonic technologies currently in use, and performance thereof may also be innovatively improved. In addition, the ultrasonic transmission apparatus 1 and the wave control method may be applied to not only a wave incident vertically but also a wave that travels at a certain angle.

Figure 14A:
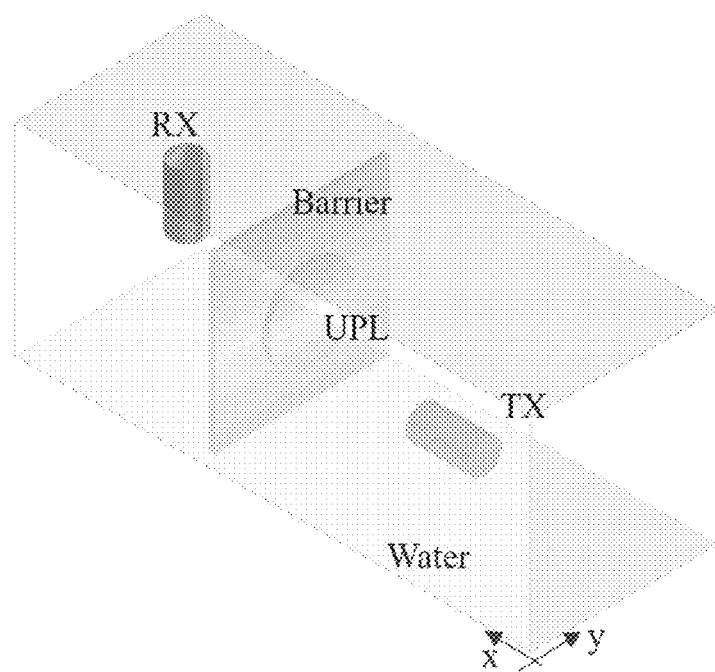
FIG. 14A schematically illustrates an acoustic field scan system used in an experiment.
Figure 14B:
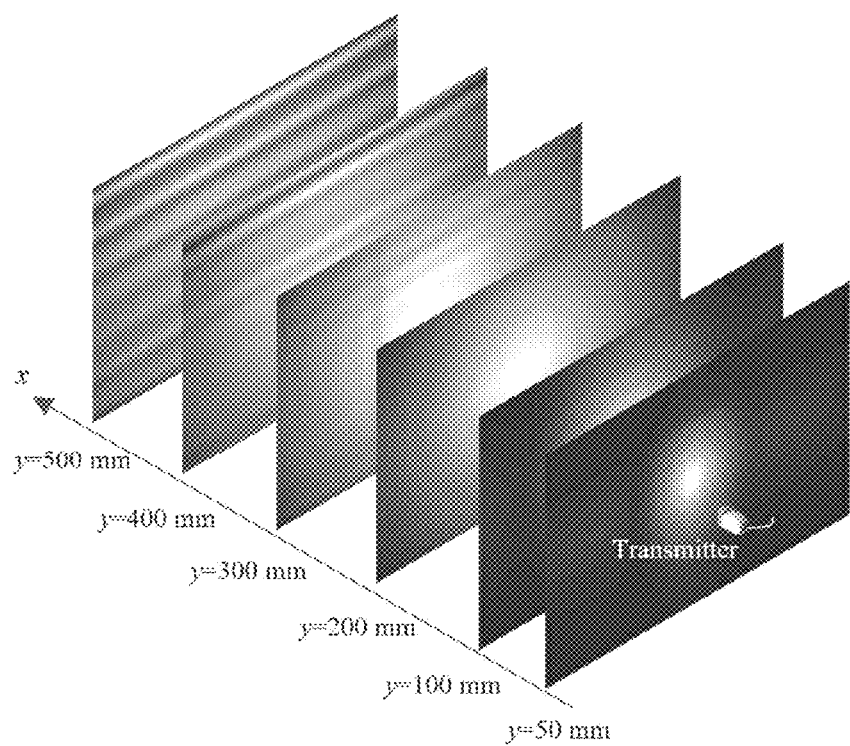
FIG. 14B illustrates transducer acoustic field measurement results.

FIG. 14A schematically illustrates an acoustic field scan system used in an experiment, and FIG. 14B illustrates transducer acoustic field measurement results. In addition, FIG. 15 illustrates the experimental results.

Referring to FIG. 14B, it can be seen that a wave generated by a transmitter TX spreads while travelling. In order to verify an ultrasonic wave transmission experiment, an acoustic field was measured at a 400-mm transmitter point for three cases: a case in which there is no obstacle (Ref), a case in which an obstacle is installed, and a case in which an ultrasonic transmitter is installed.

Figure 15:
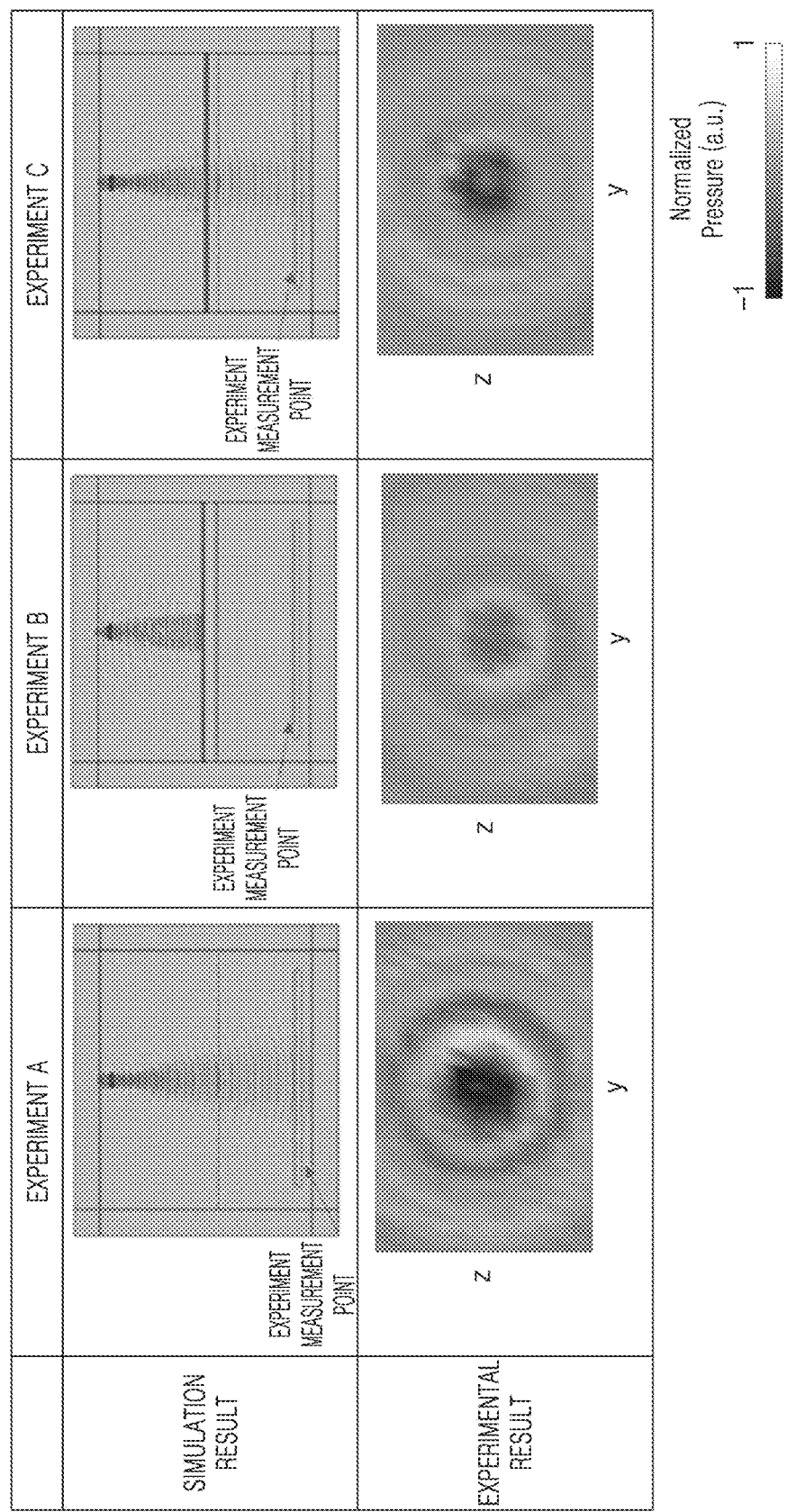
FIG. 15 illustrates experiment results.

The measurement results are illustrated in FIG. 15. An experiment A of FIG. 15 is a case in which there is no obstacle, an experiment B of FIG. 15 is a case in which an obstacle is installed, and an experiment C of FIG. 15 illustrates a result in a case in which the ultrasonic transmission apparatus 1 and the wave control method according to embodiments of the present disclosure are used.

As can be seen from FIG. 15, when there is an obstacle, intensity of the transmitted ultrasonic wave is very small. However, when the ultrasonic transmitter is installed, it can be seen that the ultrasonic wave transmits through the ultrasonic transmitter with a very high transmittance as if there is no obstacle.

Hereinafter, as a consideration on an additional condition, description will be made in which a single ultrasonic transmission apparatus 1 is used and various frequencies may be applied by adjusting only a distance between the ultrasonic transmission apparatus 1 and an obstacle.

Figure 16:
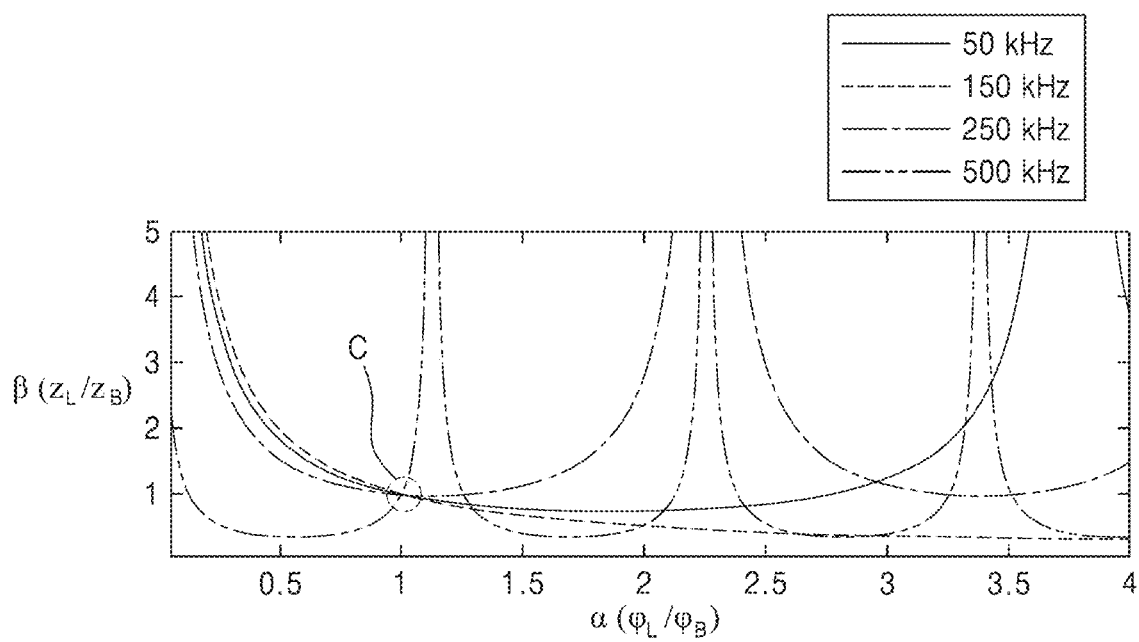
FIG. 16 is a graph illustrating curves representing maximum transmittance (FTC) at various frequencies.

FIG. 16 is a graph illustrating a curved line representing a maximum transmittance (FTC) at various frequencies.

Figure 17:
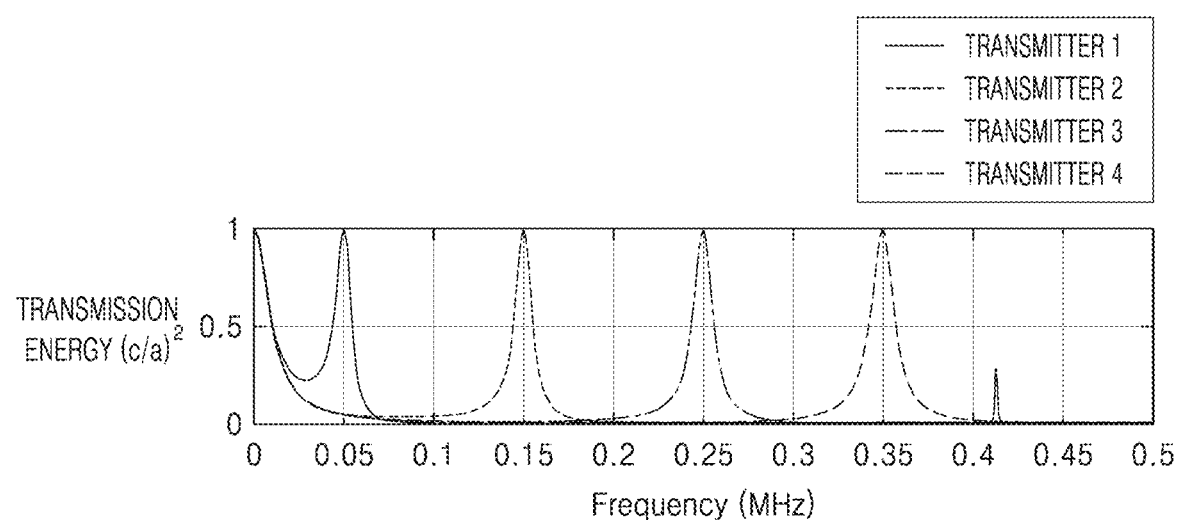
FIG. 17 is a diagram illustrating that, when a travel medium is water and an obstacle is an iron plate having a thickness of 3 mm, a physical property of an ultrasonic transmission apparatus 1 and a frequency representing maximum transmittance change together.

For example, when a travel medium is water and an obstacle is an iron plate having a thickness of 3 mm, it can be seen that frequencies representing the maximum transmittance change together as illustrated in FIG. 17 when a physical property of the ultrasonic transmission apparatus 1 is changed.

In particular, when $\alpha=\beta=1$ described above among the FTC condition, one ultrasonic transmission apparatus 1 may be used at all frequencies. In this case, a high-energy wave may transmit through a member at various desirable frequencies by adjusting a type of the ultrasonic transmission apparatus 1 or a distance between the ultrasonic transmission apparatus 1 and an obstacle.

Figure 18A:
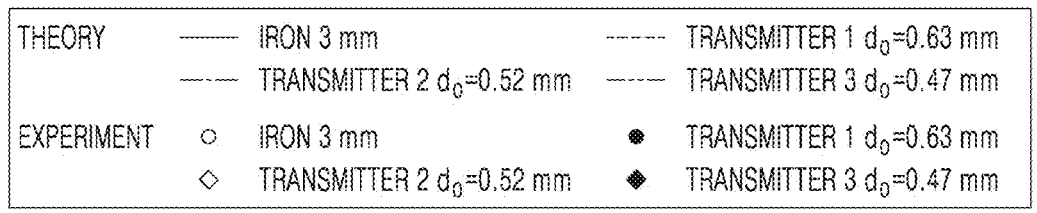
FIGS. 18A to 18E illustrate results of verification performed at various frequencies by installing an ultrasonic transmission apparatus satisfying α=β=1 for an iron plate, which is an obstacle, having a thickness of 3 mm and by adjusting a distance between the ultrasonic transmission apparatus and an obstacle.
Figure 18A:
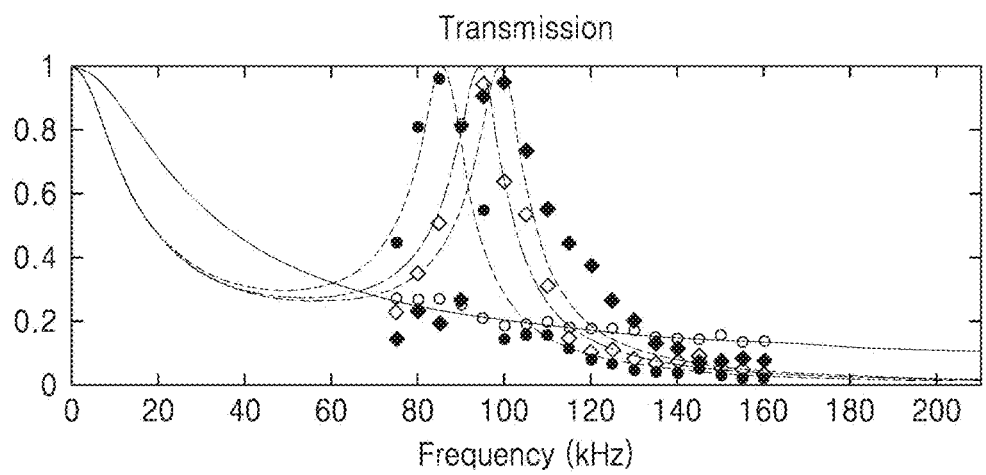
Figure 18B:
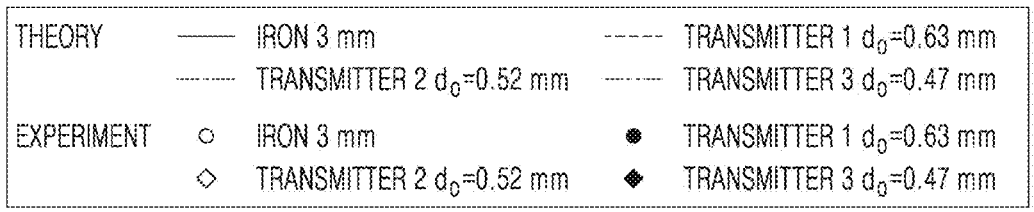
Figure 18B:
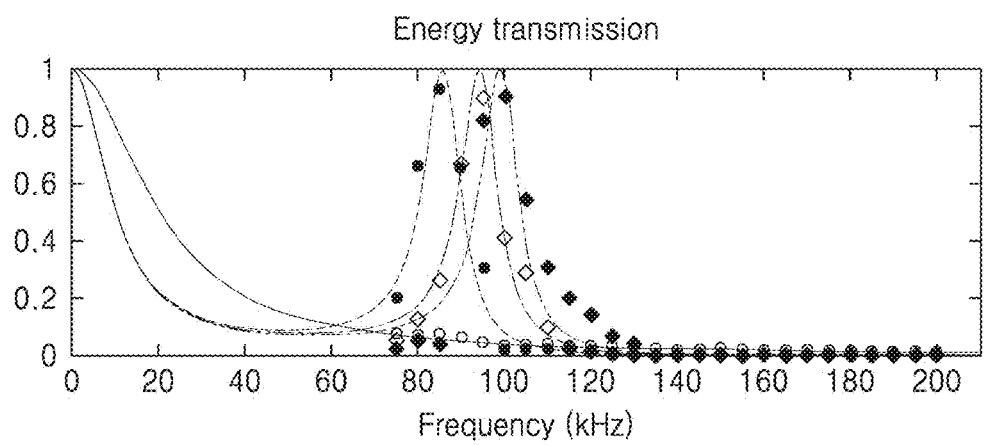
Figure 18C:
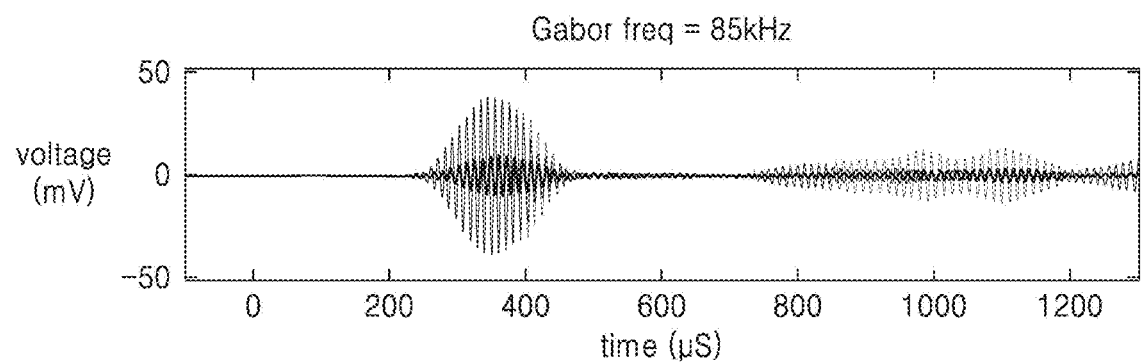
Figure 18D:
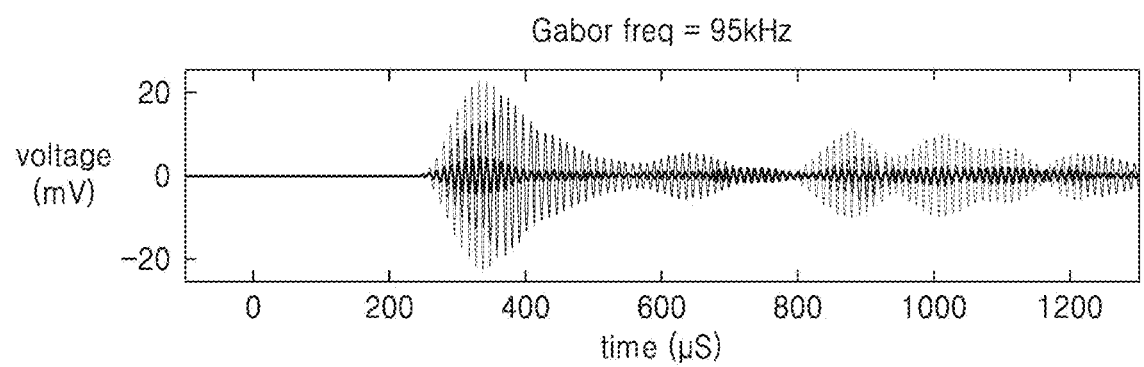
Figure 18E:
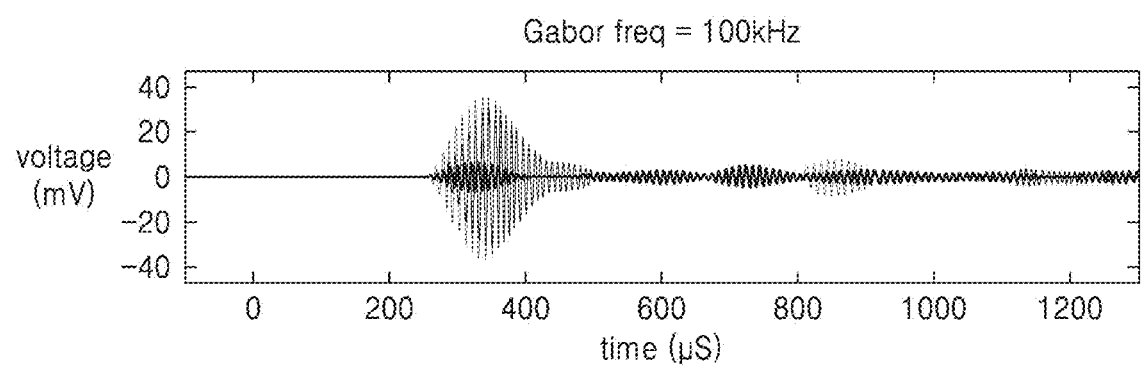

FIGS. 18A and 18E illustrate results of the experiment. FIGS. 18A to 18E illustrate results of verification performed at various frequencies by installing the ultrasonic transmission apparatus 1 satisfying $\alpha=\beta=1$ for an iron plate, which is an obstacle, having a thickness of 3 mm and by adjusting a distance between the ultrasonic transmission apparatus 1 and the obstacle.

As illustrated in FIGS. 18A to 18E, it can be seen that the verification results conform to the theory. Three graphs of FIGS. 18C, 18D, and 18E illustrate results of 85 kHz, 95 kHz, and 100 kHz illustrating the maximum transmittance in the ultrasonic transmission apparatus 1, 2, and 3.

As can be seen from FIG. 18B, when the ultrasonic transmission apparatus 1 is installed, very high transmission efficiency may be obtained as in a case in which there is no obstacle.

Figure 19:
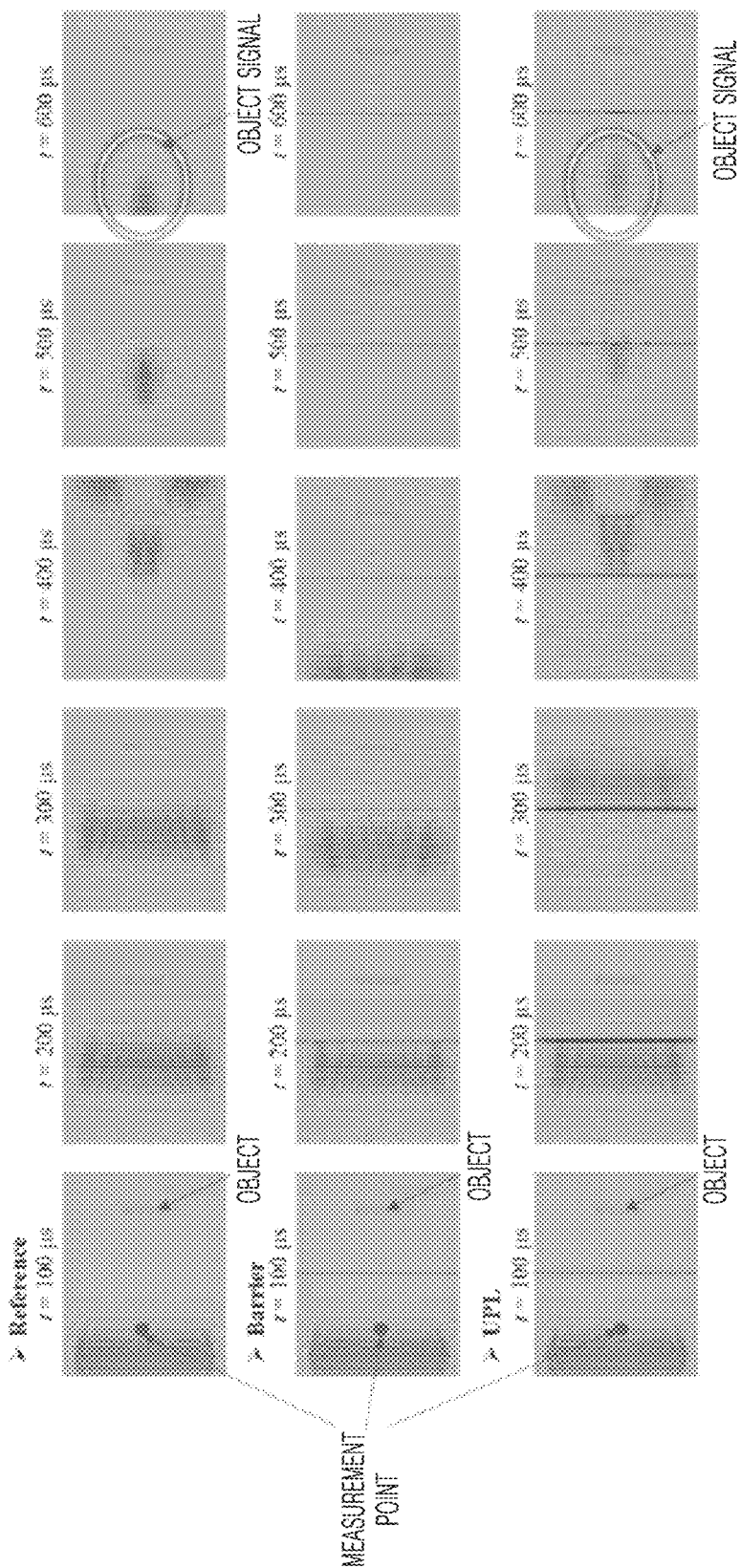
FIGS. 19 and 20A to 20F are diagrams illustrating simulation of whether or not an object may be imaged (identified) by using a linearly generated plane wave.
Figure 20A:
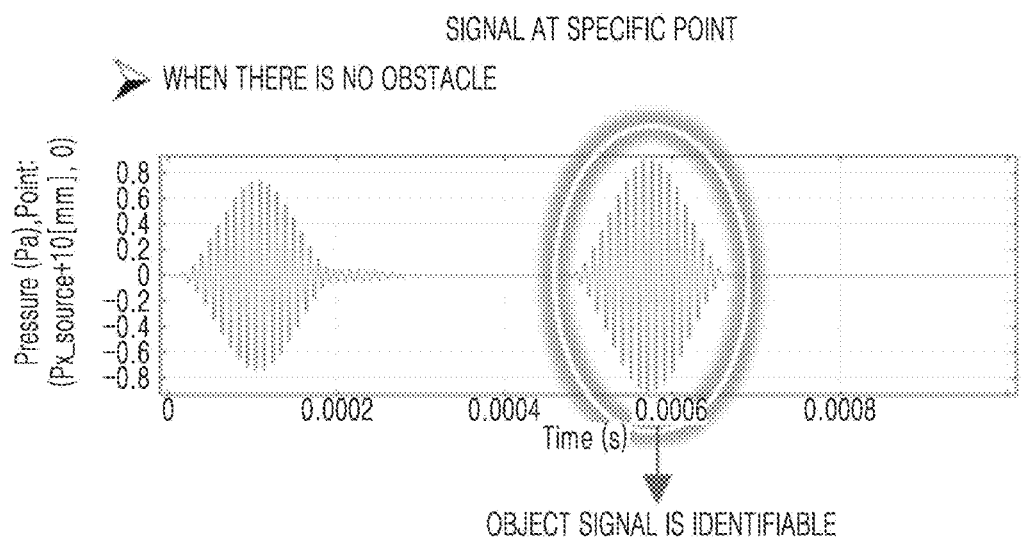
Figure 20B:
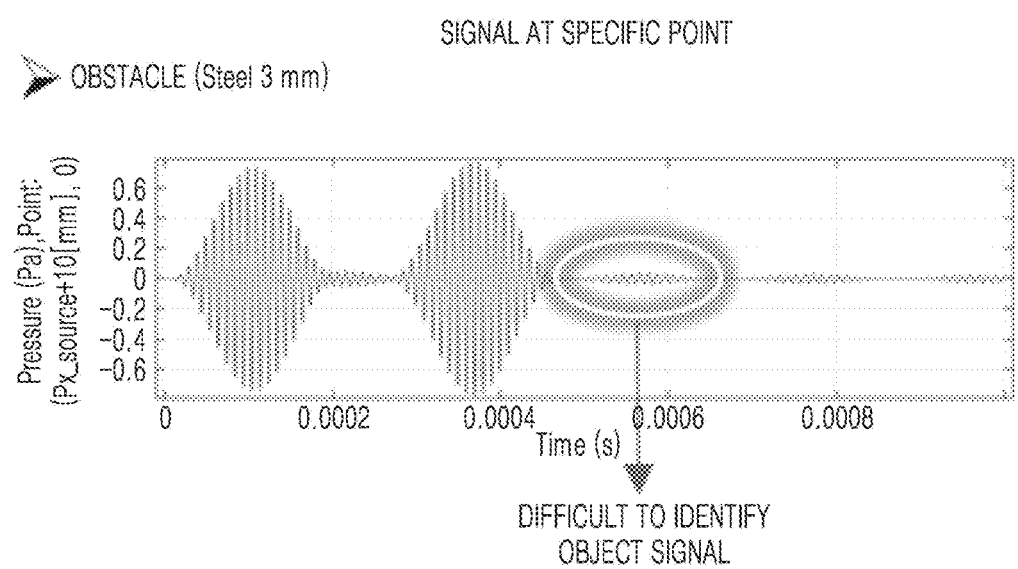
Figure 20C:
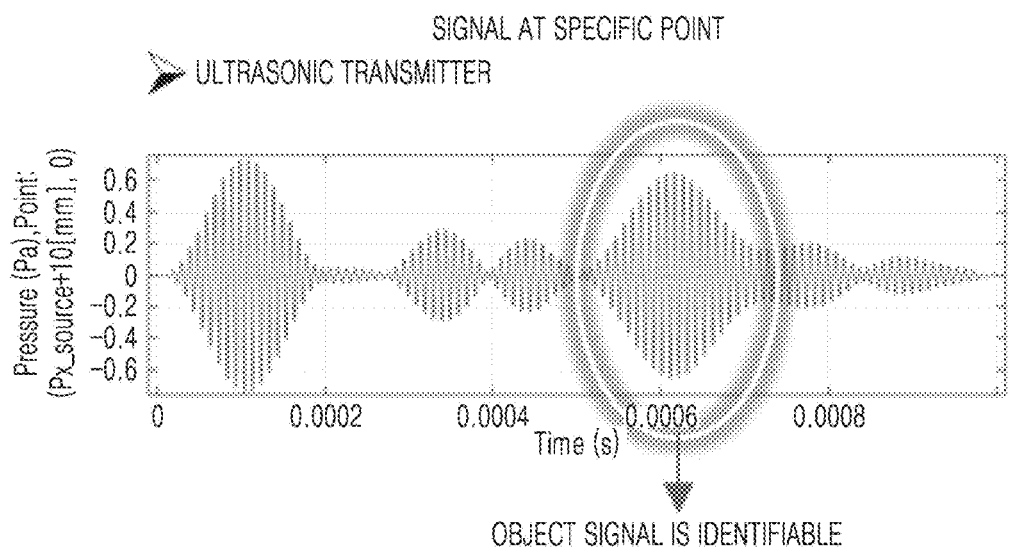
Figure 20D:
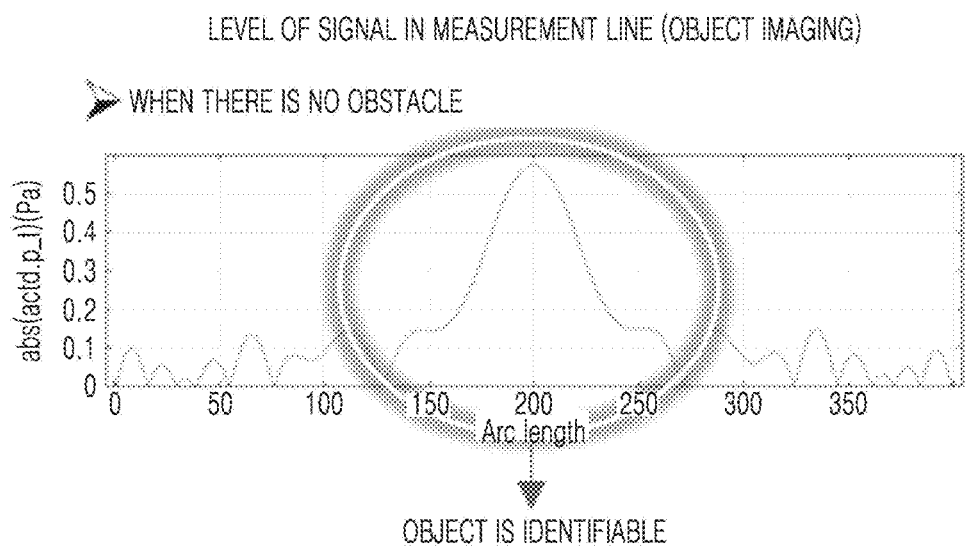
Figure 20E:
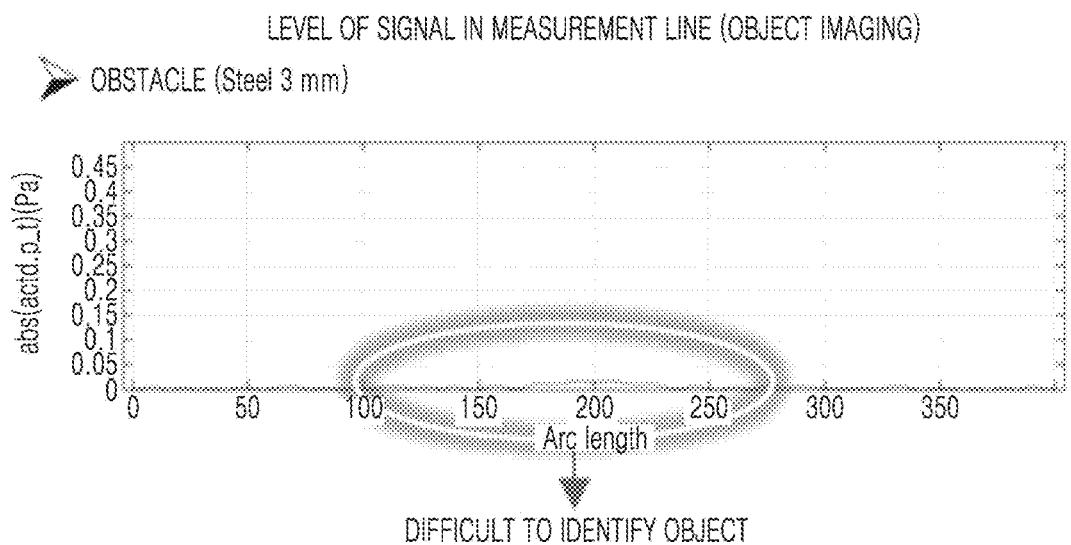
Figure 20F:
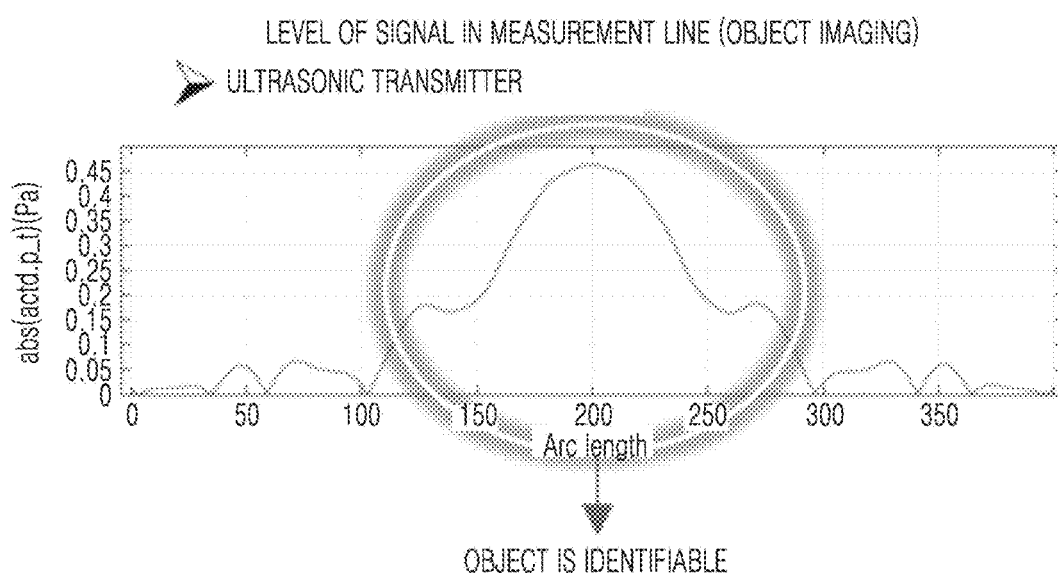

FIGS. 19 and 20 are views illustrating simulation of whether or not an object may be imaged (identified) by using a linearly generated plane wave.

When there is no obstacle, the object may be identified by using an ultrasonic wave reflected from the object, but when there is an obstacle, it is difficult to identify the object because a signal level is very small. For example, when a transmittance of an obstacle is 10%, a strength of an ultrasonic signal that hits the object again and returns to a measurement point is less than 1%, and thus, it is difficult to measure the ultrasonic signal.

However, when the ultrasonic transmission apparatus 1 according to the embodiment of the present disclosure is installed, the object may be identified as in a case in which there is no obstacle because the ultrasonic transmission apparatus 1 has a high ultrasonic transmittance.

FIGS. 21 to 25 illustrate a two-dimensional imaging experiment environment and experimental results.

Figure 21:
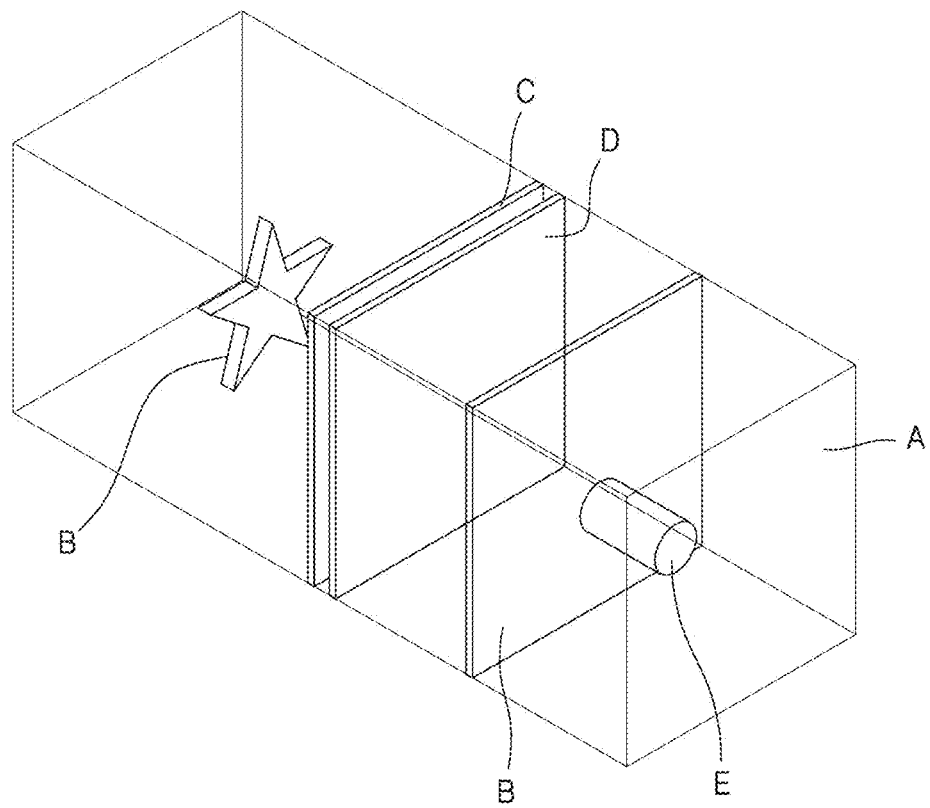
FIGS. 21 to 25D illustrate a two-dimensional imaging experiment environment and experimental results.
Figure 22:
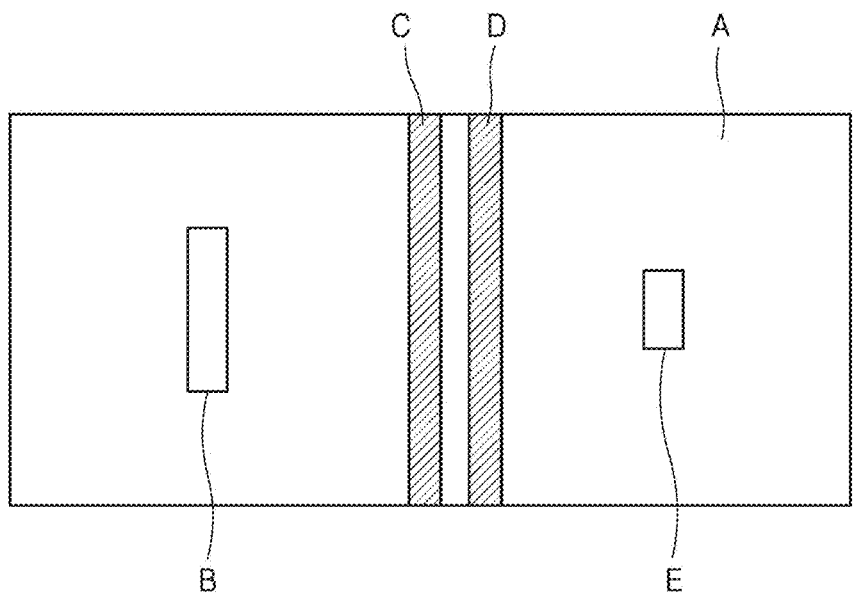
Figure 23A:
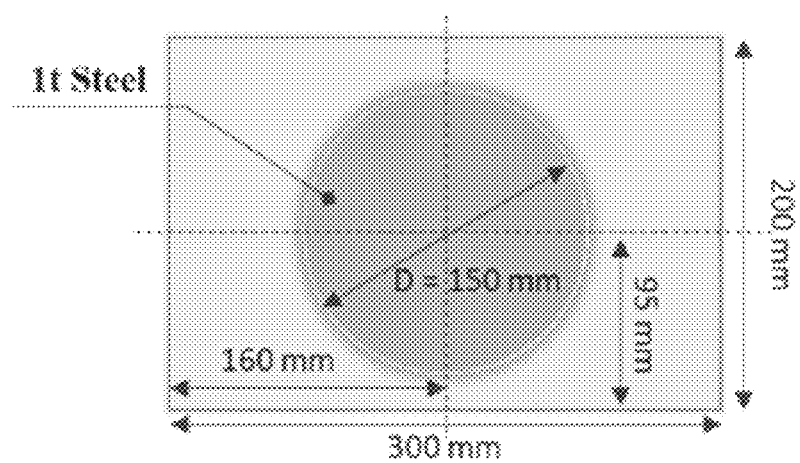
Figure 23B:
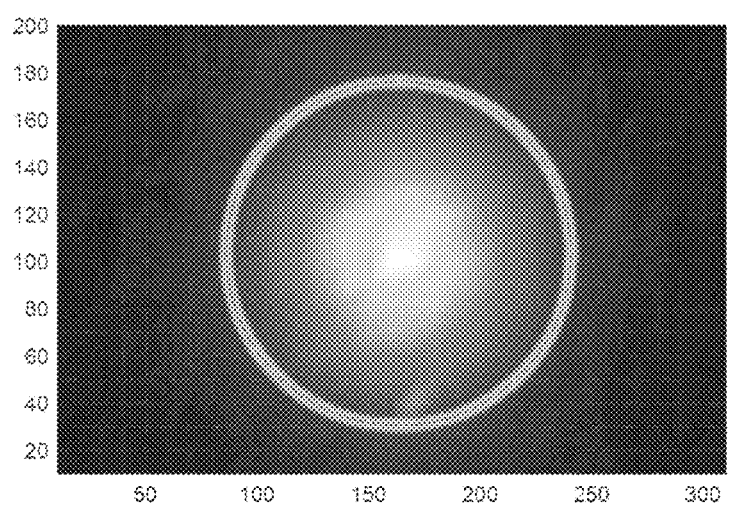
Figure 23C:
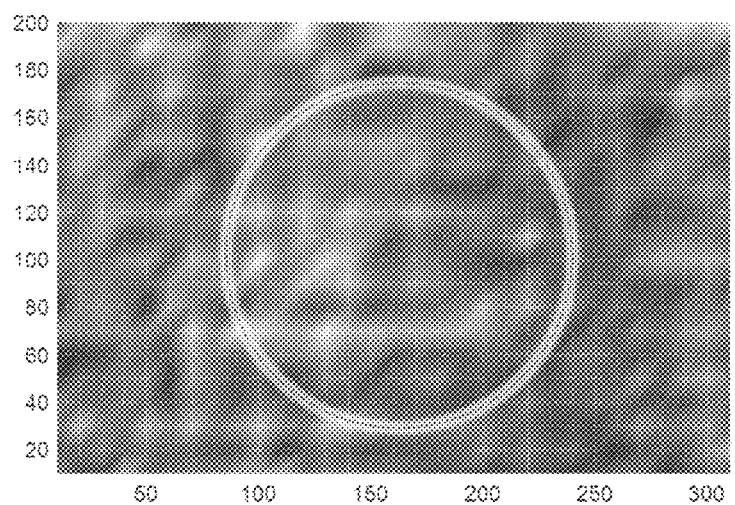
Figure 23D:
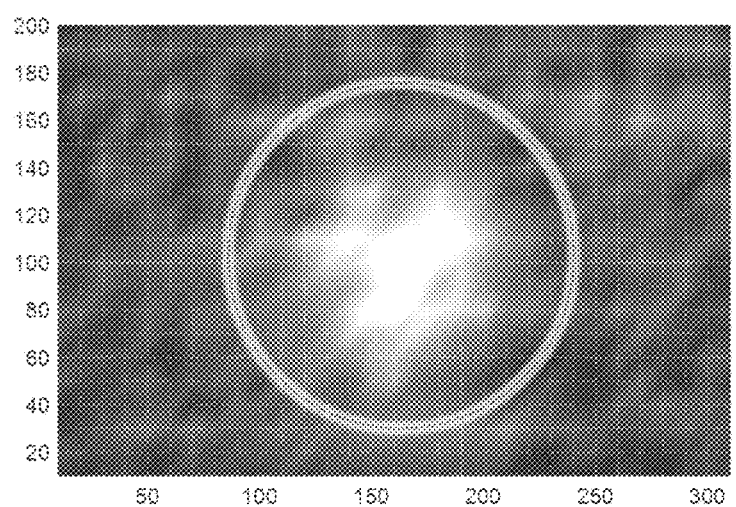
Figure 24A:
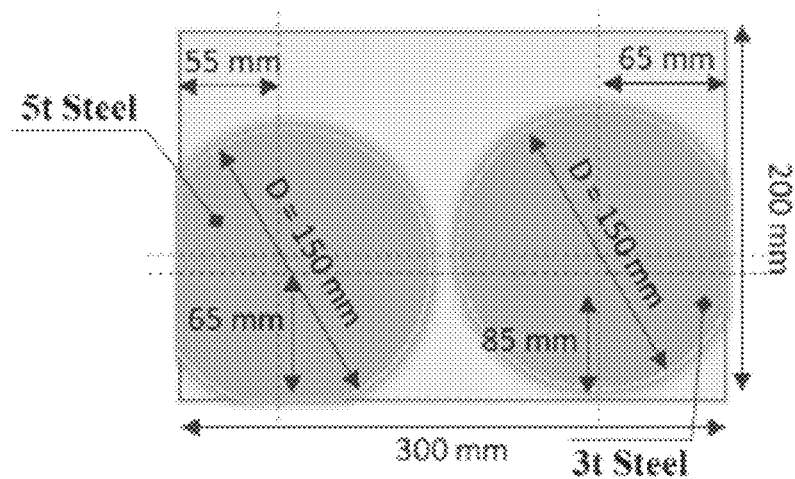
Figure 24B:
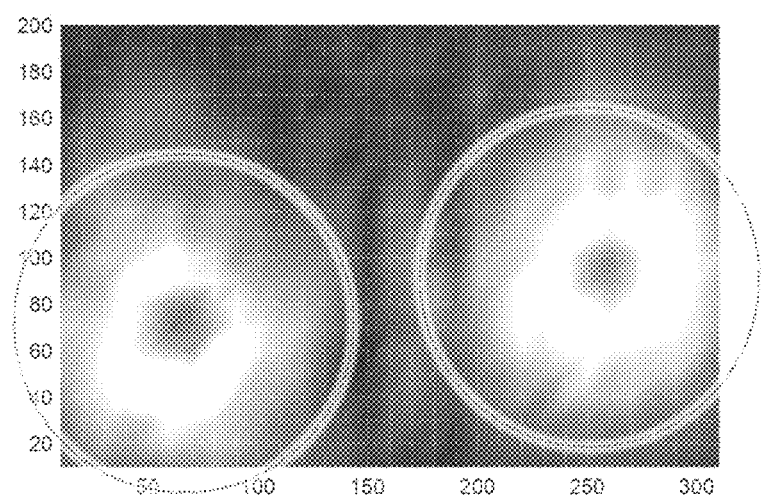
Figure 24C:
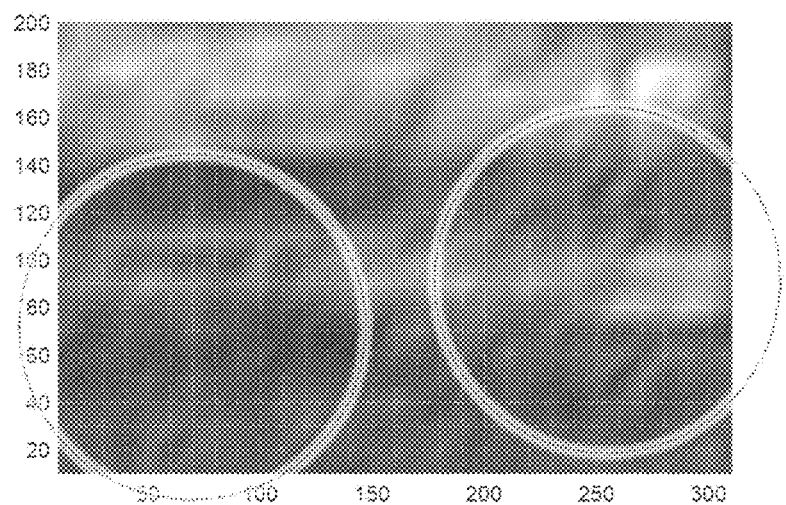
Figure 24D:
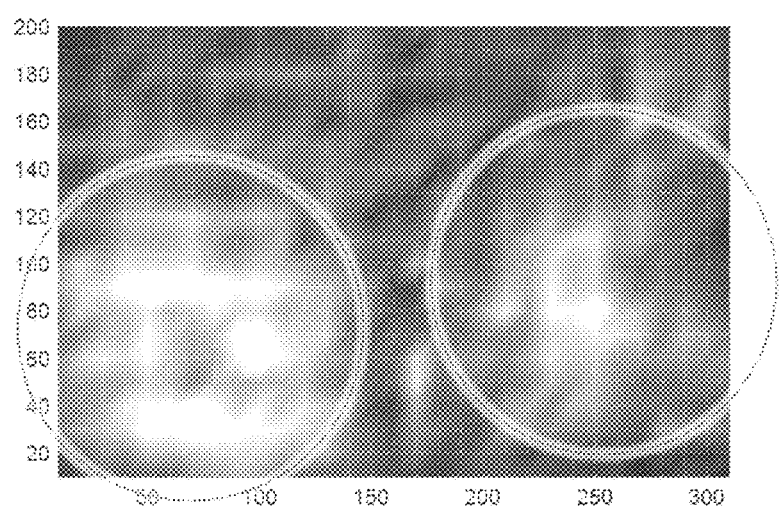
Figure 25A:
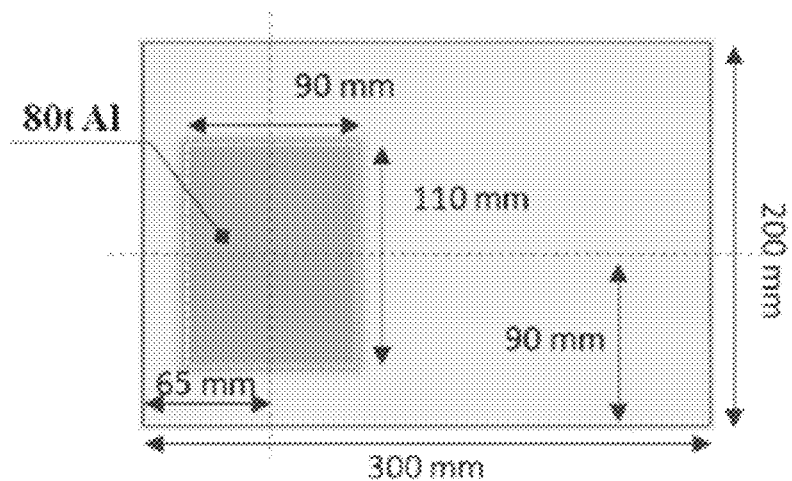
Figure 25B:
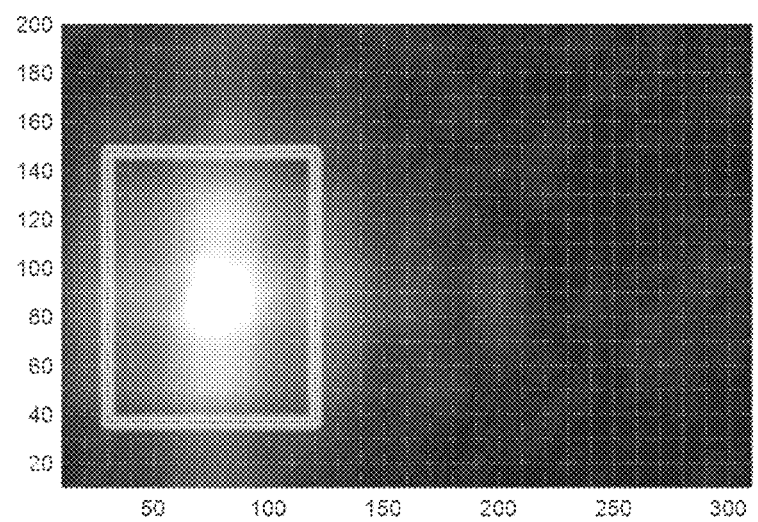
Figure 25C:
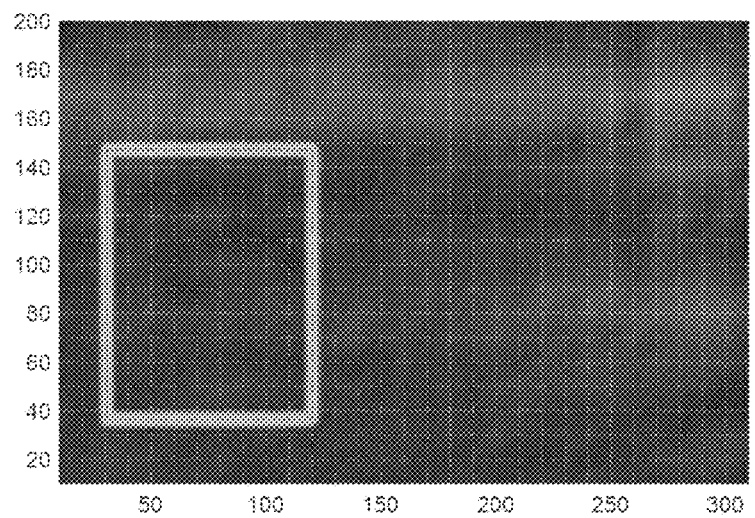
Figure 25D:
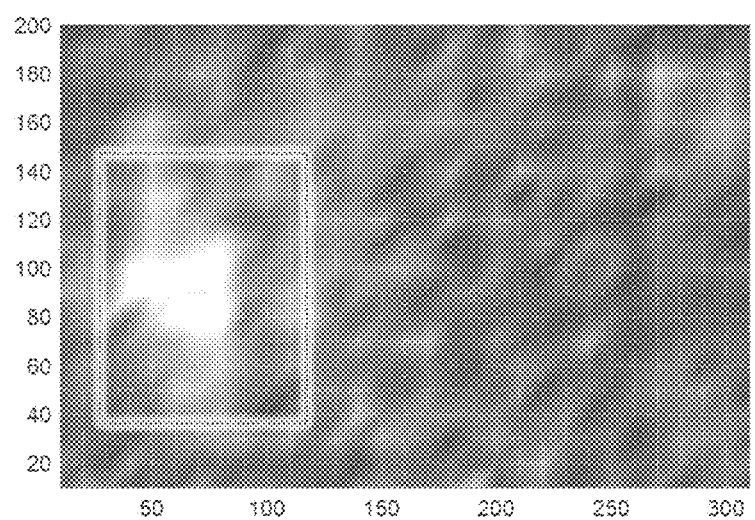

First, FIGS. 21 and 22 illustrate the two-dimensional imaging experiment environment. In FIGS. 21 and 22, A is a water tank used as an experimental environment, and B is an imaging object. In addition, C is an obstacle, and D corresponds to the ultrasonic transmission member 100 of the ultrasonic transmission apparatus 1 according to an embodiment of the present disclosure. In addition, E is a receiver/transmitter, and F corresponds to an imaging plane.

FIGS. 23A to 23D, FIGS. 24A to 24D, FIGS. 25A to 25D each illustrate a time when the imaging object with an experimental condition includes one original plate (FIGS. 23A to 23D), a time when the imaging object includes two original plates (FIGS. 24A to 24D), and a time when the imaging object includes a square plate (FIGS. 25A to 25D). In each case, a of each figure illustrates an imaging object, b of each figure illustrates a case in which there is no obstacle, c of each figure illustrates a case in which an obstruction is installed, and d of each figure illustrates a case in which the ultrasonic transmission members 100 is installed.

As illustrated in b of each figure, when there is no obstacle, a result that all imaging objects may be identified is derived. However, when an obstacle is installed as illustrated in c of each figure, it can be seen that identification of the imaging object is almost impossible due to a low transmittance. In addition, as illustrated in d of each figure, when the ultrasonic transmission members 100 is installed, it can be seen that an imaging result with a relatively identifiable degree may be obtained.

4. Effects and Application Scope of the Present Disclosure

According to the ultrasonic transmission apparatus 1 and the wave control method according to the present disclosure, high ultrasonic energy may be transferred across an obstacle due to a resonance phenomenon between the obstacle and the ultrasonic transmission member 100 by placing the ultrasonic transmission member 100 at a predetermined distance in front of the obstacle.

In addition, according to the ultrasonic transmission apparatus 1 and the wave control method according to the embodiment of the present disclosure, it is possible to transmit very high ultrasonic energy (maximum 100%) at a desirable frequency regardless of a type and a thickness of an obstacle.

The ultrasonic transmission apparatus 1 and the wave control method according to the present disclosure may be widely used for underwater ultrasonic waves, acoustics, medical ultrasonic waves, a non-destructive inspection, and so on, which require ultrasonic energy transfer. In addition, according to the ultrasonic transmission apparatus 1 and the wave control method according to the present disclosure, a signal measured on an opposite side of an obstacle may also be transferred with a very high transmittance, and thus, the present disclosure may be used for detection and precise detection of an underwater acoustic technology, a medical ultrasonic technology, and a non-destructive inspection technology.

26 to 28 illustrate implementation examples of an ultrasonic transmission apparatus 1 according to an embodiment of the present disclosure.

When the ultrasonic transmission apparatus 1 according to the embodiment of the present disclosure is installed, only that part is transmitted, so that the wave field opposite to the obstacle may be adjusted using this.

Figure 26:
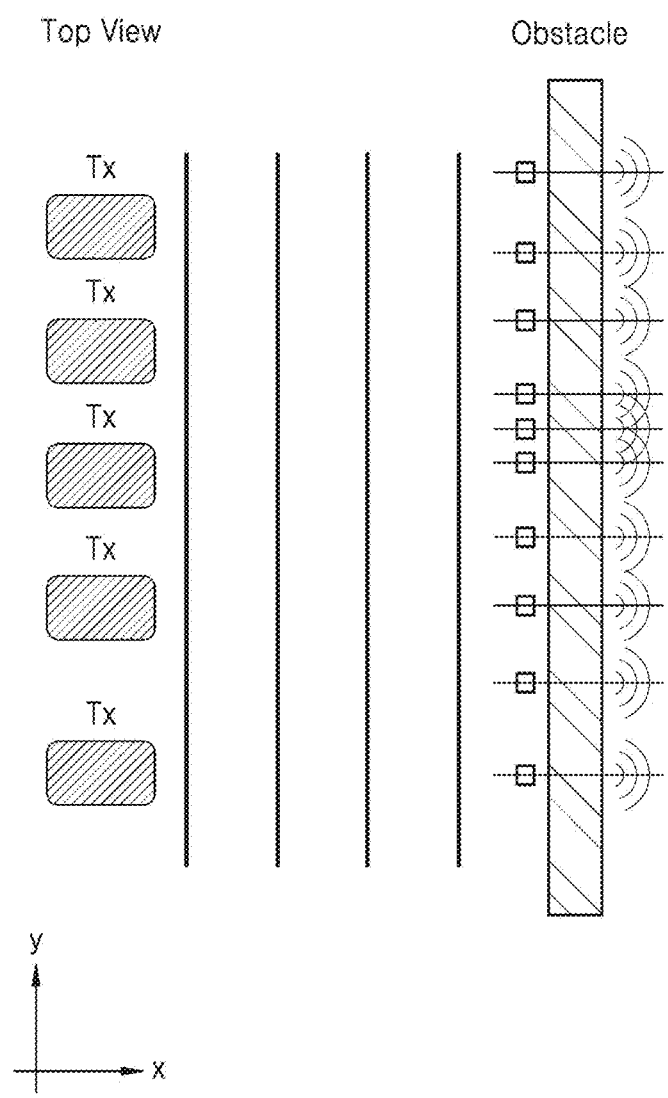
FIGS. 26 to 28 illustrate implementation examples of an ultrasonic transmission apparatus according to an embodiment of the present disclosure.
Figure 27A:
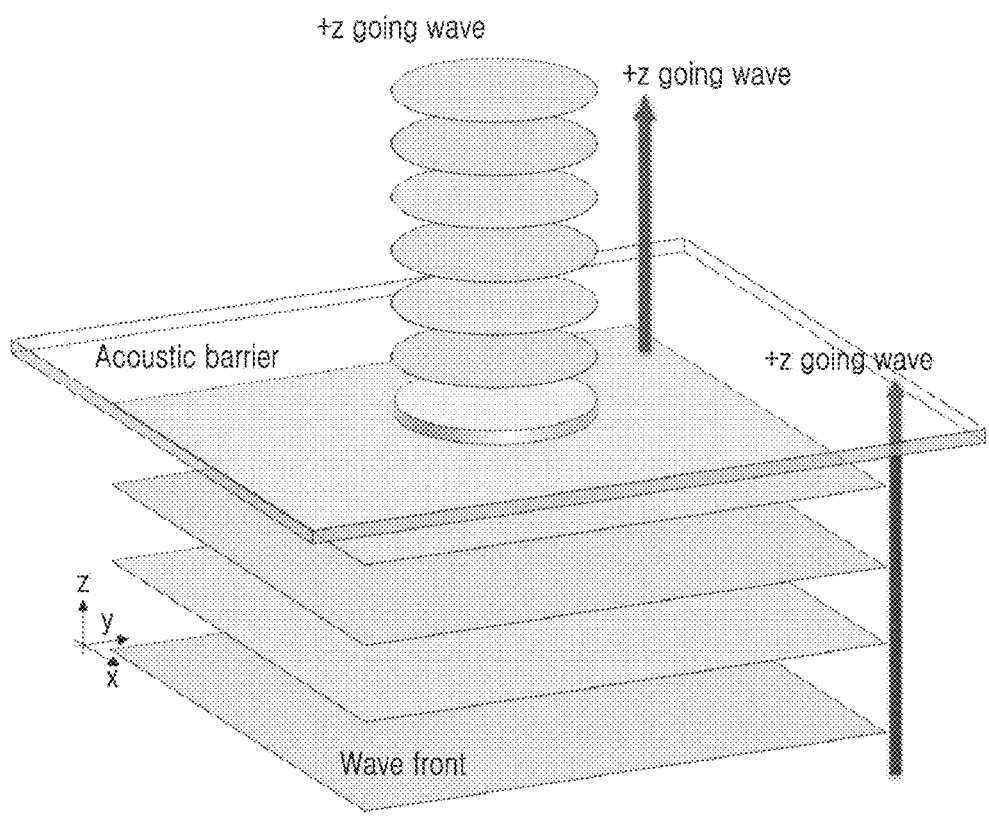
Figure 27B:
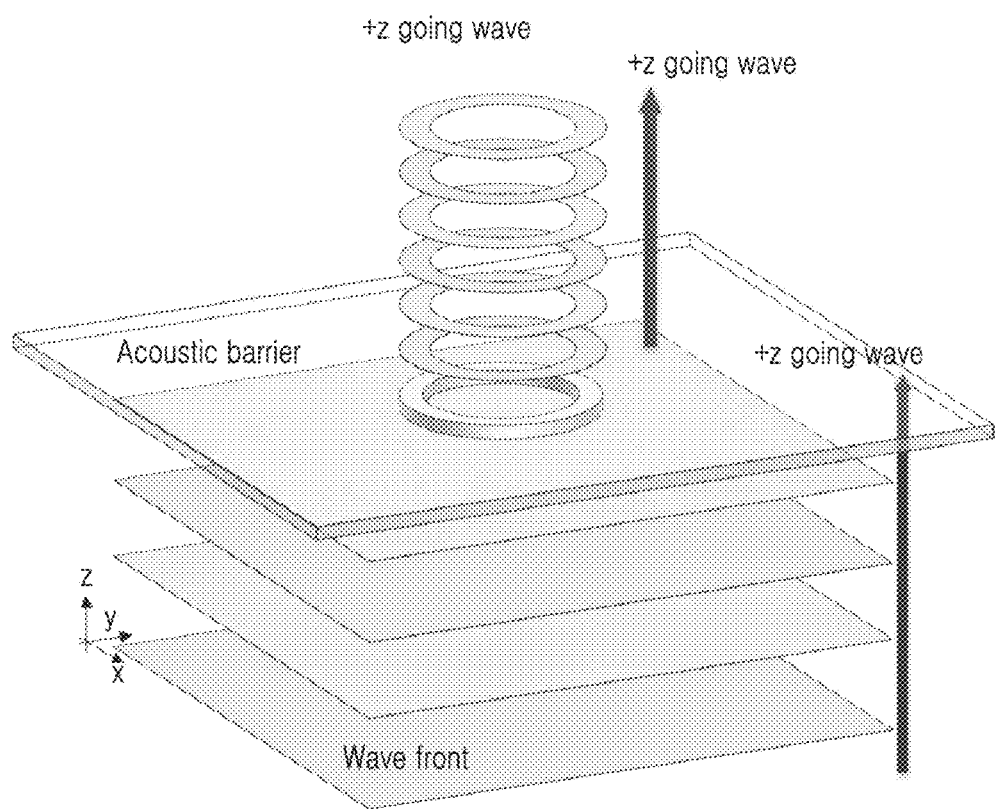
Figure 27C:
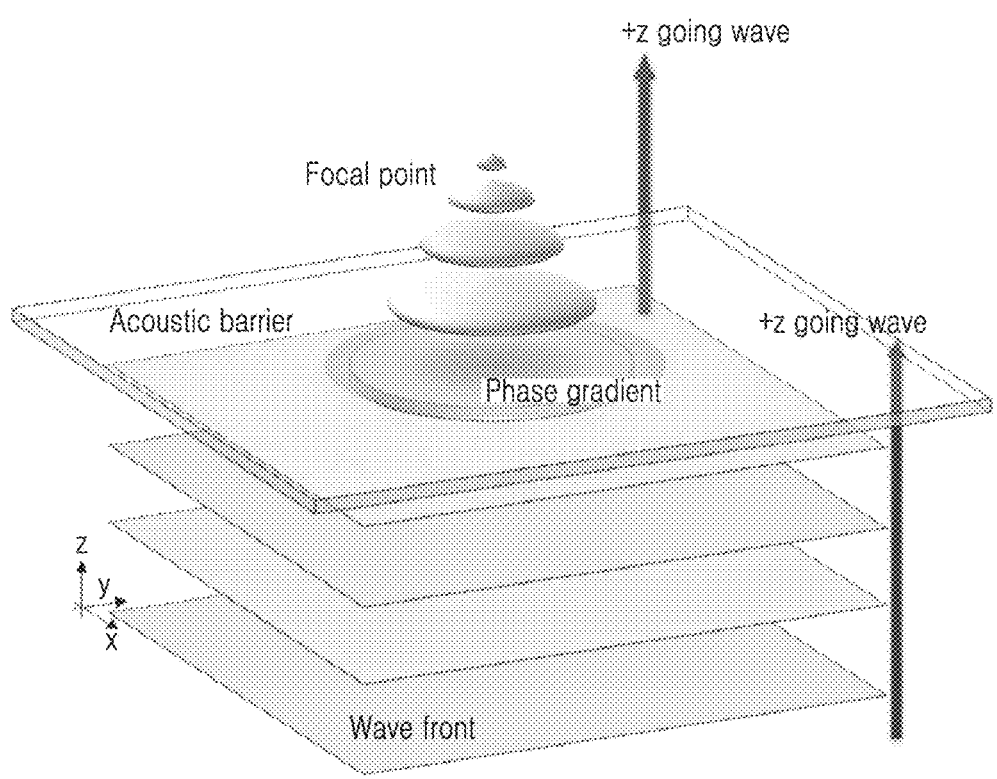
Figure 28:
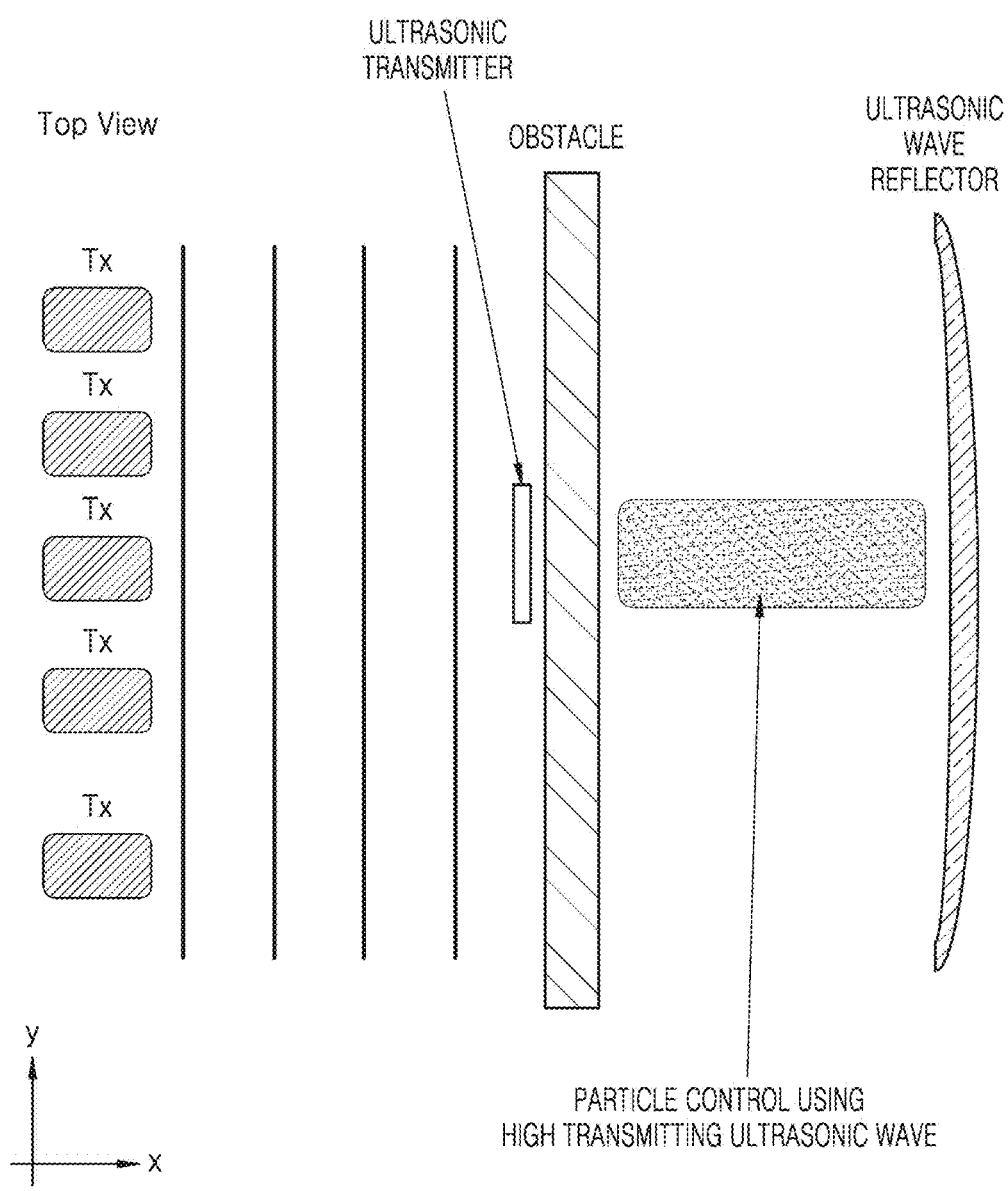

That is, by adjusting the phase of the wave, the present disclosure may be configured as a single phase arrangement system. As illustrated in FIGS. 26 to 28, the ultrasonic transmission apparatus 1 may be manufactured in various shapes to form waves of various shapes. Accordingly, the ultrasonic transmission apparatus 1 may also be used to collect or disperse materials on the other side of an obstacle, and high-energy waves on the other side of the obstacle may be applied to a system that requires transmission. For example, when the ultrasonic transmission apparatus 1 according to the embodiment of the present disclosure is used, it is easy to generate ultrasonic cavitation, so the present disclosure may be used in various places such as ultrasonic lithotripsy, cleaning purposes in industrial fields, and increasing drug reactions using ultrasonic waves in academia.

5. Extended Magnitude Matching Condition and Extended Phase Matching Condition

<Concepts of Extended Magnitude Matching Condition and Extended Phase Matching Condition>

Figure 29:
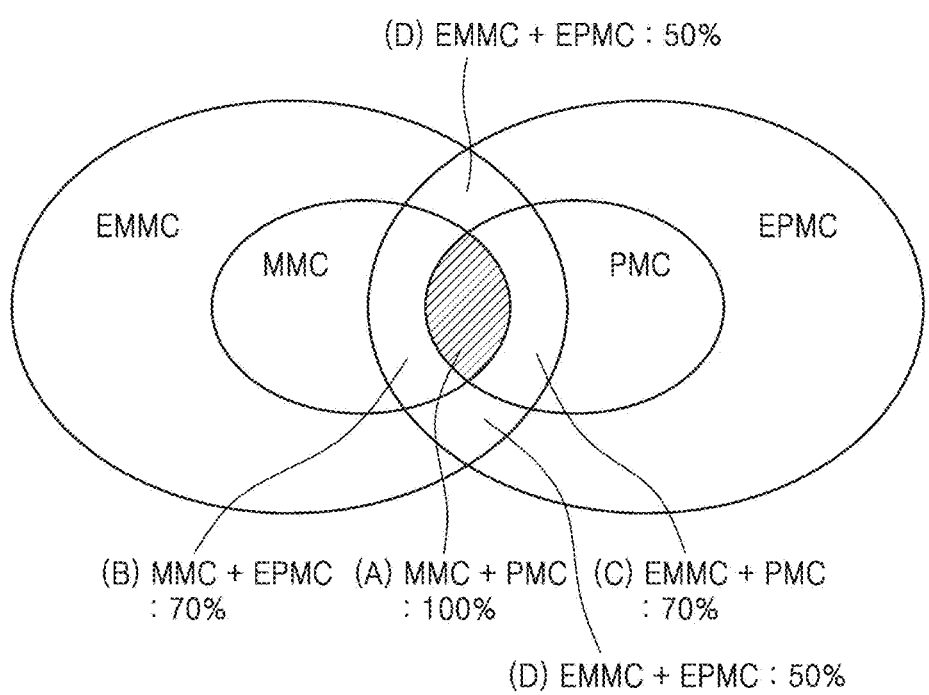
FIG. 29 is a diagram illustrating an extended magnitude matching condition and an extended phase matching condition.

FIG. 29 is a diagram illustrating a relationship between a magnitude matching condition (MMC), a phase matching condition (PMC), an extended magnitude matching condition (EMMC), and an extended phase matching condition (EPMC).

As described above, the phase matching condition is a condition that satisfies Equation (7), and the magnitude matching condition is a condition that satisfies Equation (8).

$$d_0 = \frac{\varphi_0}{k_0} = \frac{c_{p0}}{2\omega} \angle X(\alpha, \beta) \qquad \text{Equation (7)}$$

$$1 = |X(\alpha, \beta)| \qquad \text{Equation (8)}$$

When the phase matching condition and the magnitude matching condition are simultaneously satisfied, a largest value of a transmittance becomes 100%. This is the same as (A) of FIG. 29.

However, a range of condition that simultaneously satisfies the phase matching condition and the magnitude matching condition is very limited.

Accordingly, a distance of an ultrasonic transmission member capable of achieving a meaningful transmittance (an effective transmittance) is referred to as an extended phase matching condition, and a range of physical properties of the ultrasonic transmission member is referred to as an extended magnitude matching condition.

Hereinafter, the extended phase matching condition and the extended magnitude matching condition will be described. α and β used below are the same as described above. That is, a ratio between a phase of an obstacle and a phase of the ultrasonic transmission member is defined as α, and a ratio between impedance of the obstacle and impedance of the ultrasonic transmission member is defined as β.

<Expanded Phase Matching Condition (EPMC)>

An extended phase matching condition is described as follows.

As described above, when both the phase matching condition (PMC) and the magnitude matching condition (MMC) are satisfied, a transmittance of an ultrasonic transmission member becomes 100%.

The extended phase matching condition is derived by using a transmittance when a distance d between the obstacle A3 and the ultrasonic transmission member 100 is varied. When the highest transmittance (that is, a transmittance when the ultrasonic transmission member 100 is at a position that satisfies the phase matching condition) that may be exhibited by the ultrasonic transmission member 100 with certain physical properties is defined as T, the extended phase matching condition indicates a range of d in which a transmittance of more than a meaningful transmittance (effective transmittance) may be achieved based on T.

In other words, when the ultrasonic transmission member 100 is placed at a certain position and a distance between the ultrasonic transmission member 100 and the obstacle A3 has a certain value, although a value of the transmittance exhibited by the ultrasonic transmission member 100 is not T, when a transmittance greater than the meaningful transmittance (effective transmittance) is achieved, it can be described that a distance between an ultrasonic transmission member and an obstacle satisfies the extended phase matching condition.

In the present disclosure, the effective transmittance is defined as a transmittance of 70%. That is, a range of a distance between an ultrasonic transmission member and an obstacle, which may achieve a transmittance of 0.7 T or more, is set as a range that satisfies the extended phase matching condition.

Figure 30A:
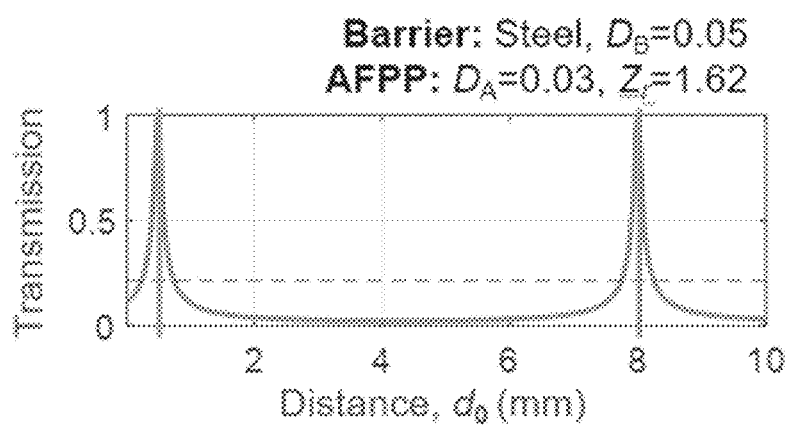
FIGS. 30A and 30B illustrate a comparison and a contrast between a range of d that satisfies the phase matching condition and a range of d that satisfies the extended phase matching condition.
Figure 30B:
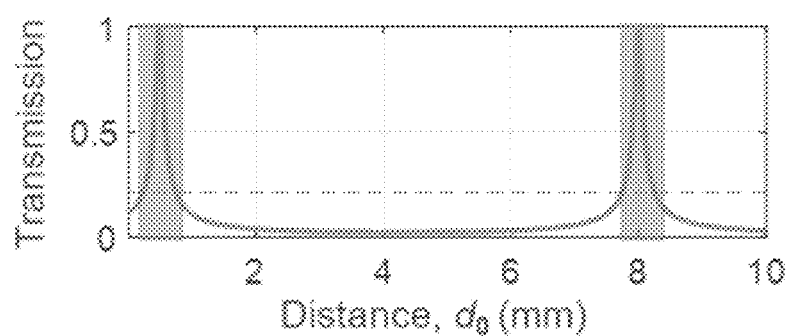

FIGS. 30A and 30B illustrate a comparison and a contrast between the range of d that satisfies a phase matching condition and a range of d that satisfies an extended phase matching condition. The range of d that satisfies the phase matching condition illustrated in FIG. 30A is limited to one point (a distance with a specific value). In contrast to this, it can be seen that the range of d that satisfies the extended phase matching condition illustrated in FIG. 30B is within a shaded range and has a certain distance range.

The extended phase matching condition is represented by following Equation (9). The extended phase matching condition is obtained by modifying a conditional equation for the phase matching condition described above.

$$\frac{c_{p0}}{2\omega}LX(\alpha,\beta) - \eta_{EPMC} \le d_0 \le \frac{c_{p0}}{2\omega}LX(\alpha,\beta) + \eta_{EPMC} \quad \text{Equation (9)}$$

Here, $\eta_{EPMC}$, which expresses a range of the extended phase matching condition, may be represented by Equation (10). This is a value obtained through parameter study.

$$\eta_{EPMC} = 0.655 \times (1 - |R_B|) \quad \text{Equation (10)}$$

Here, $R_B$ is as follows as described above.

$$R_B = \frac{-\frac{i}{2}\left(\frac{z_0}{z_B} - \frac{z_B}{z_0}\right)\sin(\varphi_B)}{\cos(\varphi_B) + \frac{i}{2}\left(\frac{z_0}{z_B} + \frac{z_B}{z_0}\right)\sin(\varphi_B)}$$

Figure 31:
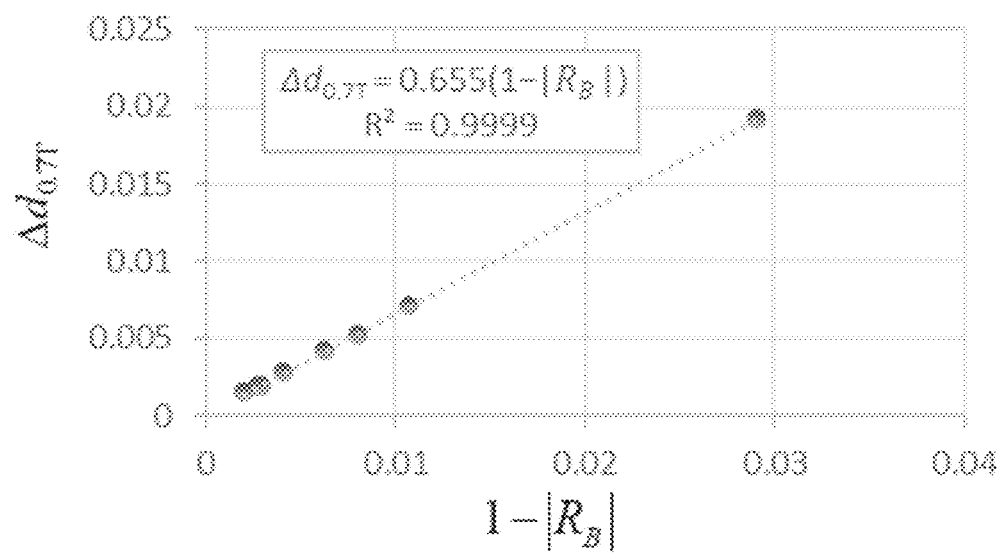
FIG. 31 illustrates a region of a distance d that satisfies the extended phase matching condition.
Figure 32A:
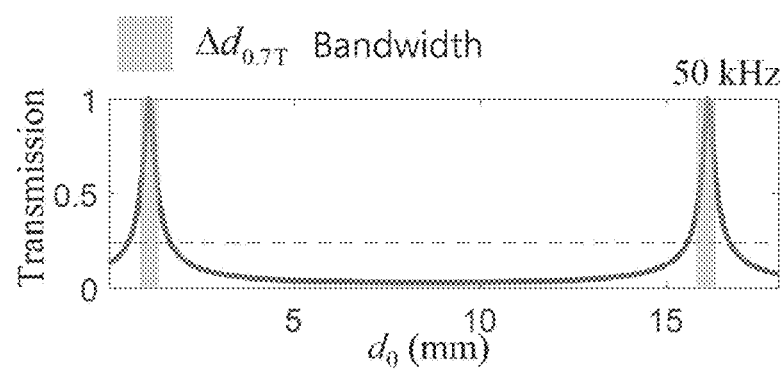
FIGS. 32A to 32G are examples in which the extended phase matching condition is applied to an iron obstacle of 5 mm in water.
Figure 32B:
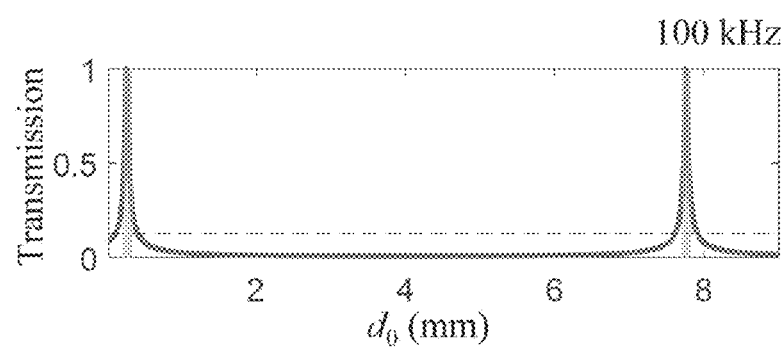
Figure 32C:
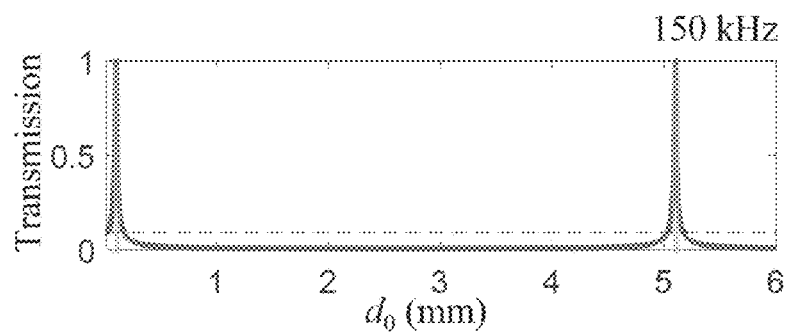
Figure 32D:
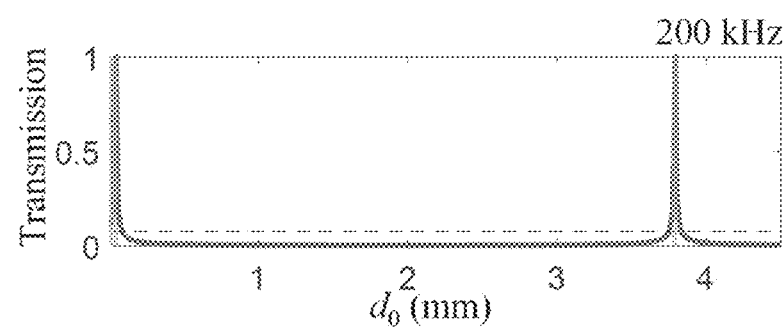
Figure 32E:
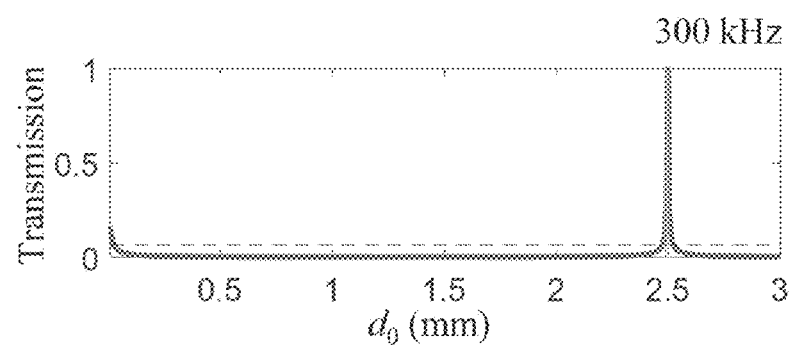
Figure 32F:
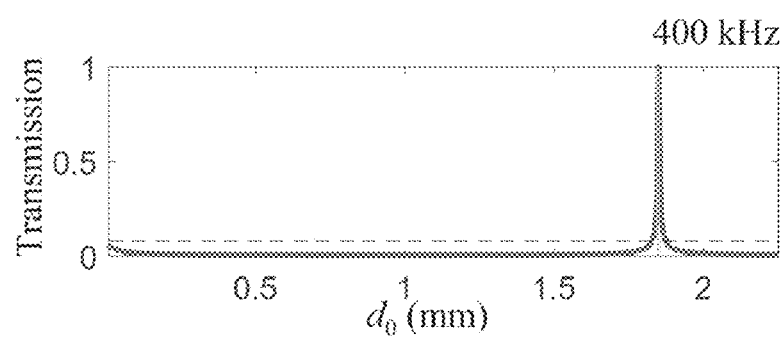
Figure 32G:
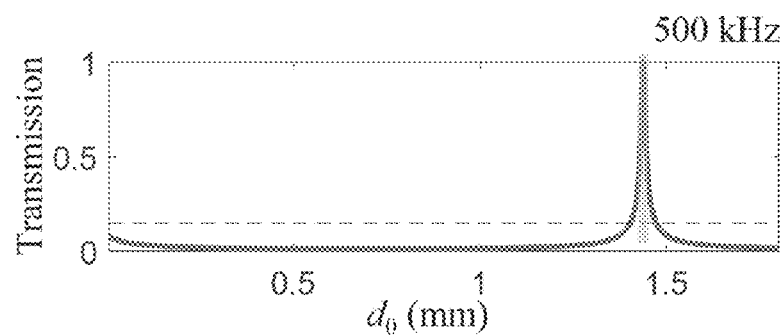

FIG. 31 illustrates a region of the distance d that satisfies the extended phase matching condition. As illustrated in FIG. 31, it can be seen that $\Delta d_{0.7T}$ representing a region of a distance $d_0$ in which a transmittance of 0.7 T or more may be secured has a linearly proportional relationship. In fact, when the extended phase matching condition is applied to an iron obstacle of 5 mm in water, regions represented by a gray shade in FIGS. 32A to 32G may be predicted.

<Expanded Magnitude Matching Condition (EMMC)>

An extended magnitude matching condition is described as follows.

As described above, when both the phase matching condition (PMC) and the magnitude matching condition (MMC) are satisfied, a transmittance of an ultrasonic transmission member becomes 100%.

When physical properties of the ultrasonic transmission member 100 are varied in a state where the phase matching condition is satisfied, the extended magnitude matching condition refers to ranges of $\alpha$ and $\beta$ in which a transmittance is not 100% but a transmittance greater than a meaningful transmittance (effective transmittance) may be achieved.

In other words, this is as follows. Ultrasonic transmission members ($\alpha$ and $\beta$) with certain physical properties are selected, and an installation distance $d_0$ at which a transmittance may be the highest by using the selected ultrasonic transmission members is calculated according to a phase matching condition, and this is called a member highest transmittance. In this case, a condition that the member highest transmittance satisfies ranges of $\alpha$ and $\beta$ in which an effective transmittance may be achieved may be described as the extended magnitude matching condition.

In the present disclosure, the effective transmittance is defined as a transmittance of 70%. That is, when the phase matching condition is satisfied, ranges of $\alpha$ and $\beta$ that may achieve a transmittance of 0.7 T or more are taken as a range that satisfies the extended magnitude matching condition.

Figure 33A:
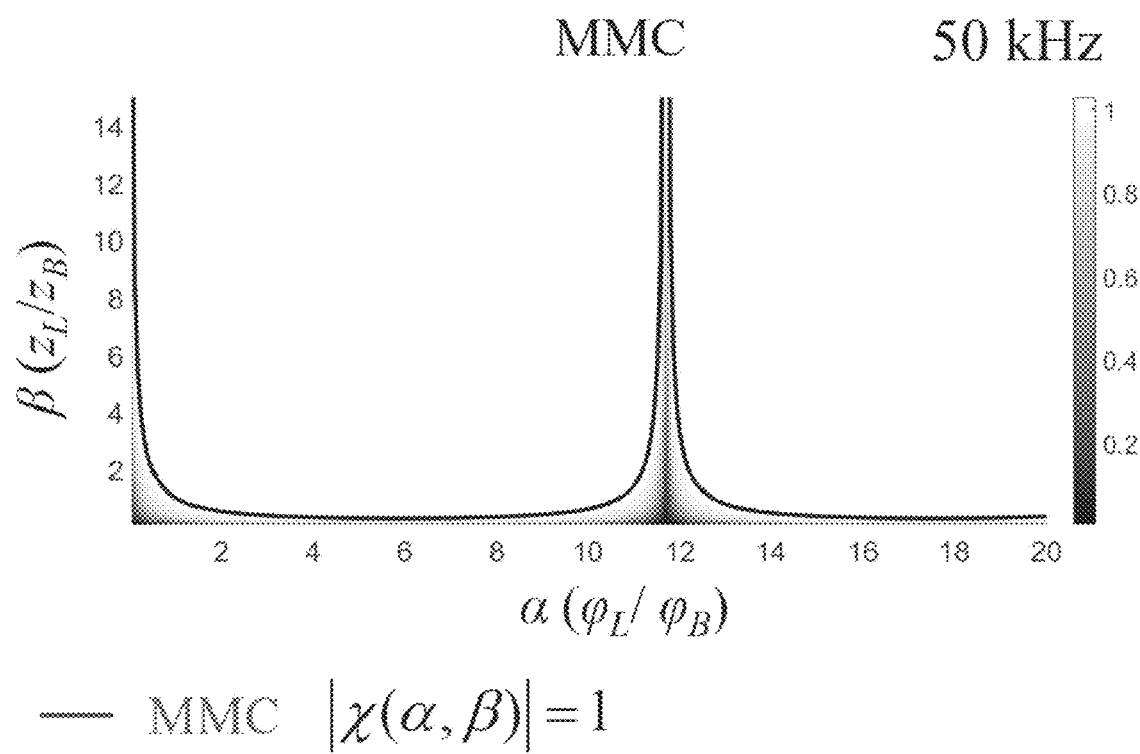
FIGS. 33A and 33B illustrate a comparison and a contrast between ranges of α and β that satisfy the magnitude matching condition and ranges of α and β that satisfy the extended magnitude matching condition.
Figure 33B:
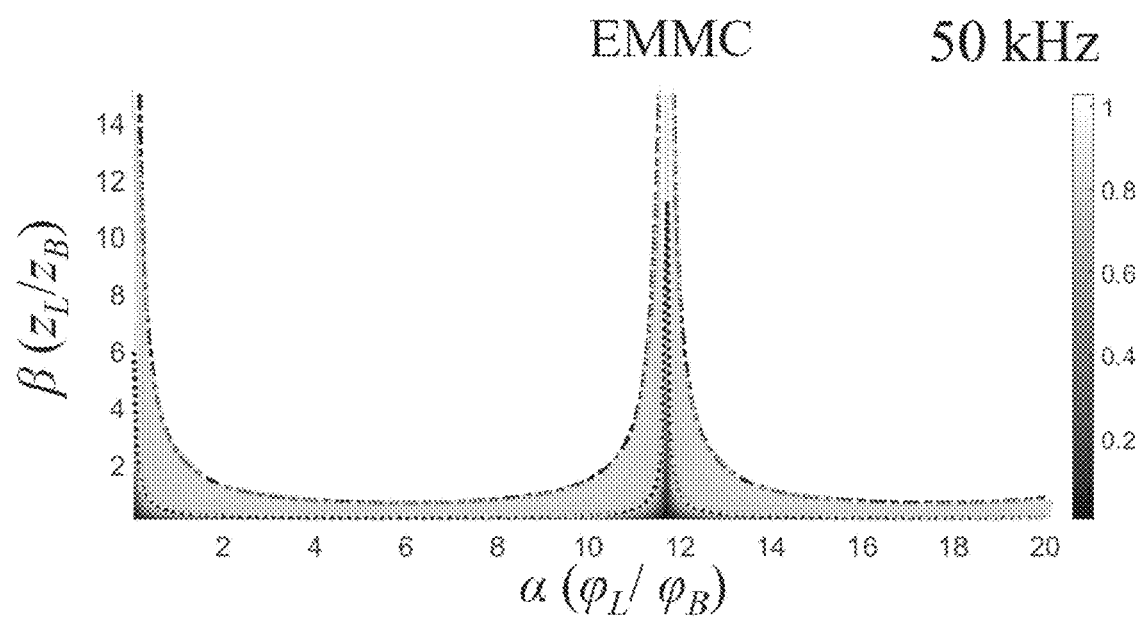
Figure 34A:
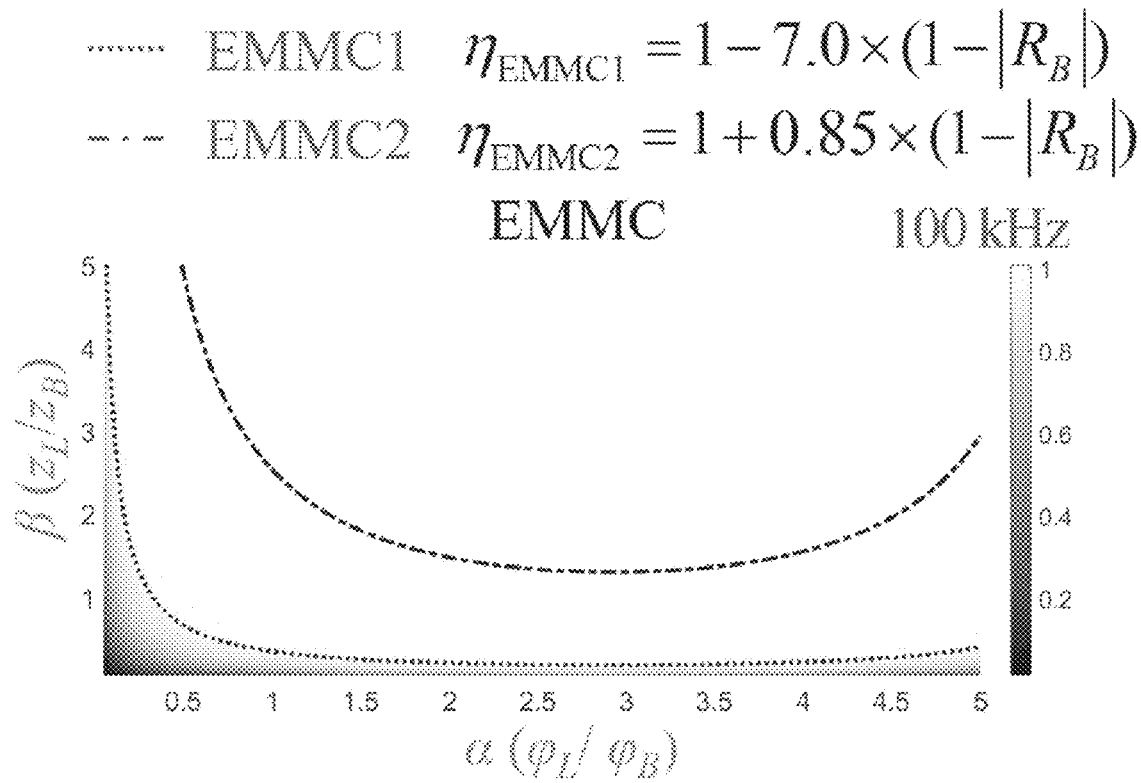
FIGS. 34A to 34H and FIGS. 35A to 35H illustrate transmittance diagrams for an iron obstacle and an aluminum obstacle and the extended magnitude matching condition.
Figure 34B:
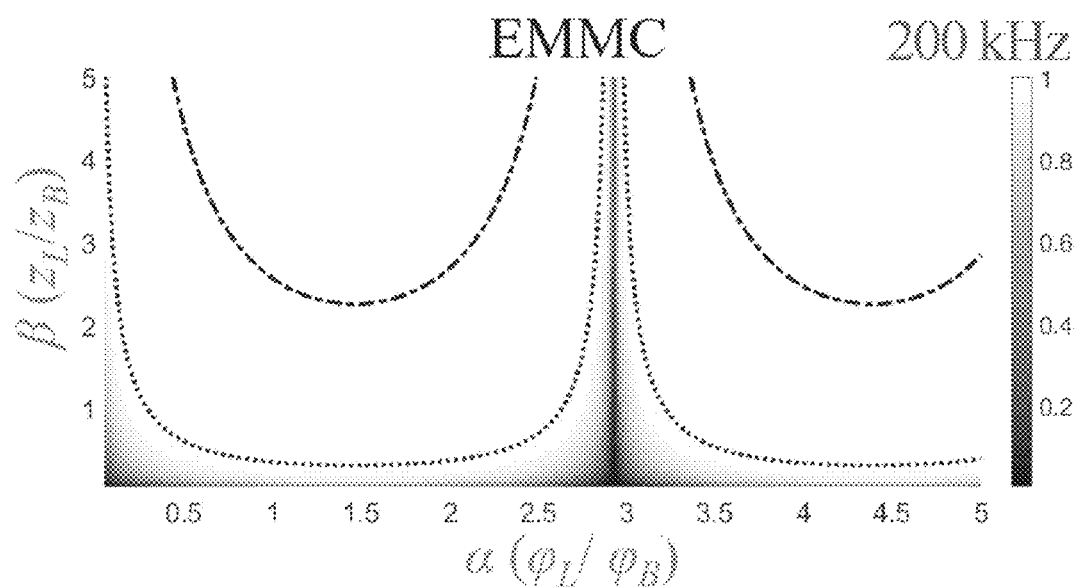
Figure 34C:
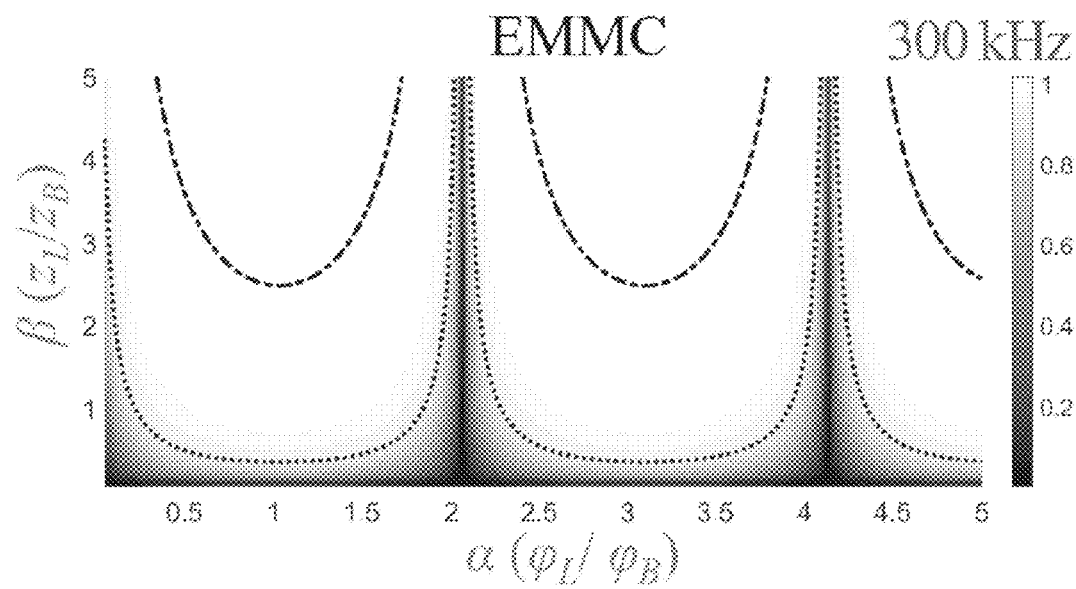
Figure 34D:
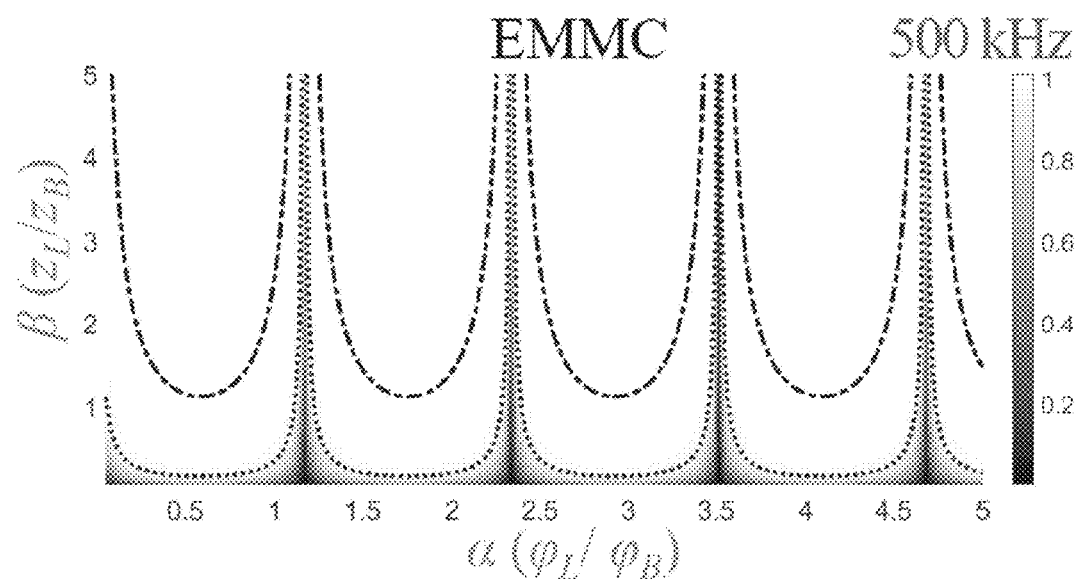
Figure 34E:
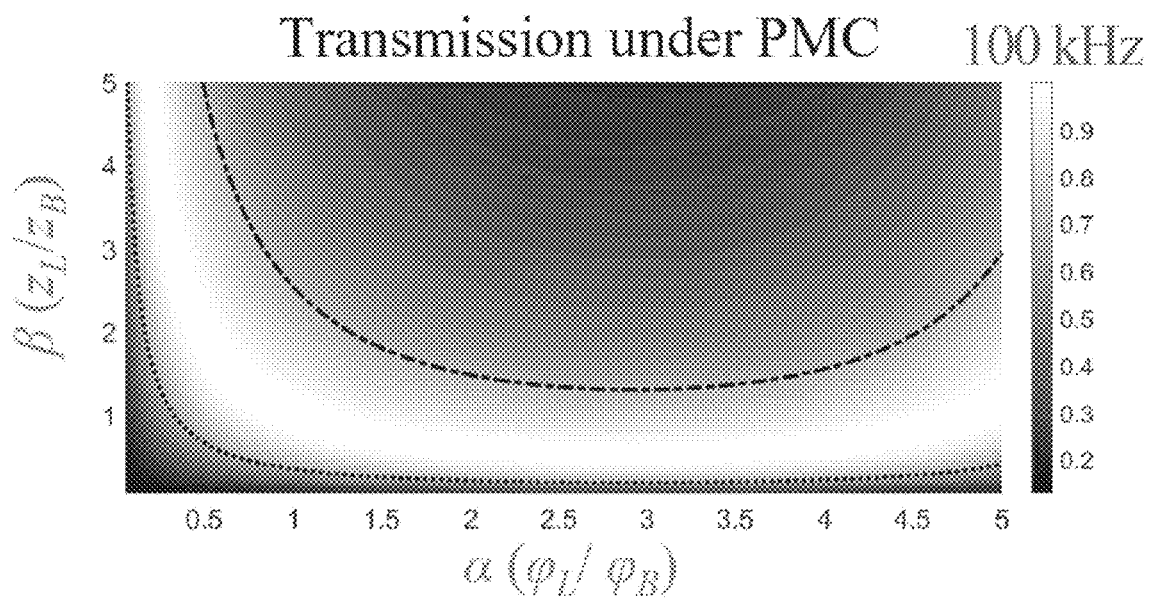
Figure 34F:
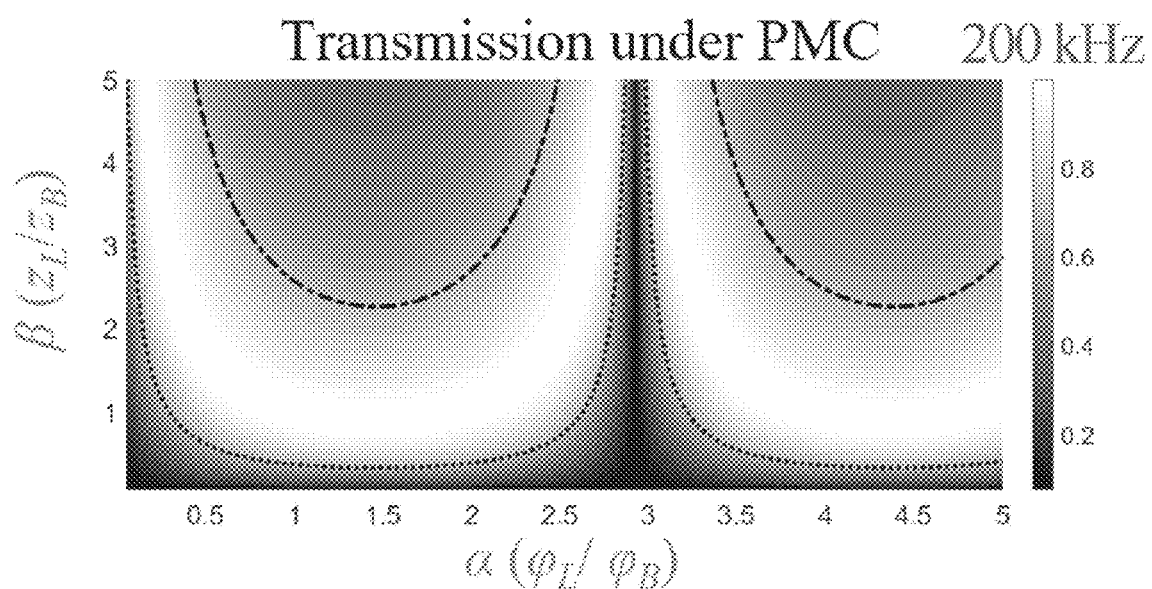
Figure 34G:
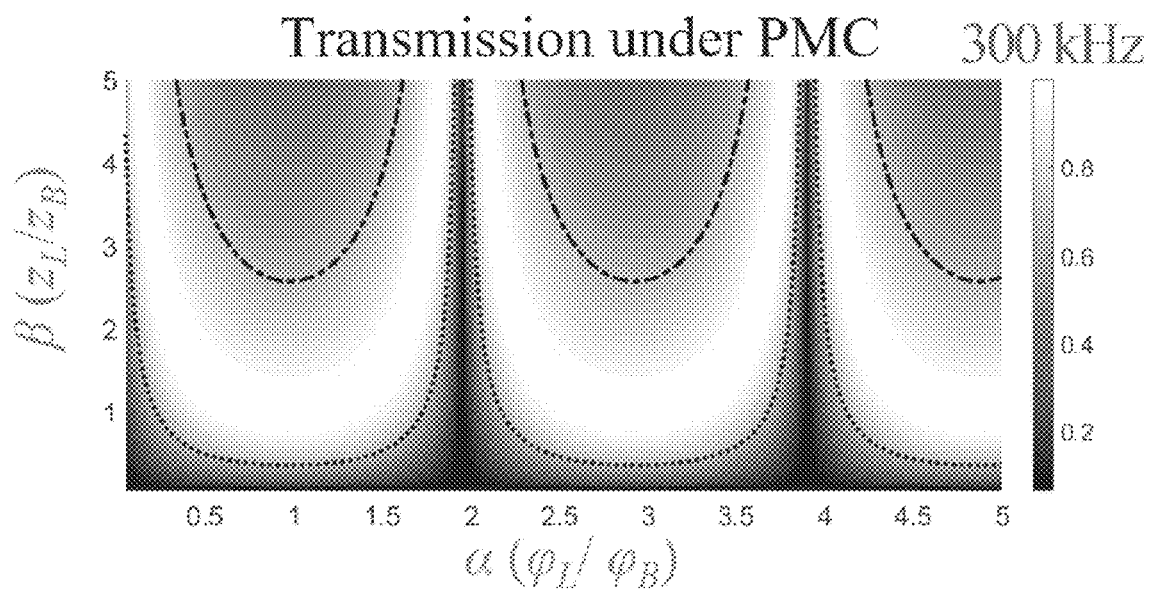
Figure 34H:
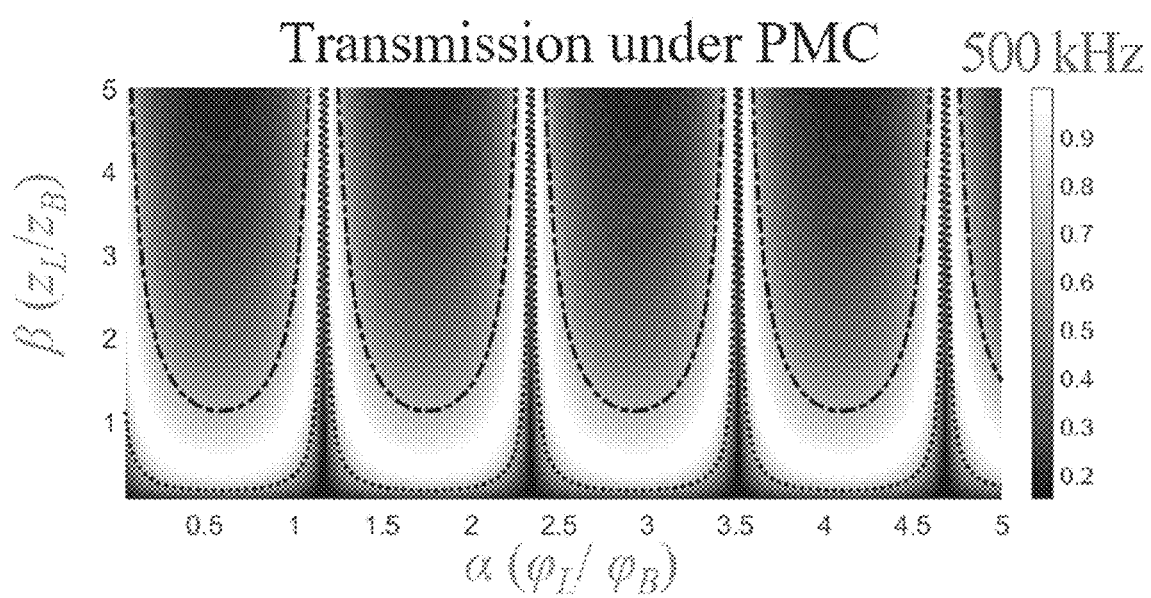
Figure 35A:
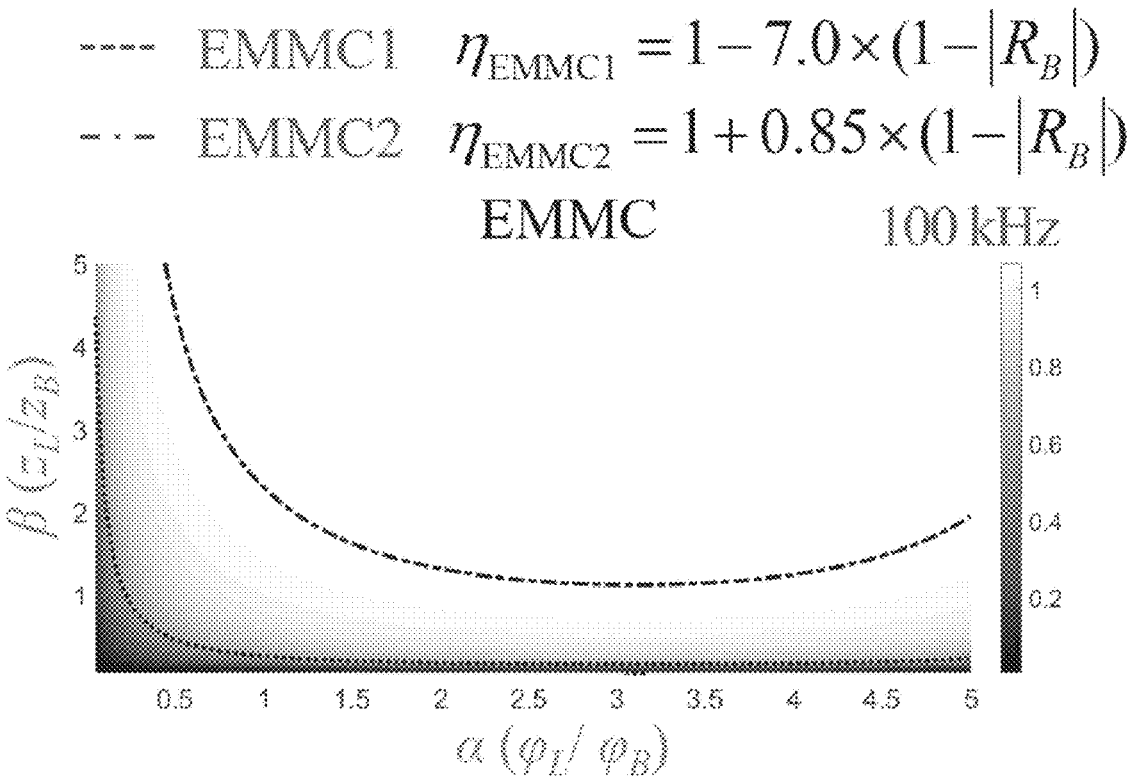
Figure 35B:
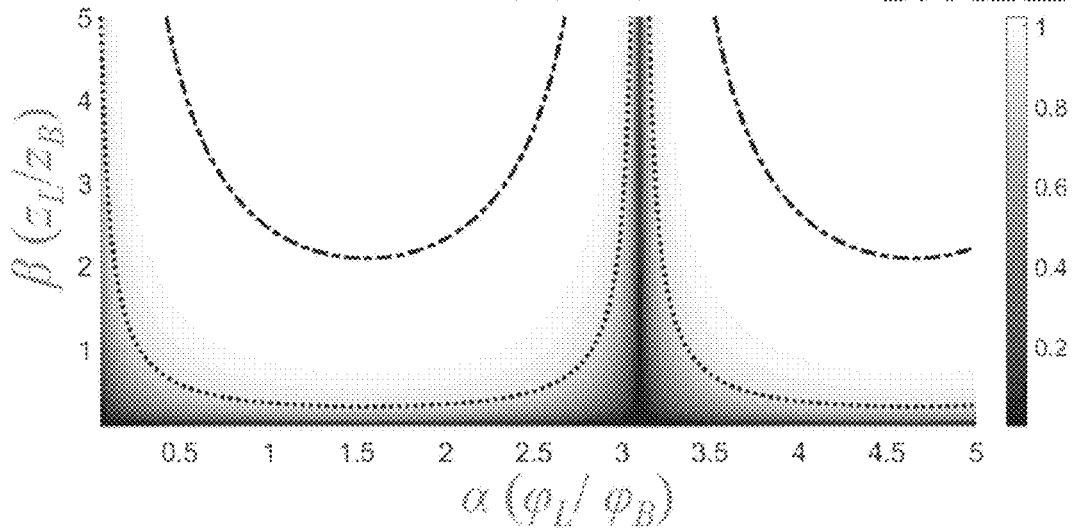
Figure 35C:
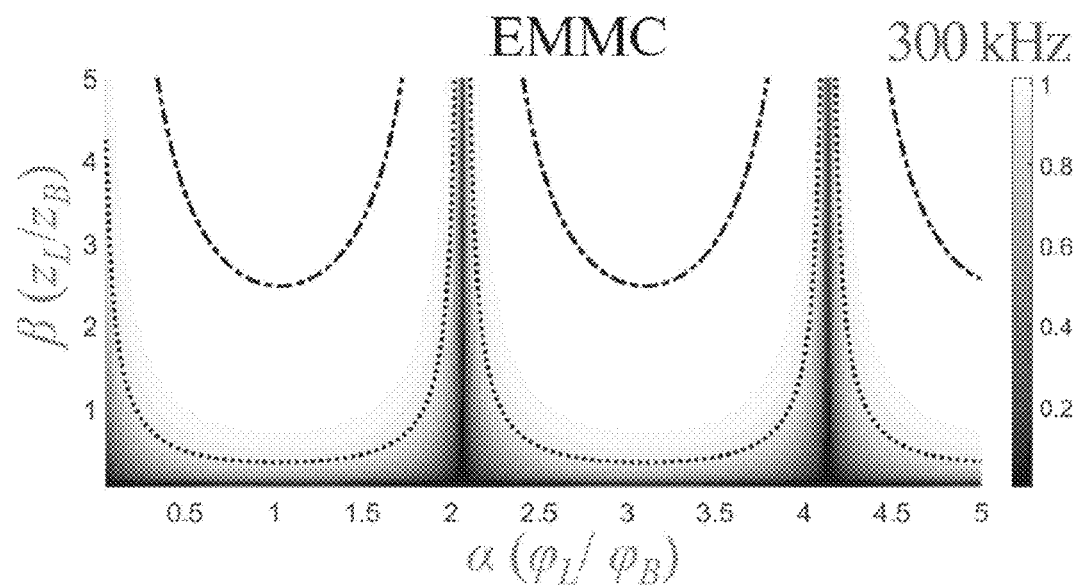
Figure 35D:
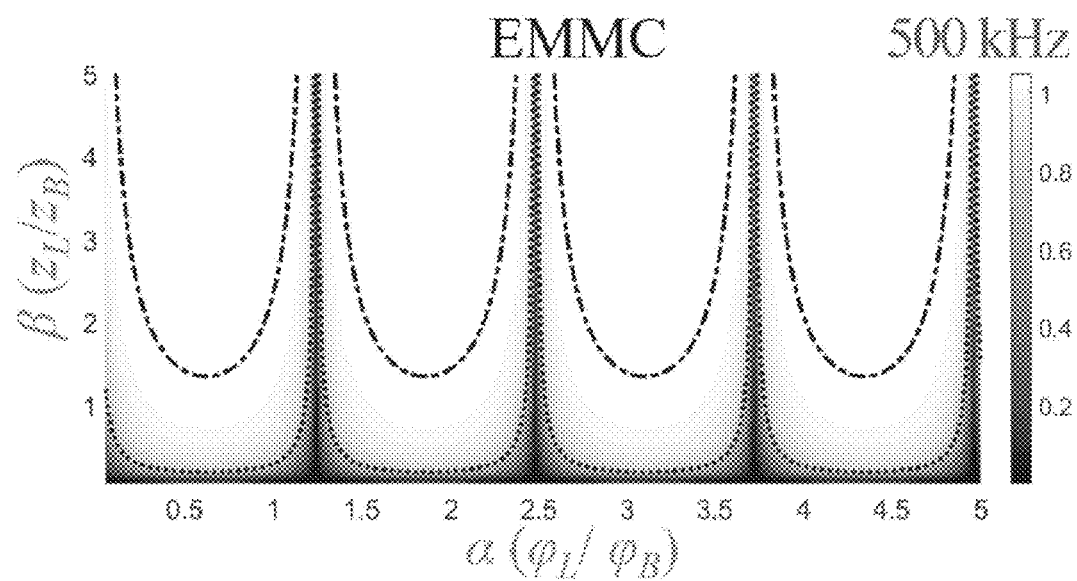
Figure 35E:
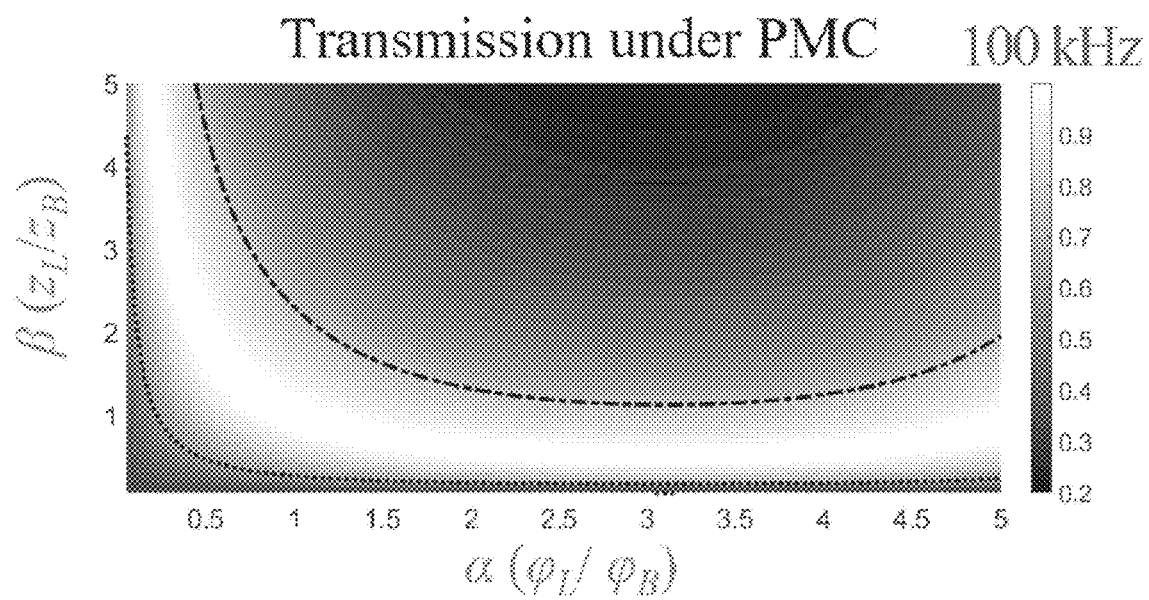
Figure 35F:
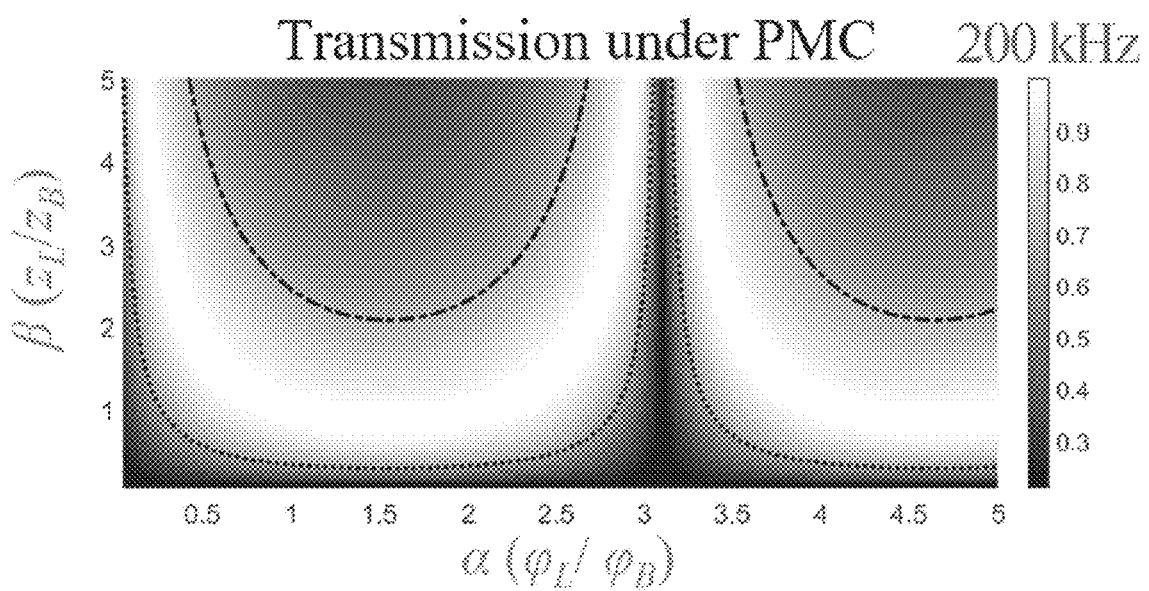
Figure 35G:
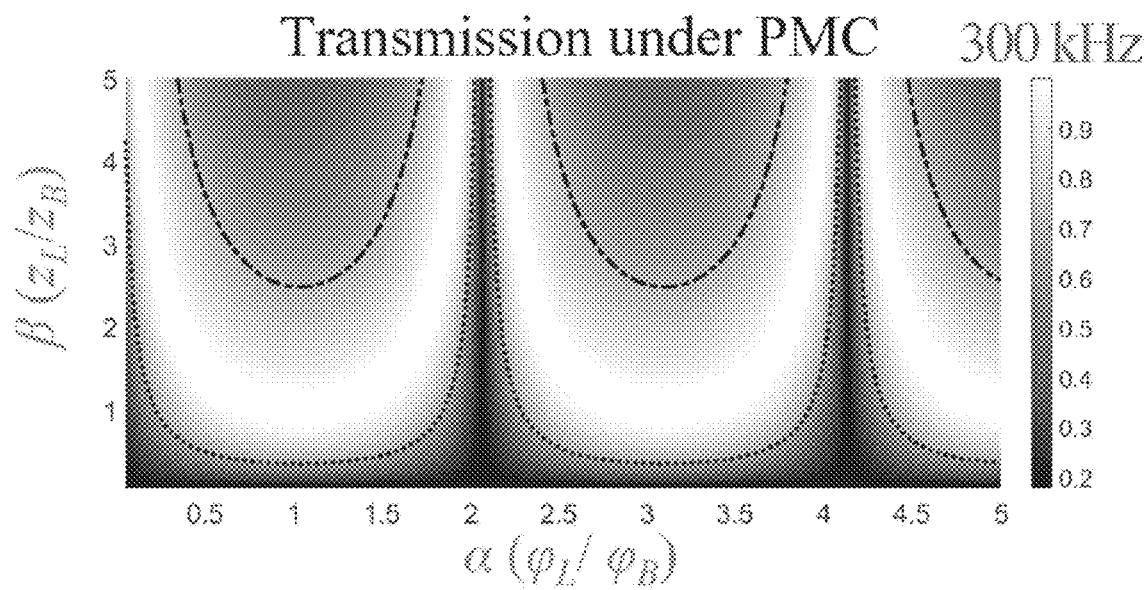
Figure 35H:
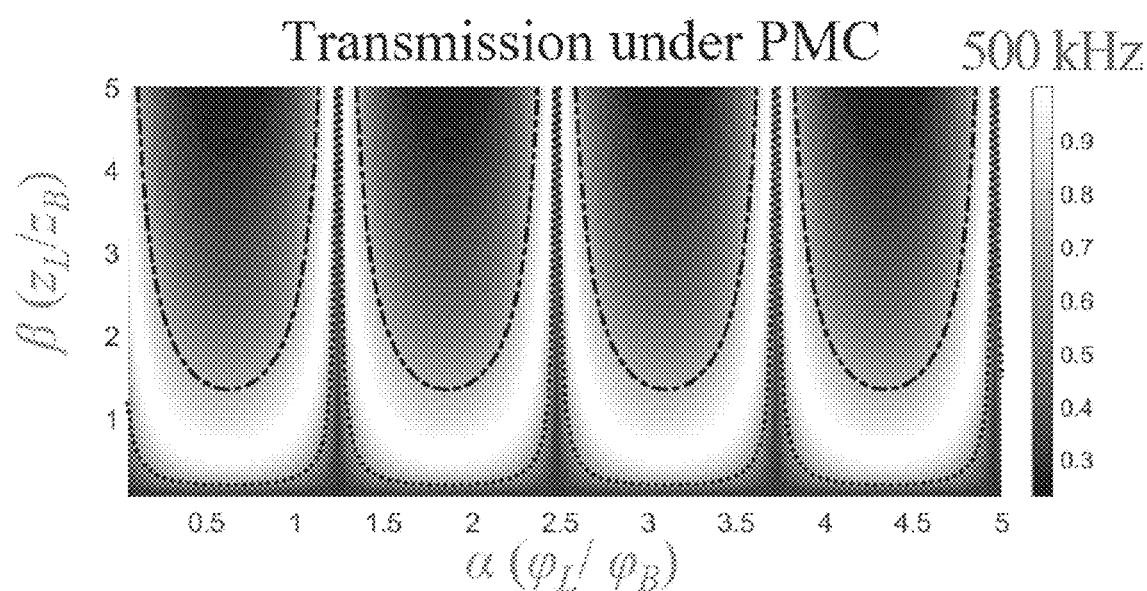

33A and 33B illustrate a comparison and a contrast between ranges of $\alpha$ and $\beta$ that satisfy the magnitude matching condition and ranges of $\alpha$ and $\beta$ that satisfy the expanded magnitude matching condition. The ranges of $\alpha$ and $\beta$ that satisfy the magnitude matching condition illustrated in FIG. 33A are limited by a solid line. In contrast to this, it can be seen that the ranges of $\alpha$ and $\beta$ that satisfy the extended magnitude matching condition illustrated in FIG. 33B have a certain area as a region in a dashed-dotted line and a dashed line.

The extended magnitude matching condition is represented by following Equation (11). The extended magnitude matching condition is obtained by modifying a conditional equation for the magnitude matching condition described above.

$$\eta_{EMMC1} \le |\chi(\alpha,\beta)| \le \eta_{EMMC2} \quad \text{Equation (11)}$$

Here, $\eta_{EMMC1}$ and $\eta_{EMMC2}$ representing a range of the extended magnitude matching condition may be represented by following Equation (12) and Equation (13), respectively. $R_B$ constituting Equation (12) and Equation (13) is represented by Equation (14). Equation (12), Equation (13), and Equation (14) calculate conditions representing a transmittance of about 70% or more for various obstacles through parameter study.

$$\eta_{EMMC1} = 1 - 7.0 \times (1 - |R_B|) \quad \text{Equation (12)}$$

$$\eta_{EMMC2} = 1 + 0.85 \times (1 - |R_B|) \quad \text{Equation (13)}$$

$$R_B = \frac{-\frac{i}{2}\left(\frac{z_0}{z_B} - \frac{z_B}{z_0}\right)\sin(\varphi_B)}{\cos(\varphi_B) + \frac{i}{2}\left(\frac{z_0}{z_B} + \frac{z_B}{z_0}\right)\sin(\varphi_B)} \quad \text{Equation (14)}$$

FIGS. 34A to 34H and FIGS. 35A to 35H illustrate transmittance diagrams and extended magnitude matching conditions for iron and aluminum obstacles, respectively.

In FIGS. 34A to 34H and FIGS. 35A to 35H, EMMC1 is indicated by a dashed line and EMMC2 is indicated by a dashed-dotted line. Overall, EMMC is a range in which a region surrounded by a line represented by EMMC1 and a line represented by EMMC2 satisfies the expanded magnitude matching condition. It can be seen that, when the condition of the above-described range is satisfied, a transmittance is about 70% or more.

<Combination of Extended Phase Matching Condition and Extended Magnitude Matching Condition>

Hereinafter, a relationship between an extended phase matching condition and an extended magnitude matching condition will be described with reference to FIG. 29 again.

As described above, when the phase matching condition and the magnitude matching condition are simultaneously satisfied, the highest transmittance value becomes 100%. This is the same as (A) of FIG. 29.

A case in which an ultrasonic transmission member that satisfies the magnitude matching condition (MMC) is at a position that satisfies the extended phase matching condition (EPMC) (MMC+EPMC) is the same as (B) of FIG. 29. Even in this case, it can be seen that a transmittance of 70% of the highest transmittance is achieved.

A case in which an ultrasonic transmission member with physical properties that satisfies the extended magnitude matching condition (EMMC) is at a position that satisfies the phase matching condition (PMC) (EMMC+PMC) is the same as (C) of FIG. 29. In this case, it can be seen that a transmittance of 70% of the highest transmittance is achieved.

Subsequently, a case in which the extended magnitude matching condition (EMMC) and the extended phase matching condition (EPMC) are satisfied is the same as (D) of FIG. 29. In this case, a transmittance (0.7×0.7) of about 50% of the highest transmittance may be achieved.

In the above description, preferred embodiments are illustrated and described, but the present disclosure is not limited to the specific embodiments described above, and various modifications may be implemented by those skilled in the technical field to which the present disclosure pertains without departing from the idea of the present disclosure claimed in the claims, and the modifications should not be individually understood from the technical idea or perspective of the present disclosure.

What is claimed is:

1. An ultrasonic transmission apparatus for performing an ultrasonic inspection by injecting an ultrasonic wave into an object including a medium and a body to be inspected inside and including an obstacle outside, the ultrasonic transmission apparatus comprising:
   an ultrasonic generation device configured to generate an incident wave; and
   an ultrasonic transmission module located between the obstacle and the ultrasonic generation device and located on a travel path of an incident wave generated by the ultrasonic generation device,
   wherein the ultrasonic transmission module comprises:
   an ultrasonic transmission member, and
   a position variable device configured to vary a position of the ultrasonic transmission member, and
   wherein the ultrasonic transmission member selectively varies impedance and a phase,
   a ratio $\alpha$ between a phase of the obstacle and a phase of the ultrasonic transmission member and a ratio $\beta$ between impedance of the obstacle and impedance of the ultrasonic transmission member are defined according to following Equation (1), $$\alpha \equiv \frac{\varphi_L}{\varphi_B} = \frac{k_L d_L}{k_B d_B}, \beta \equiv \frac{z_L}{z_B} \qquad \text{Equation (1)}$$

where $z=\rho c$ ($\rho$: density c: wave velocity),
$\Phi=kd$ (k: wavenumber, d: thickness of dissimilar material),
$k=\omega/c=$ ($\omega$: frequency [Rad/s]),
$\omega=2\pi f$ (f: frequency [Hz]),
the subscript 'B' indicates the obstacle, and the subscript 'L' indicates the ultrasonic transmitter.

2. The ultrasonic transmission apparatus of claim 1, wherein
   the position variable device varies a distance between the obstacle and the ultrasonic transmission member to cause a phase and a magnitude of a transmitted wave passing through the ultrasonic transmission member and the obstacle to be the same as a phase and a magnitude of the incident wave generated by the ultrasonic generation device.

3. The ultrasonic transmission apparatus of claim 1, wherein
   the ratio $\beta$ between the impedance of the obstacle and the impedance of the ultrasonic transmission member and the ratio $\alpha$ between the phase of the obstacle and the phase of the ultrasonic transmission member each satisfy following Equation (2), $$1 = |(\alpha, \beta)| \qquad \text{Equation (2)}$$

$$\left(\text{here}, \mathcal{X}(\alpha, \beta) \equiv R_B\left(R_L - \frac{T_L^2}{R_L}\right),\right.$$

$$R_B = \frac{-\frac{i}{2}\left(\frac{z_0}{z_B} - \frac{z_B}{z_0}\right)\sin(\varphi_B)}{\cos(\phi_B) + \frac{i}{2}\left(\frac{z_0}{z_B} + \frac{z_B}{z_0}\right)\sin(\varphi_B)},$$

$$R_L = \frac{-\frac{i}{2}\left(\frac{z_0}{z_L} - \frac{z_L}{z_0}\right)\sin(\varphi_L)}{\cos(\varphi_L) + \frac{i}{2}\left(\frac{z_0}{z_L} + \frac{z_L}{z_0}\right)\sin(\varphi_L)},$$

$$\left. T_L = \frac{1}{\cos(\varphi_L) + \frac{i}{2}\left(\frac{z_0}{z_L} + \frac{z_L}{z_0}\right)\sin(\varphi_L)}\right)$$

the subscript '0' indicates the progress medium, the subscript 'B' indicates the obstacle, and the subscript 'L' indicates the ultrasonic transmitter.

4. The ultrasonic transmission apparatus of claim 1, wherein
   a distance $d_0$ between the obstacle and the ultrasonic transmission member satisfies following Equation (3), $$d_0 = \frac{\varphi_0}{k_0} - \frac{c_{p0}}{2\omega} L \mathcal{X}(\alpha, \beta) \qquad \text{Equation (3)}$$

$$\left(\text{here}, \mathcal{X}(\alpha, \beta) \equiv R_B\left(R_L - \frac{T_L^2}{R_L}\right),\right.$$

$$R_B = \frac{-\frac{i}{2}\left(\frac{z_0}{z_B} - \frac{z_B}{z_0}\right)\sin(\varphi_B)}{\cos(\varphi_B) + \frac{i}{2}\left(\frac{z_0}{z_B} + \frac{z_B}{z_0}\right)\sin(\varphi_B)},$$

$$R_L = \frac{-\frac{i}{2}\left(\frac{z_0}{z_L} - \frac{z_L}{z_0}\right)\sin(\varphi_L)}{\cos(\varphi_L) + \frac{i}{2}\left(\frac{z_0}{z_L} + \frac{z_L}{z_0}\right)\sin(\varphi_L)},$$

$$\left. T_L = \frac{1}{\cos(\varphi_L) + \frac{i}{2}\left(\frac{z_0}{z_L} + \frac{z_L}{z_0}\right)\sin(\varphi_L)}\right)$$

the subscript '0' indicates the progress medium, the subscript 'B' indicates the obstacle, and the subscript 'L' indicates the ultrasonic transmitter.

5. The ultrasonic transmission apparatus of claim 1, wherein
   the ultrasonic transmission member satisfies following Equation (4), $$\alpha=1 \text{ and } \beta=1 \qquad \text{Equation (4).}$$

6. The ultrasonic transmission apparatus of claim 1, wherein,
   in the ultrasonic transmission member, when a distance $d_0$ between the obstacle and the ultrasonic transmission member satisfies following Equation (3), the ratio $\alpha$ and the ratio $\beta$ have valuses that satisfy following Equation (7) to Equation (9), $$d_0 = \frac{\varphi_0}{K_0} = \frac{c_{p0}}{2\omega} L \chi(\alpha, \beta), \qquad \text{Equation (3)}$$

-continued $$\eta_{EMMC1} \leq |X(\alpha, \beta)| \leq \eta_{EMMC2}, \quad \text{Equation (7)}$$

$$\eta_{EMMC1} = 1 - 7.0 \times (1 - |R_B|), \quad \text{Equation (8)}$$

$$\eta_{EMMC2} = 1 + 0.85 \times ((1 - |R_B|)) \quad \text{Equation (9)}$$

$$\left(\text{here, } X(\alpha, \beta) \equiv R_B\left(R_L - \frac{T_L^2}{R_L}\right),\right.$$

$$R_B = \frac{-\frac{i}{2}\left(\frac{z_0}{z_B} - \frac{z_B}{z_0}\right)\sin(\varphi_B)}{\cos(\varphi_B) + \frac{i}{2}\left(\frac{z_0}{z_B} + \frac{z_B}{z_0}\right)\sin(\varphi_B)},$$

$$R_L = \frac{-\frac{i}{2}\left(\frac{z_0}{z_L} - \frac{z_L}{z_0}\right)\sin(\varphi_L)}{\cos(\varphi_L) + \frac{i}{2}\left(\frac{z_0}{z_L} + \frac{z_L}{z_0}\right)\sin(\varphi_L)},$$

$$\left. T_L = \frac{1}{\cos(\varphi_L) + \frac{i}{2}\left(\frac{z_0}{z_L} + \frac{z_L}{z_0}\right)\sin(\varphi_L)}\right)$$

the subscript '0' indicates the progress medium, the subscript 'B' indicates the obstacle, and the subscript 'L' indicates the ultrasonic transmitter.

7. The ultrasonic transmission apparatus of claim 1, wherein,
in the ultrasonic transmission member, a distance $d_0$ between the obstacle and the ultrasonic transmission member satisfies following Equation (5) and Equation (6), and the ratio $\alpha$ and the ratio $\beta$ have values that satisfy following Equation (7) to Equation (9) when the distance $d_0$ between the obstacle and the ultrasonic transmission member satisfies following Equation (3), $$\frac{c_{p0}}{2\omega} L X(\alpha, \beta) - \eta_{EPMC} \leq d_0 \leq \frac{c_{p0}}{2\omega} L X(\alpha, \beta) + \eta_{EPMC}, \quad \text{Equation (5)}$$

$$\eta_{EPMC} = 0.655 \times (1 - |R_B|), \quad \text{Equation (6)}$$

$$d_0 = \frac{\varphi_0}{k_0} - \frac{c_{p0}}{2\omega} L X(\alpha, \beta), \quad \text{Equation (3)}$$

$$\eta_{EMMC1} \leq |X(\alpha, \beta)| \leq \eta_{EMMC2}, \quad \text{Equation (7)}$$

$$\eta_{EMMC1} = 1 - 7.0 \times (1 - |R_B|), \quad \text{Equation (8)}$$

$$\eta_{EMMC2} = 1 + 0.85 \times ((1 - |R_B|)) \quad \text{Equation (9)}$$

$$\left(\text{here, } X(\alpha, \beta) \equiv R_B\left(R_L - \frac{T_L^2}{R_L}\right),\right.$$

$$R_B = \frac{-\frac{i}{2}\left(\frac{z_0}{z_B} - \frac{z_B}{z_0}\right)\sin(\varphi_B)}{\cos(\varphi_B) + \frac{i}{2}\left(\frac{z_0}{z_B} + \frac{z_B}{z_0}\right)\sin(\varphi_B)},$$

$$R_L = \frac{-\frac{i}{2}\left(\frac{z_0}{z_L} - \frac{z_L}{z_0}\right)\sin(\varphi_L)}{\cos(\varphi_L) + \frac{i}{2}\left(\frac{z_0}{z_L} + \frac{z_L}{z_0}\right)\sin(\varphi_L)},$$

$$\left. T_L = \frac{1}{\cos(\varphi_L) + \frac{i}{2}\left(\frac{z_0}{z_L} + \frac{z_L}{z_0}\right)\sin(\varphi_L)}\right)$$

the subscript '0' indicates the progress medium, the subscript 'B' indicates the obstacle, and the subscript 'L' indicates the ultrasonic transmitter.

8. An ultrasonic transmission apparatus for performing an ultrasonic inspection by injecting an ultrasonic wave into an object including a medium and a body to be inspected inside and including an obstacle outside, the ultrasonic transmission apparatus comprising:
an ultrasonic generation device configured to generate an incident wave; and
an ultrasonic transmission module located between the obstacle and the ultrasonic generation device and located on a travel path of an incident wave generated by the ultrasonic generation device,
wherein the ultrasonic transmission module comprises:
an ultrasonic transmission member, and
a position variable device configured to vary a position of the ultrasonic transmission member, and
wherein the ultrasonic transmission member selectively varies impedance and a phase, and
a distance $d_0$ between the obstacle and the ultrasonic transmission member satisfies following Equation (5) and Equation (6), $$\frac{c_{p0}}{2\omega} L X(\alpha, \beta) - \eta_{EPMC} \leq d_0 \leq \frac{c_{p0}}{2\omega} L X(\alpha, \beta) + \eta_{EPMC}, \quad \text{Equation (5)}$$

$$\eta_{EPMC} = 0.655 \times (1 - |R_B|) \quad \text{Equation (6)}$$

$$\left(\text{here, } X(\alpha, \beta) \equiv R_B\left(R_L - \frac{T_L^2}{R_L}\right),\right.$$

$$R_B = \frac{-\frac{i}{2}\left(\frac{z_0}{z_B} - \frac{z_B}{z_0}\right)\sin(\varphi_B)}{\cos(\varphi_B) + \frac{i}{2}\left(\frac{z_0}{z_B} + \frac{z_B}{z_0}\right)\sin(\varphi_B)},$$

$$R_L = \frac{-\frac{i}{2}\left(\frac{z_0}{z_L} - \frac{z_L}{z_0}\right)\sin(\varphi_L)}{\cos(\varphi_L) + \frac{i}{2}\left(\frac{z_0}{z_L} + \frac{z_L}{z_0}\right)\sin(\varphi_L)},$$

$$\left. T_L = \frac{1}{\cos(\varphi_L) + \frac{i}{2}\left(\frac{z_0}{z_L} + \frac{z_L}{z_0}\right)\sin(\varphi_L)}\right)$$

the subscript '0' indicates the progress medium, the subscript 'B' indicates the obstacle, and the subscript 'L' indicates the ultrasonic transmitter.

9. A wave control method comprising:
varying a distance between an ultrasonic transmission member and an obstacle and a material of the ultrasonic transmission member in a state in which the ultrasonic transmission member is between an ultrasonic generation member and an obstacle; and transferring an ultrasonic wave generated by the ultrasonic generation member across the obstacle,
a ratio $\alpha$ between a phase of the obstacle and a phase of the ultrasonic transmission member and a ratio $\beta$ between impedance of the obstacle and impedance of the ultrasonic transmission member are defined according to following Equation (1), $$\alpha \equiv \frac{\varphi_L}{\varphi_B} = \frac{k_L d_L}{k_B d_B}, \beta \equiv \frac{Z_L}{Z_B} \quad \text{Equation (1)}$$

where $z = \rho c$ ($\rho$: density c: wave velocity)
$\Phi = kd$ (k: wavenumber, d: thickness of dissimilar material)
$k = \omega/c = $ ($\omega$: frequency [Rad/s])
$\omega = 2\pi f$ (f: frequency [Hz]))
the subscript 'B' indicates the obstacle, and the subscript 'L' indicates the ultrasonic transmitter.

10. The wave control method of claim 9, wherein
the ratio $\beta$ between the impedance of the obstacle and the impedance of the ultrasonic transmission member and the ratio α between the phase of the obstacle and the phase of the ultrasonic transmission member each satisfy following Equation (2), $$1 = |X(\alpha, \beta)| \qquad \text{Equation (2)}$$

$$\left(\text{here, } X(\alpha, \beta) \equiv R_B\left(R_L - \frac{T_L^2}{R_L}\right),\right.$$

$$R_B = \frac{-\frac{i}{2}\left(\frac{z_0}{z_B} - \frac{z_B}{z_0}\right)\sin(\varphi_B)}{\cos(\varphi_B) + \frac{i}{2}\left(\frac{z_0}{z_B} + \frac{z_B}{z_0}\right)\sin(\varphi_B)},$$

$$R_L = \frac{-\frac{i}{2}\left(\frac{z_0}{z_L} - \frac{z_L}{z_0}\right)\sin(\varphi_L)}{\cos(\varphi_L) + \frac{i}{2}\left(\frac{z_0}{z_L} + \frac{z_L}{z_0}\right)\sin(\varphi_L)},$$

$$\left.T_L = \frac{1}{\cos(\varphi_L) + \frac{i}{2}\left(\frac{z_0}{z_L} + \frac{z_L}{z_0}\right)\sin(\varphi_L)}\right)$$

the subscript '0' indicates the progress medium, the subscript 'B' indicates the obstacle, and the subscript 'L' indicates the ultrasonic transmitter.

11. The wave control method of claim 9, wherein a distance $d_0$ between the obstacle and the ultrasonic transmission member satisfies following Equation (3), $$d_0 = \frac{\varphi_0}{k_0} = \frac{c_{p0}}{2\omega} L X(\alpha, \beta) \qquad \text{Equation (3)}$$

$$\left(\text{here, } X(\alpha, \beta) \equiv R_B\left(R_L - \frac{T_L^2}{R_L}\right),\right.$$

$$R_B = \frac{-\frac{i}{2}\left(\frac{z_0}{z_B} - \frac{z_B}{z_0}\right)\sin(\varphi_B)}{\cos(\varphi_B) + \frac{i}{2}\left(\frac{z_0}{z_B} + \frac{z_B}{z_0}\right)\sin(\varphi_B)},$$

$$R_L = \frac{-\frac{i}{2}\left(\frac{z_0}{z_L} - \frac{z_L}{z_0}\right)\sin(\varphi_L)}{\cos(\varphi_L) + \frac{i}{2}\left(\frac{z_0}{z_L} + \frac{z_L}{z_0}\right)\sin(\varphi_L)},$$

$$\left.T_L = \frac{1}{\cos(\varphi_L) + \frac{i}{2}\left(\frac{z_0}{z_L} + \frac{z_L}{z_0}\right)\sin(\varphi_L)}\right)$$

the subscript '0' indicates the progress medium, the subscript 'B' indicates the obstacle, and the subscript 'L' indicates the ultrasonic transmitter.

12. The wave control method of claim 9, wherein the ultrasonic transmission member satisfies following Equation (4), $$\alpha = 1 \text{ and } \beta = 1 \qquad \text{Equation (4).}$$

13. The wave control method of claim 9, wherein a distance $d_0$ between the obstacle and the ultrasonic transmission member satisfies following Equation (5) and Equation (6), $$\frac{c_{p0}}{2\omega} L X(\alpha, \beta) - \eta_{EPMC} \leq d_0 \leq \frac{c_{p0}}{2\omega} L X(\alpha, \beta) + \eta_{EPMC}, \qquad \text{Equation (5)}$$

$$\eta_{EPMC} = 0.655 \times (1 - |R_B|) \qquad \text{Equation (6)}$$

$$\left(\text{here, } X(\alpha, \beta) \equiv R_B\left(R_L - \frac{T_L^2}{R_L}\right),\right.$$

$$R_B = \frac{-\frac{i}{2}\left(\frac{z_0}{z_B} - \frac{z_B}{z_0}\right)\sin(\varphi_B)}{\cos(\varphi_B) + \frac{i}{2}\left(\frac{z_0}{z_B} + \frac{z_B}{z_0}\right)\sin(\varphi_B)},$$

$$R_L = \frac{-\frac{i}{2}\left(\frac{z_0}{z_L} - \frac{z_L}{z_0}\right)\sin(\varphi_L)}{\cos(\varphi_L) + \frac{i}{2}\left(\frac{z_0}{z_L} + \frac{z_L}{z_0}\right)\sin(\varphi_L)},$$

$$\left.T_L = \frac{1}{\cos(\varphi_L) + \frac{i}{2}\left(\frac{z_0}{z_L} + \frac{z_L}{z_0}\right)\sin(\varphi_L)}\right)$$

the subscript '0' indicates the progress medium, the subscript 'B' indicates the obstacle, and the subscript 'L' indicates the ultrasonic transmitter.

14. The wave control method of claim 9, wherein, when a distance $d_0$ between the obstacle and the ultrasonic transmission member satisfies following Equation (3), the ratio α and the ratio β have values that satisfy following Equation (7) to Equation (9), $$d_0 = \frac{\varphi_0}{k_0} = \frac{c_{p0}}{2\omega} L X(\alpha, \beta), \qquad \text{Equation (3)}$$

$$\eta_{EMMC1} \leq |X(\alpha, \beta)| \leq \eta_{EMMC2}, \qquad \text{Equation (7)}$$

$$\eta_{EMMC1} = 1 - 7.0 \times (1 - |R_B|), \qquad \text{Equation (8)}$$

$$\eta_{EMMC2} = 1 + 0.85 \times ((1 - |R_B|) \qquad \text{Equation (9)}$$

$$\left(\text{here, } X(\alpha, \beta) \equiv R_B\left(R_L - \frac{T_L^2}{R_L}\right),\right.$$

$$R_B = \frac{-\frac{i}{2}\left(\frac{z_0}{z_B} - \frac{z_B}{z_0}\right)\sin(\varphi_B)}{\cos(\varphi_B) + \frac{i}{2}\left(\frac{z_0}{z_B} + \frac{z_B}{z_0}\right)\sin(\varphi_B)},$$

$$R_L = \frac{-\frac{i}{2}\left(\frac{z_0}{z_L} - \frac{z_L}{z_0}\right)\sin(\varphi_L)}{\cos(\varphi_L) + \frac{i}{2}\left(\frac{z_0}{z_L} + \frac{z_L}{z_0}\right)\sin(\varphi_L)},$$

$$\left.T_L = \frac{1}{\cos(\varphi_L) + \frac{i}{2}\left(\frac{z_0}{z_L} + \frac{z_L}{z_0}\right)\sin(\varphi_L)}\right)$$

the subscript '0' indicates the progress medium, the subscript 'B' indicates the obstacle, and the subscript 'L' indicates the ultrasonic transmitter.

15. The wave control method of claim 9, wherein, a distance $d_0$ between the obstacle and the ultrasonic transmission member satisfies following Equation (5) and Equation (6), and the ratio α and the ratio β have values that satisfy following Equation (7) to Equation (9) when the distance $d_0$ between the obstacle and the ultrasonic transmission member satisfies following Equation (3), $$\frac{c_{p0}}{2\omega} L X(\alpha, \beta) - \eta_{EPMC} \leq d_0 \leq \frac{c_{p0}}{2\omega} L X(\alpha, \beta) + \eta_{EPMC}, \qquad \text{Equation (5)}$$

$$\eta_{EPMC} = 0.655 \times (1 - |R_B|), \qquad \text{Equation (6)}$$

$$d_0 = \frac{\varphi_0}{k_0} = \frac{c_{p0}}{2\omega} L X(\alpha, \beta), \qquad \text{Equation (3)}$$

$$\eta_{EMMC1} \leq |X(\alpha, \beta)| \leq \eta_{EMMC2}, \qquad \text{Equation (7)}$$

-continued $$\eta_{EMMC1} = 1 - 7.0 \times (1 - |R_B|),\quad \text{Equation (8)}$$

$$\eta_{EMMC2} = 1 + 0.85 \times ((1 - |R_B|)\quad \text{Equation (9)}$$

$$\left(\text{here, } \mathcal{X}(\alpha, \beta) \equiv R_B\left(R_L - \frac{T_L^2}{R_L}\right),\right.$$

$$R_B = \frac{-\frac{i}{2}\left(\frac{z_0}{z_B} - \frac{z_B}{z_0}\right)\sin(\varphi_B)}{\cos(\varphi_B) + \frac{i}{2}\left(\frac{z_0}{z_B} + \frac{z_B}{z_0}\right)\sin(\varphi_B)},$$

$$R_L = \frac{-\frac{i}{2}\left(\frac{z_0}{z_L} - \frac{z_L}{z_0}\right)\sin(\varphi_L)}{\cos(\varphi_L) + \frac{i}{2}\left(\frac{z_0}{z_L} + \frac{z_L}{z_0}\right)\sin(\varphi_L)},$$

$$\left.T_L = \frac{1}{\cos(\varphi_L) + \frac{i}{2}\left(\frac{z_0}{z_L} + \frac{z_L}{z_0}\right)\sin(\varphi_L)}\right)$$

the subscript '0' indicates the progress medium, the subscript 'B' indicates the obstacle, and the subscript 'L' indicates the ultrasonic transmitter.

\* \* \* \* \*